United States Patent
Tanikawa et al.

[11] Patent Number: 6,066,631
[45] Date of Patent: May 23, 2000

[54] CHROMAN DERIVATIVES

[75] Inventors: Keizo Tanikawa; Kazuhiko Ohrai; Masayuki Sato, all of Funabashi; Toru Yamashita; Kazufumi Yanagihara, both of Minamisaitama, all of Japan

[73] Assignee: Nissan Chemical Industries, Ltd., Tokyo, Japan

[21] Appl. No.: 09/232,645

[22] Filed: Jan. 19, 1999

Related U.S. Application Data

[63] Continuation of application No. PCT/JP97/02583, Jul. 25, 1997.

[30] Foreign Application Priority Data

Jul. 19, 1996 [JP] Japan .................................. 8-197819

[51] Int. Cl.$^7$ ..................... A61K 31/352; C07D 251/00; C07D 405/00; C07D 401/00
[52] U.S. Cl. ...................... 514/212; 546/196; 546/282.7; 544/238; 544/333; 540/524
[58] Field of Search ................................. 546/196, 282.7, 546/282.1; 514/320, 253, 256, 212, 337, 456; 544/238, 333; 549/404; 540/524

[56] References Cited

U.S. PATENT DOCUMENTS

| | | | |
|---|---|---|---|
| 5,097,037 | 3/1992 | Matsumoto et al. | 548/126 |
| 5,420,314 | 5/1995 | Katsuki et al. | 549/533 |

FOREIGN PATENT DOCUMENTS

| | | |
|---|---|---|
| 0 409 165 A2 | 1/1991 | European Pat. Off. . |
| 0 535 377 A2 | 4/1993 | European Pat. Off. . |
| 51-1477 | 1/1976 | Japan . |
| 56-57785 | 5/1981 | Japan . |
| 56-57786 | 5/1981 | Japan . |
| 58-67683 | 4/1983 | Japan . |
| 58-188880 | 11/1983 | Japan . |
| 58-201776 | 11/1983 | Japan . |
| 3-141286 | 6/1991 | Japan . |
| 5-301878 | 11/1993 | Japan . |
| 7-285983 | 10/1995 | Japan . |
| WO 85/01290 | 3/1985 | WIPO . |
| WO 98/04542 | 2/1998 | WIPO . |

*Primary Examiner*—Zinna Northington Davis
*Assistant Examiner*—Binta Robinson
*Attorney, Agent, or Firm*—Oliff & Berridge, PLC

[57] ABSTRACT

The present invention relates to chroman derivatives of the formula (I):

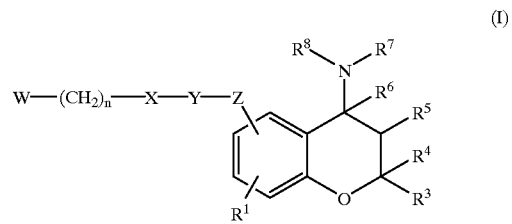

[wherin $R^1$ represents a hydrogen atom, a halogen atom, a $C_{1-6}$ alkyl group, a $C_{1-6}$ alkoxy group, a $C_{3-6}$ alkoxymethyl group, etc., $R^3$ and $R^4$ each independently represent a hydrogen atom, a $C_{1-6}$ alkyl group, etc., $R^5$ represents a hydroxyl group or a $C_{1-6}$ alkylcarbonyloxyl group or forms a bond together with $R^5$, $R^6$ represents a hydrogen atom or forms a bond together with $R^5$, $R^7$ and $R^8$ each independently represent a hydrogen atom, a $C_{1-6}$ alkyl group, a $C_{3-6}$ cycloalkyl group, a phenyl group, etc. n is 0 or an integer of 1, 2, 3 or 4, W represents a phenyl group, etc., X represents C=O, $CH_2$, $SO_2$, etc., Y represents $NR^{17}$ (in which $R^{17}$ represents a hydrogen atom, a $C_{1-4}$ alkyl group, a phenyl group, etc.), etc., Z does not exist or represents $CH_2$ or $NR^{18}$ ($R^{18}$ represents a hydrogen atom, a $C_{1-4}$ alkyl group, or a phenyl group, etc.)] or their salts.

28 Claims, No Drawings

CHROMAN DERIVATIVES

This is a Continuation of International Application No. PCT/JP97/02583 filed Jul. 25, 1997. The entire disclosure of the prior application is hereby incorporated by reference herein in its entirety.

TECHNICAL FIELD

The present invention relates to chroman derivatives having bradycardia activities and is used for treating cardiac insufficiency in mammals inclusive of human being.

Japanese Patent Application Laid-open No. Sho 51-1477, Japanese Patent Application Laid-open No. Sho 56-57785, Japanese Patent Application Laid-open No. Sho 56-57786 and European Patent Publication No. 157843 (EP-A 157843) have reported that benzopyran derivatives were used for treating hypertension. Japanese Patent Application Laid-open No. Hei 5-1059 has reported benzopyran derivatives were used for treating peptic ulcer. However, none of them does refer to the possibility that the benzopyran derivatives can treat cardiac insufficient pathorogy.

The cardiac insufficiency which is a state of insufficient function of heart is a disease which is based on the depression of contraction of heart muscles. As a treatment therefor, it has been clinically used medicines for reinforcing the contraction of cardiac muscles. However, these medicines have such a problem that heart muscles energey is excessively consumed on the basis of the increase of the heart rate and thus, they have had problems to be solved with respect to effects to improve life recuperation after the administration of these medicines in a long period of time. It has been, therefore, desired to develop medicines which reduce load in consumption of heart muscle energy by reducing heart rate.

DISCLOSURE OF THE INVENTION

As a result of the inventors' intensive study and investigation of chroman derivatives, the inventors found out that compounds of the formula (I) which reduce heart rate have strong bradycardia activities and are useful as medicines for curing cardiac insufficiency, and they completed the present invention.

The present invention relates to chroman derivatives of the formula (I):

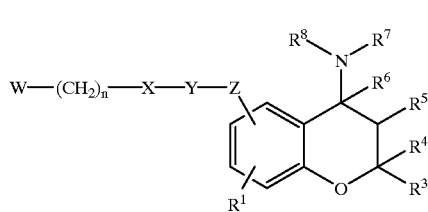

(I)

[in which, $R^1$ represents a hydrogen atom, a halogen atom, a $C_{1-6}$ alkyl group {said alkyl group is unsubstituted or substituted by a halogen atom, a carboxyl group, a $C_{1-6}$ alkoxy group, a $C_{2-6}$ alkoxycarbonyl group, a hydroxyl group, a formyl group, a cyano group or a nitro group}, a $C_{1-6}$ alkoxy group {said alkoxy group is unsubstituted or substituted by a halogen atom, a carboxyl group, a $C_{2-6}$ alkoxycarbonyl group, a hydroxyl group, a phenyl group (said phenyl group is unsubstituted or substituted by $R^2$ (said $R^2$ represents a halogen atom, a hydroxyl group, a $C_{1-4}$ alkyl group or a $C_{1-4}$ alkoxy group)), a formyl group, a cyano group or a nitro group}, a $C_{3-6}$ cycloalkyl group {said cycloalkyl group is unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$), a formyl group, a cyano group or a nitro group}, a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group {said alkylamino group and said di $C_{1-6}$ alkylamino group are unsubstituted or substituted by a halogen atom, a carboxyl group, a $C_{2-6}$ alkoxycarbonyl group, a hydroxyl group, a formyl group, a cyano group or a nitro group}, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, a $C_{1-6}$ alkylcarbonyloxy group, a $C_{1-6}$ alkylurea group, a $C_{1-6}$ alkylthiourea group, an aryl $C_{1-6}$ alkylamino group, a di(aryl $C_{1-6}$ alkyl) amino group, an arylcarbonylamino group, an aryl $C_{1-6}$ alkylcarbonylamino group, an arylsulfonylamino group, an aryl $C_{1-6}$ alkylsulfonylamino group, an aryl $C_{1-6}$ alkylaminocarbonyl group, a di(aryl $C_{1-6}$ alkyl)aminocarbonyl group, an arylcarbonyl group, an aryl $C_{1-6}$ alkylcarbonyl group, an aryloxycarbonyl group, an aryl $C_{1-6}$ alkyloxycarbonyl group, an arylcarbonyloxy group, an aryl $C_{1-6}$ alkylcarbonyloxy group, an arylurea group, an aryl $C_{1-6}$ alkylurea group, an arylthiourea group or an aryl $C_{1-6}$ alkylthiourea group {said aryl $C_{1-6}$ alkylamino group, a di(aryl $C_{1-6}$ alkyl)amino group, an arylcarbonylamino group, an aryl $C_{1-6}$ alkylcarbonylamino group, an arylsulfonylamino group, an aryl $C_{1-6}$ alkylsulfonylamino group, an aryl $C_{1-6}$ alkylaminocarbonyl group, a di(aryl $C_{1-6}$ alkyl) aminocarbonyl group, an arylcarbonyl group, an aryl $C_{1-6}$ alkylcarbonyl group, an aryloxycarbonyl group, an aryl $C_{1-6}$ alkyloxycarbonyl group, an arylcarbonyloxy group, an aryl $C_{1-6}$ alkylcarbonyloxy group, an arylurea group, an aryl $C_{1-6}$ alkylurea group, an arylthiourea group and an aryl $C_{1-6}$ alkylthiourean group each are unsubstituted or substituted by $R^{19}$ (said $R^{19}$ represents a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$), a formyl group, a cyano group or a nitro group)}, $R^3$ and $R^4$ each independently represent a hydrogen atom or a $C_{1-6}$ alkyl group {said alkyl group is unsubstituted or substituted by a halogen atom, a $C_{1-6}$ alkoxy group or a hydroxyl group} or $R^3$ and $R^4$, together with the carbon atom, which they are bonded, form a $C_{3-6}$ cycloalkyl group.

$R^5$ represents a hydroxyl group or a $C_{1-6}$ alkylcarbonyloxy group or forms a bond together with $R^6$, $R^6$ represents a hydrogen atom or forms a bond together with $R^5$, $R^7$ and $R^8$ each independently represent a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each is unsubstituted or substituted by $R^{19}$}, a phenyl group (said phenyl group is unsubstituted or substituted by $R^2$), $C(=Y^1)Z^1R^{10}$ or $C(=Y^1)R^{10}$ {$Y^1$ represents an oxygen atom, a sulfur atom or $NR^{11}$ ($R^{11}$ represents a hydrogen atom, a cyano group, a nitro group, a $C_{1-6}$ alkyl group or a $C_{1-6}$ alkoxy group), $Z^1$ represents an oxygen atom, a sulfur atom or $NR^{13}$ ($R^{13}$ has the same meaning as defined in $R^{10}$), $R^{10}$ represents a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each are unsubstituted or substituted by $R^{19}$) or a phenyl group (said phenyl group is unsubstituted or substituted by $R^2$)}, or $R^7$ and $R^8$ together form a 1,4-butylene or a 1,5-pentylene {said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-6}$ alkylcarbonyloxy group}, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ represents a hydrogen atom, a $C_{1-4}$ alkyl group or a phenyl group (said phenyl group is unsubstituted or substituted by $R^2$))), or $R^7$ and $R^8$ together form $(CH_2)_q Z^1 C(=Y^1)$ or $(CH_2)_q C(=Y^1)$ (q represents 2, 3 or 4 and $Z^1$ and $Y^1$ have the same meanings as defined above), or $R^7$ and $R^8$, together with the nitrogen atom to which they are bonded, form a pyrrolyl group, a pyrazolyl group, an imidazolyl group, a 1,2,3-triazolyl group, a 1,2,4-triazolyl group or a 1,2,3,4-tetrazolyl group all of which are unsubstituted or substituted by $R^{15}$ ($R^{15}$ has the same meaning as defined in $R^{10}$).

n is 0 or an integer of 1, 4,

X represents C=O, $CH_2$, $SO_2$ or $NR^{16}$ ($R^{16}$ has the same meanings as definend in $R^{14}$), Y represents $NR^{17}$ ($R^{17}$ has the same meanings as defined in $R^{14}$) when X is C=O, $CH_2$ or $SO_2$ and represents C=O when X is $NR^{16}$, Z is absent or represents $CH_2$ or $NR^{18}$ ($R^{18}$ has the same meanings as definend in $R^{14}$), W represents (in which $R^9$ represents a hydrogen atom, a halogen atom, a $C_{1-6}$ alkyl group (said alkyl group is unsubstituted or substituted by a halogen atom or a $C_{1-6}$ alkoxy group), a $C_{1-6}$ alkoxy group (said alkoxy group is unsubstituted or substituted by a halogen atom), a phenyl group (said phenyl group is unsubstituted or substituted by $R^2$), a hydroxyl group, a nitro group, a cyano group, a formyl group, a formamide group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group, a carboxyl group or an arylcarbonyl group, m is an integer of 1 to 3, and $R^{12}$ represents a $C_{1-4}$ alkyl group)] or salts thereof.

The compounds of the present invention have strong activities for reducing heart rate and are useful for improving cardiac functions, and can be used as medicines for curing cardiac insufficiency.

The substituents in the compounds of the formula (I) will be explained in more detail hereunder.

In this specification, "n" means normal; "i" means iso; "s" means secondary; "t" means tertiary; "c" means cyclo; "o" means ortho; "m" means metha and "p" means para.

As the halogen atom, a fluorine atom, a chlorine atom, a bromine atom and an iodine atom can be mentioned. Preferable ones are the fluorine atom, the chlorine atom and the bromine atom.

As the $C_{1-6}$ alkyl group, a methyl, an ethyl, an n-propyl, an i-propyl, an n-butyl, an i-butyl, an s-butyl, a t-butyl, a 1-pentyl, a 2-pentyl, a 3-pentyl, an i-pentyl, a neopentyl, a 2,2-dimethylpropyl, a 1-hexyl, a 2-hexyl, a 3-hexyl, a 1-methyl-n-pentyl, a 1,1,2-trimethyl-n-propyl, a 1,2,2-trimethyl-n-propyl, a 3,3-dimethyl-n-butyl, a trifluoromethyl, a trifluoroethyl, a pentafluoroethyl, a cyanomethyl and a hydroxymethyl, etc. can be mentioned.

Preferable ones are the methyl, the ethyl, the n-propyl, the i-propyl and the n-butyl.

As the $C_{1-6}$ alkoxy group, a methoxy, a trifluoromethoxy, an ethoxy, an n-propoxy, an i-propoxy, an n-butoxy, an i-butoxy, an s-butoxy, a t-butoxy, a 1-pentyloxy, a 2-pentyloxy, a 3-pentyloxy, an i-pentyloxy, a neopentyloxy, a 2,2-dimethylpropoxy, a 1-hexyloxy, a 2-hexyloxy, a 3-hexyloxy, a 1-methyl-n-pentyloxy, a 1,1,2-trimethyl-n-propoxy, a 1,2,2-trimethyl-n-propoxy, a 3,3-dimethyl-n-butoxy, etc. can be mentioned.

Preferable ones are the methoxy, the ethoxy, the n-propoxy and the i-propoxy.

As the aryl group, a phenyl, a biphenylyl, a naphthyl, an anthryl and a phenanthryl, etc. can be mentioned.

Preferable ones are the phenyl, the biphenylyl and the naphthyl.

As the $C_{3-6}$ cycloalkyl group, a cyclopropyl, a cyclobutyl, a cyclopentyl, a cyclohexyl, a cycloheptyl and a cyclooctyl, etc. can be mentioned.

Preferable ones are the cyclopropyl, the cyclobutyl and the cyclohexyl.

As the $C_{1-6}$ alkylamino group, a methylamino, an ethylamino, an n-propylamino, an i-propylamino, a c-propylamino, an n-butylamino, an i-butylamino, an s-butylamino, a t-butylamino, a c-butylamino, a 1-penthylamino, a 2-pentylamino, a 3-pentylamino, an i-pentylamino, a neopentylamino, a t-pentylamino, a c-pentylamino, a 1-hexylamino, a 2-hexylamino, a 3-hexylamino, a c-hexylamino, a 1-methyl-n-pentylamino, a 1,1,2-trimethyl-n-propylamino, a 1,2,2-trimethyl-n-propylamino and a 3,3-dimethyl-n-butylamino, etc. can be mentioned.

The preferable ones are the methylamino, the ethylamino, the n-propylamino, the i-propylamino and the n-butylamino.

As the di $C_{1-6}$ alkylamino group, a dimethylamino, a diethylamino, a di-n-propylamino, a di-i-propylamino, a di-c-propylamino, a di-n-butylamino, a di-i-butylamino, a di-s-butylamino, a di-t-butylamino, a di-c-butylamino, a di-1-pentylamino a di-2-pentylamino, a di-3-pentylamino, a di-i-pentylamino, a di-neopentylamino, a di-t-pentylamino, a di-c-pentylamino, a di-1-hexylamino, a di-2-hexylamino, a di-3-hexylamino, a di-c-hexylamino, a di-(1-methyl-n- pentyl)amino, a di-(1,1,2-trimethyl-n-propyl)amino, a di-(1,
2,2-trimethyl-n-propyl)amino, a di-(3,3-dimethyl-n-butyl)
amino, a methyl(ethyl)amino, a methyl(n-propyl)amino, a
methyl(i-propyl)amino, a methyl(c-propyl)amino, a methyli
(n-butyl)amino, a methyl(i-butyl)amino, a methyl(s-butyl)
amino, a methyl(t-butyl)amino, a methyl(c-butyl)amino, an
ethyl(n-propyl)amino, an ethyl(i-propyl)amino, an ethyl(c-
propyl)amino, an ethyli(n-butyl)amino, an ethyl(i-butyl)
amino, an ethyl(s-butyl)amino, an ethyl(t-butyl)amino, an
ethyl(c-butyl)amino, an n-propyl(i-propyl)amino, an
n-propyl(c-propyl)amino, an n-propylp(n-butyl)amino, an
n-propyl(i-butyl)amino, an n-propyl(s-butyl)amino, an
n-propyl(t-butyl)amino, an n-propyl(c-butyl)amino, an
i-propyl(c-propyl)amino, an i-propyl(n-butyl)amino, an
i-propyl(i-butyl)amino, an i-propyl(s-butyl)amino, an
i-propyl(t-butyl)amino, an i-propyl(c-butyl)amino, a
c-propyl(n-butyl)amino, a c-propyl(i-butyl)amino, a
c-propyl(s-butyl)amino, a c-propyl(t-butyl)amino, a
c-propyl(c-butyl)amino, an n-butyl(i-butyl)amino, an
n-butyl(s-butyl)amino, an n-butyl(t-butyl)amino, an n-butyl
(c-butyl)amino, an i-butyl(s-butyl)amino, an i-butyl(t-butyl)
amino, an i-butyl(c-butyl)amino, an s-butyl(t-butyl)amino,
an s-butyl(c-butyl)amino and a t-butyl(c-butyl)amino, etc.
can be mentioned.

Preferable ones are the dimethylamino, the diethylamino,
the di-n-propylamino, the di-i-propylamino and the di-n-
butylamino.

As the aryl $C_{1-6}$ alkylamino group, a benzylamino, an
o-methylbenzylamino, an m-methylbenzylamino, a
p-methylbenzylamino, an o-chlorobenzylamino, an
m-chlorobenzylamino, a p-chlorobenzylamino, an
o-fluorobenzylamino, a p-fluorobenzylamino, an
o-methoxybenzylamino, a p-methoxybenzylamino, a
p-nitrobenzylamino, a p-cyanobnezylamino, a phenethyl
amino, an o-methylphenethylamino, an
m-methylphenethylamino, a p-methylphenethylamino, an
o-chlorophenethylamino, an m-chlorophenethylamino, a
p-chlorophenethylamino, an o-fluorophenethylamino, a
p-fluorophenethylamino, an o-methoxyphenethylamino, a
p-methoxyphenethylamino, a p-nitrophenethylamino, a
p-cyanophenethylamino, a phenylpropylamino, a
phenylbutylamino, a phenylpentylamino, a
phenylhexylamino, a naphthylamino, a biphenylylamino, an
anthrylamino and a phenanthrylamino can be mentioned.

Preferable ones are the benzylamino, the
p-methylbenzylamino, the phenethylamino, the
p-methoxyphenethylamino and the phenylpropylamino.

As the $C_{1-6}$ alkylcarbonylamino group, a
methylcarbonylamino, an ethylcarbonylamino, an
n-propylcarbonylamino, an i-propylcarbonylamino, an
n-butylcarbonylamino, an i-butylcarbonylamino, an
s-butylcarbonylamino, a t-butylcarbonylamino, a
1-pentylcarbonylamino, a 2-pentylcarbonylamino, a
3-pentylcarbonylamino, an i-pentylcarbonylamino, a
neopentylcarbonylamino, a t-pentylcarbonylamino, a
1-hexylcarbonylamino, a 2-hexylcarbonylamino and a
3-hexylcarbonylamino, etc. can be mentioned.

Preferable ones are the methylcarbonylamino, the
ethylcarbonylamino, the n-propylcarbonylamino, the
i-propylcarbonylamino and the n-butylcarbonylamino.

As the arylcarbonylamino group, a benzoylamino, a
1-naphthylcarbonylamino, a 2-naphthylcarbonylamino, an
o-methylbenzoylamino, an m-methylbenzoylamino, a
p-methylbenzoylamino, an o-chlorobenzoylamino, a
p-chlorobenzoylamino, an o-fluorobenzoylamino, a
p-fluorobenzoylamino, an o-methoxybenzoylamino, a
p-methoxybenzoylamino, a p-nitrobenzoylamino, a
p-cyanobenzoylamino and a p-phenylbenzoylamino, etc.
can be mentioned.

Preferable ones are the benzoylamino and the
p-fluorobenzoylamino.

As the aryl $C_{1-6}$ alkylcarbonylamino group, a
phenylacetylamino, an o-methylphenylacetylamino, an
m-methylphenylacetylamino, a
p-methylphenylacetylamino, an
o-chlorophenylacetylamino, a p-chlorophenylacetylamino, a
p-fluorophenylacetylamino, an
o-methoxyphenylacetylamino, a
p-methoxyphenylacetylamino, a p-nitrophenylacetylamino,
a p-cyanophenylacetylamino, a
2-phenylethylcarbonylamino, a
3-phenylpropylcarbonylamino, a
4-phenylbutylcarbonylamino, a
5-phenylpentylcarbonylamino and a
6-phenylhexylcarbonylamino, etc. can be mentioned.

Preferable ones are the phenylacetylamino and the
2-phenylethylcarbonylamino.

As the $C_{1-6}$ alkylsulfonylamino group, a
methylsulfonylamino, an ethylsulfonylamino, an
n-propylsulfonylamino, an i-propylsulfonylamino, an
n-butylsulfonylamino, an i-butylsulfonylamino, an
s-butylsulfonylamino, a t-butylsulfonylamino, a
1-pentylsulfonylamino, a 2-pentylsulfonylamino, a
3-pentylsulfonylamino, an i-pentylsulfonylamino, a
neopentylsulfonylamino, a t-pentylsulfonylamino, a
1-hexylsulfonylamino, a 2-hexylsulfonylamino and a
3-hexylsulfonylamino, etc. can be mentioned.

Preferable ones are the methylsulfonylamino, the
ethylsulfonylamino, the n-propylsulfonylamino, the
i-propylsulfonylamino and the n-butylsulfonylamino.

As the arylsulfonylamino group, a benzensulfonylamino
and a p-toluenesulfonylamino can be mentioned.

As the $C_{1-6}$ alkylaminocarbonyl group, a
methylaminocarbonyl, an ethylaminocarbonyl, an
n-propylaminocarbonyl, an i-propylaminocarbonyl, an
n-butylaminocarbonyl, an i-butylaminocarbonyl, an
s-butylaminocarbonyl, a t-butylaminocarbonyl, a
1-pentylaminocarbonyl, a 2-pentylaminocarbonyl, a
3-pentylaminocarbonyl, an i-pentylaminocarbonyl, a
neopentylaminocarbonyl, a t-pentylaminocarbonyl, a
1-hexylaminocarbonyl, a 2-hexylaminocarbonyl and a
3-hexylaminocarbonyl, etc. can be mentioned.

Preferable ones are the methylaminocarbonyl, the
ethylaminocarbonyl, the n-propylaminocarbonyl, the
i-propylaminocarbonyl and the n-butylaminocarbonyl.

As the di $C_{1-6}$ alkylaminocarbonyl group, a
dimethylaminocarbonyl, a diethylaminocarbonyl, a di-n-
propylaminocarbonyl, a di-i-propylaminocarbonyl, a di-c-
propylaminocarbonyl, a di-n-butylaminocarbonyl, a di-i-
butylaminocarbonyl, a di-s-butylaminocarbonyl, a di-t-
butylaminocarbonyl, a di-c-butylaminocarbonyl, a di-1-
pentylaminocarbonyl, a di-2-pentylaminocarbonyl, a di-3-
pentylaminocarbonyl, a di-i-pentylaminocarbonyl, a
di-neopentylaminocarbonyl, a di-t-pentylaminocarbonyl, a
di-c-pentylaminocarbonyl, a di-1-hexylaminocarbonyl, a
di-2-hexylaminocarbonyl and a di-3-hexylaminocarbonyl,
etc. can be mentioned.

Preferable ones are the dimentylaminocarbonyl, the
diethylaminocarbonyl, the di-n-propylaminocarbonyl, the
di-i-propylaminocarbonyl, the di-c-propylaminocarbonyl
and the di-n-butylaminocarbonyl.

As the aryl $C_{1-6}$ alkylaminocarbonyl group, a
benzylaminocarbonyl, an o-methylbenzylaminocarbonyl an
m-methylbenzylaminocarbonyl, a p-methylbenzylaminocarbonyl, an o-chlorobenzylaminocarbonyl, a p-chlorobenzylaminocarbonyl, an o-fluorobenzylaminocarbonyl, a p-fluorobenzylaminocarbonyl, an o-coethoxybenzylaminocarbonyl, a p-methoxybenzylaminocarbonyl, a p-nitrobenzylaminocarbonyl, a p-cyanobenzylaminocarbonyl, a phenethylaminocarbonyl, a phenethylaninocarbonyl, a p-methylphenethylaminocarbonyl, a p-chlorophenethylaminocarbonyl, a p-cyanophenethylaminocarbonyl, a phenethylaminocarbonyl, a 3-phenylpropylaminocarbonyl, a 4-phenylbutylaminocarbonyl, a 5-phenylpentylaminocarbonyl and a 6-phenylhexylaminocarbonyl can be mentioned.

Preferable ones are the benzylaminocarbonyl, the p-methylbenzylaminocarbonyl, the p-chlorobenzylaminocarbonyl, the p-fluorobenzylaminocarbonyl and the phenethylaminocarbonyl.

As the $C_{1-6}$ alkylcarbonyl group, a methylcarbonyl, an ethylcarbonyl, an n-propylcarbonyl, an i-propylcarbonyl, an n-butylcarbonyl, an i-butylcarbonyl, an s-butylcarbonyl, a t-butylcarbonyl, a 1-pentylcarbonyl, a 2-pentylcarbonyl, a 3-pentylcarbonyl, an i-pentylcarbonyl, a neopentylcarbonyl, a t-pentylcarbonyl, a 1-hexylcarbonyl, a 2-hexylcarbonyl and a 3-hexylcarbonyl can be mentioned.

Preferable ones are the methylcarbonyl, the ethylcarbonyl, the n-propylcarbonyl, the i-propylcarbonyl and the n-butylcarbonyl.

As the arylcarbonyl group, a benzoyl, a p-methylbenzoyl, a p-t-butylbenzoyl, a p-methoxybenzoyl, a p-chlorobenzoyl, a p-nitrobenzoyl and a p-cyanobenzoyl can be mentioned.

Preferable ones are the benzoyl, the p-nitrobenzoyl and the p-cyanobenzoyl.

As the aryl $C_{1-6}$ alkylcarbonyl group, a phenylacetyl, a p-methylphenylacetyl, a p-t-butylphenylacetyl, a p-methoxyphenylacetyl, a p-chlorophenylacetyl, a p-nitrophenylacetyl, a p-cyanophenylacetyl, a phenethylcarbonyl, a 3-phenylpropyl, a 4-phenylbutyl, 5-phenylpentyl and a 6-phenylhexyl can be mentioned.

Preferable ones are the phenylacetyl and phenethylcarbonyl.

As the $C_{1-6}$ alkoxycarbonyl group, a methoxycarbonyl, an ethoxycarbonyl, an n-propoxycarbonyl, an i-propoxycarbonyl, an n-butoxycarbonyl, an i-butoxycarbonyl, an s-butoxycarbonyl, a t-butoxycarbonyl, a 1-pentyloxycarbonyl, a 2-pentyloxycarbonyl, a 3-pentyloxycarbonyl, an i-pentyloxycarbonyl, a neopentyloxycarbonyl, a t-penthyloxycarbonyl, a 1-hexyloxycarbonyl, a 2-hexyloxycarbonyl and a 3-hexyloxycarbonyl can be mentioned.

Preferable ones are the methoxycarbonyl, the ethoxycarbonyl, the n-propoxycarbonyl, the i-propoxycarbonyl, the n-butoxycarbonyl, the i-butoxycarbonyl, the s-butoxycarbonyl and the t-butoxycarbonyl.

As the aryloxycarbonyl group, a phenoxycarbonyl, an o-methylphenoxycarbonyl, a p-methylphenoxycarbonyl, a p-chlorophenoxycarbonyl, a p-fluorophenoxycarbonyl, a p-methoxyphenoxycarbonyl, a p-nitrophenoxycarbonyl, a p-cyanophenoxycarbonyl, a 1-naphthoxycarbonyl and a 2-naphthoxycarbonyl can be mentioned.

As the aryl $C_{1-6}$ alkyloxycarbonyl group, a benzyloxycarbonyl, an o-methylbenzyloxycarbonyl, a p-methylbenzyloxycarbonyl, a p-chlorobenzyloxycarbonyl, a p-fluorobenzyloxycarbonyl, a p-methoxybenzyloxycarbonyl, a p-nitrobenzyloxycarbonyl, a p-cyanobenzyloxycarbonyl, a 1-naphthoxymethylcarbonyl, a 2-naphthoxymethylcarbonyl and a pyridylmethyloxycarbonyl can be mentioned.

As the $C_{1-6}$ alkylcarbonyloxy group, a methylcarbonyloxy, an ethylcarbonyloxy, an n-propylcarbonyloxy, an i-propylcarbonyloxy, an n-butylcarbonyloxy, an i-butylcarbonyloxy, an s-butylcarbonyloxy, a t-butylcarbonyloxy, a 1-pentylcarbonyloxy, a 2-pentylcarbonyloxy, a 3-pentylcarbonyloxy, an i-penthylcarbonyloxy, a neopentylcarbonyloxy, a t-pentylcarbonyloxy, a 1-hexylcarbonyloxy, a 2-hexylcarbonyloxy, a 3-hexylcarbonyloxy, a 1-methyl-n-pentylcarbonyloxy, a 1,1,2-trimethyl-n-propylcarbonyloxy, a 1,2,2-trimethyl-n-propylcarbonyloxy and 3,3-dimethyl-n-butylcarbonyloxy, etc. can be mentioned.

Preferable ones are the methylcarbonyloxy, the ethylcarbonyloxy, the n-propylcarbonyloxy, the i-propylcarbonyloxy, the n-butylcarbonyloxy and the t-butylcarbonyloxy.

As the arylcarbonyloxy group, a benzoyloxy, an o-methylbenzoyloxy, a p-methylbenzoyloxy, a p-chlorobenzoyloxy, a p-fluorobenzoyloxy, a p-methoxybenzoyloxy, a p-nitrobenzoyloxy, a p-cyanobenzoyloxy, a 1-naphthylcarbonyloxy and a 2-naphthylcarbonyloxy.

As the aryl $C_{1-6}$ alkylcarbonyloxy group, a benzylcarbonyloxy, an o-methylbenzylcarbonyloxy, a p-methylbenzylcarbonyloxy, a p-chlorobenzylcarbonyloxy, a p-fluorobenzylcarbonyloxy, a p-methoxybenzylcarbonyloxy, a p-nitrobenzylcarbonyloxy, a p-cyanobenzylcarbonyloxy, a 1-naphthoxymethylcarbonyloxy, a 2-naphthoxymethylcarbonyloxy and a pyridylmethyloxycarbonyloxy can be mentioned.

As the $C_{1-6}$ alkylurea group, a methylurea, an ethylurea, a n-propylurea, an i-propylurea, a n-butylurea, an i-butylurea, an s-butylurea, a t-butylurea, a 1-pentylurea, a 2-pentylurea, a 3-pentylurea, an i-pentylurea, a neopentylurea, a t-pentylurea, a 1-hexylurea, a 2-hexylurea, a 3-hexylurea, a 1-methyl-n-pentylurea, a 1,1,2-trimethyl-n-propylurea, a 1,2,2-trimethyl-n-propylurea and a 3,3-dimethyl-n-butylurea, etc. can be mentioned.

As the arylurea group, a phenylurea, an o-methylphenylurea, a p-methylphenylurea, a p-chlorophenylurea, a p-fluorophenylurea, a p-methoxyphenylurea, a p-nitrophenylurea, a p-cyanophenylurea, a 1-naphthylurea and a 2-naphthylurea can be mentioned.

As the aryl $C_{1-6}$ alkylurea group, a benzylurea, an o-methylbenzylurea, a p-methylbenzylurea, a p-chlorobenzylurea, a p-fluorobenzylurea, a p-methoxybenzylurea, a p-nitrobenzylurea, a p-cyanobenzylurea, a 1-naphthylmethylurea, a 2-naphthylmethylurea and a pyridylmethylurea can be mentioned.

As the $C_{1-6}$ alkylthiourea group, a methylthiourea, an ethylthiourea, an n-propylthiourea, an i-propylthiourea, an n-butylthiourea, an i-butylthiourea, an s-butylthiourea, a t-butylthiourea, a 1-pentylthiourea, a 2-pentylthiourea, a 3-pentylthiourea, a i-pentylthiourea, a neopentylthiourea, a t-pentylthiourea, a 1-hexylthiourea, a 2-hexylthiourea, a 3-hexylthiourea, a 1-methyl-n-pentylthourea, a 1,1,2-trimethyl-n-propylthiourea, a 1,2,2-trimethyl-n-propylthiourea and a 3,3-dimethyl-n-butylthiourea can be mentioned.

As the arylthiourea group, a phenylthiourea, an o-methylphenylthiourea, a p-methylphenylthiourea, a p-chlorophenylthiourea, a p-fluorophenylthiourea, a p-methoxyphenylthiourea, a p-nitrophenylthiourea, a p-cyanophenylthiourea, a 1-naphthylthiourea and a 2-naphthylthiourea.

As the aryl $C_{1-6}$ alkylthiourea group, a benzylthiourea, an o-methylbenzylthiourea, a p-methylbenzylthiourea, a p-chlorobenzylthiourea, a p-fluorobenzylthiourea, a p-methoxybenzylthiourea, a p-nitrobenzylthiourea, a p-cyanobenzylthiourea, a 1-naphthylmethylthiourea, a 2-naphthylmethylthiourea and a pyridylmethylthiourea can be mentioned.

As preferable compounds which are used in the present invention, the following compounds are mentioned.

(1)

Chroman derivatives of the formula (I) in which a substituting position of $R^1$ on the chroman ring is at 7- or 8-position, a subsituting position of Z on the chroman ring is at 6-position and a combination of —X—Y—Z— is —C(O)—NH—, —C(O)—NMe—, —C(O)—NH—CH$_2$—, —CH$_2$—NH—, —CH$_2$—NH—CH$_2$—, —SO$_2$—NH— or —NH—C(O)—NH—, or their salts.

(2)

Chroman derivatives or their salts as described in the above item (1), wherein the both of $R^3$ and $R^4$ represent a $C_{1-6}$ alkyl group {said alkyl group is unsubstituted or substituted by a halogen atom, a $C_{1-6}$ alkoxy group or a hydroxyl group}.

(3)

Chroman derivatives or their salts as described in the above item (2), wherein $R^5$ presents a hydroxyl group or forms a bond together with $R^6$.

(4)

Chroman derivatives or their salts as described in the above item (1), wherein $R^7$ and $R^8$ each independently represent a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each is unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$ ($R^2$ represents a halogen atom, a hydroxyl group, a $C_{1-4}$ alkyl group or a $C_{1-4}$ alkoxy group)), a formyl group, a cyano group or a nitro group}, a phenyl group (said phenyl group is unsubtituted or substituted by $R^2$), $R^7$ and $R^8$ together form a 1,4-butylene or a 1,5-pentylene {said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-4}$ alkylcarbonyloxy group}, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ is unsubstituted or substituted by a hydrogen atom, a $C_{1-4}$ alkyl group or a phenyl group (said phenyl group is unsubstituted or substituted by $R^2$))), or $R^7$ and $R^8$, together with the nitrogen atom to which they are bonded, form a pyrrolyl group, a pyrazolyl group, an imidazolyl group, a 1,2,3-triazolyl group, a 1,2,4-triazolyl group or a 1,2,3,4-tetrazolyl group all of which are unsubstituted or substituted by $R^{15}$ ($R^{15}$ has the same meaning as defined in $R^{10}$).

(5)

Chroman derivatives or their salts as described in the above item (3), wherein $R^7$ and $R^8$ each independently represent a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each are unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$ ($R^2$ represents a halogen atom, a hydroxyl group, a $C_{1-4}$ alkyl group or a $C_{1-4}$ alkoxy group)), a formyl group, a cyano group or a nitro group}, a phenyl group (said phenyl group is unsubtituted or substituted by $R^2$), $R^7$ and $R^8$ together form a 1,4-butylene or a 1,5-pentylene {said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-4}$ alkylcarbonyloxy group}, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ represents a hydrogen atom, a $C_{1-4}$ alkyl group or a phenyl group (said phenyl group is unsubstituted or substituted by $R^2$))), or $R^7$ and $R^8$, together with the nitrogen atom to which they are bonded, form a pyrrolyl group, a pyrazolyl group, an imidazolyl group, a 1,2,3-triazolyl group, a 1,2,4-triazolyl group or a 1,2,3,4-tetrazolyl group all of which is unsubstituted or substituted by $R^{15}$ ($R^{15}$ has the same meaning as defined above).

(6)

Chroman derivatives or their salts as described in the above (1), wherein $R^1$ represents a hydrogen atom, a halogen atom, a $C_{1-6}$ alkyl group (said alkyl group is unsubstituted or substituted by a halogen atom, a $C_{1-6}$ alkoxy group or a hydroxyl group), a $C_{1-6}$ alkoxy group (said alkoxy group is unsubstituted or substituted by a halogen atom), a $C_{3-6}$ cycloalkyl group, a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, an aryl $C_{1-6}$ alkylaminocarbonyl group, a di (aryl $C_{1-6}$ alkyl)aminocarbonyl group, a $C_{1-6}$ alkylcarbonyl group, an arylcarbonyl group, an aryl $C_{1-6}$ alkylcarbonyl group, a $C_{1-6}$ alkoxycarbonyl group, an aryloxycarbonyl group, an aryl $C_{1-6}$ alkyloxycarbonyl group, a $C_{1-6}$ alkylcarbonylamino group, an arylcarbonylamino group or an aryl $C_{1-6}$ alkylcarbonylamino group.

(7)

Chroman derivatives or their salts as described in the above (4), wherein $R^1$ represents a hydrogen atom, a halogen atom, a $C_{1-6}$ alkyl group (said alkyl group is unsubstituted or substituted by a halogen atom, a $C_{1-6}$ alkoxy group or a hydroxyl group), a $C_{1-6}$ alkoxy group (said alkoxy group is unsubstituted or substituted by a halogen atom), a $C_{3-6}$ cycloalkyl group, a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, an aryl $C_{1-6}$ alkylaminocarbonyl group, a di (aryl $C_{1-6}$ alkyl)aminocarbonyl group, a $C_{1-6}$ alkylcarbonyl group, an arylcarbonyl group, an aryl $C_{1-6}$ alkylcarbonyl group, a $C_{1-6}$ alkoxycarbonyl group, an aryloxycarbonyl group, an aryl $C_{1-6}$ alkyloxycarbonyl group, a $C_{1-6}$ alkylcarbonylamino group, an arylcarbonylamino group or an aryl $C_{1-6}$ alkylcarbonylamino group.

(8)

Chroman derivatives or their salts as described in the above (5), wherein $R^1$ represents a hydrogen atom, a halogen atom, a $C_{1-6}$ alkyl group (said alkyl group is unsubstituted or substituted by a halogen atom, a $C_{1-6}$ alkoxy group or a hydroxyl group), a $C_{1-6}$ alkoxy group (said alkoxy group is unsubstituted or substituted by a halogen atom), a $C_{3-6}$ cycloalkyl group, a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, an aryl $C_{1-6}$ alkylaminocarbonyl group, a di (aryl $C_{1-6}$ alkyl)aminocarbonyl group, a $C_{1-6}$ alkylcarbonyl group, an arylcarbonyl group, an aryl $C_{1-6}$ alkylcarbonyl group, a $C_{1-6}$ alkoxycarbonyl group, an aryloxycarbonyl group, an aryl $C_{1-6}$ alkyloxycarbonyl group, a $C_{1-6}$ alkylcarbonylamino group, an arylcarbonylamino group or an aryl $C_{1-6}$ alkylcarbonylamino group.

(9)

Chroman derivatives or their salts as described in the above (6), wherein $R^9$ represents a hydrogen atom, a halogen atom, a $C_{1-6}$ alkyl group, a $C_{1-6}$ alkoxy group (said alkoxy group is unsubstituted or substituted by a halogen atom), a hydroxyl group, a nitro group, a cyano group, a formyl group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

(10)

Chroman derivatives or their salts as described in the above (7), wherein $R^9$ represents a hydrogen atom, a halogen atom, a $C_{1-6}$ alkyl group, a $C_{1-6}$ alkoxy group (said alkoxy group is unsubstituted or substituted by a halogen atom), a hydroxyl group, a nitro group, a cyano group, a formyl group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

(11)

Chroman derivatives or their salts as described in the above (8), wherein $R^9$ represents a hydrogen atom, a halogen atom, a $C_{1-6}$ alkyl group, a $C_{1-6}$ alkoxy group (said alkoxy group is unsubstituted or substituted by a halogen atom), a hydroxyl group, a nitro group, a cyano group, a formyl group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

(12)

Chroman derivatives or their salts as described in the above (9), wherein $R^3$ and $R^4$ both represent a methyl group.

(13)

Chroman derivatives or their salts as described in the above (10), wherein $R^3$ and $R^4$ both represent a methyl group.

(14)

Chroman derivatives or their salts as described in the above (11), wherein $R^3$ and $R^4$ both represent a methyl group.

(15)

Chroman derivatives or their salts as described in the above (14), wherein $R^7$ and $R^8$ each independently represent a hydrogen atom, a $C_{1-6}$ alkyl group, a $C_{3-6}$ cycloalkyl group {said alkyl group and cycloalkyl group each are unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$ ($R^2$ represents a halogen atom, a hydroxyl group, a $C_{1-4}$ alkyl group or a $C_{1-4}$ alkoxy group)), a formyl group, a cyano group or a nitro group}, a phenyl group (said phenyl group is unsubstituted or substituted by $R^2$), or $R^7$ and $R^8$ together form a 1,4-butylene or a 1,5-pentylene {said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-4}$ alkylcarbonyloxy group}, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ represent a hydrogen atom, a $C_{1-4}$ alkyl group or a phenyl group (said phenyl group is unsubstituted or substituted by $R^2$))), or $R^7$ and $R^8$, together with the nitrogen atom to which they are bonded, form a pyrrolyl group, a pyrazolyl group or an imidazolyl which is unsubstituted or substituted by $R^{15}$ ($R^{15}$ has the same meaning as defined in $R^{10}$), W represents

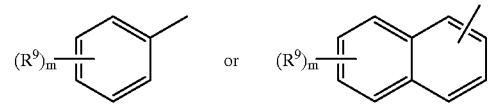

in which $R^9$ represents a hydrogen atom, a halogen atom, a $C_{1-6}$ alkyl group, a $C_{1-6}$ alkoxy group (said alkoxy group is unsubstituted or substituted by a halogen atom), a phenyl group (said phenyl group is unsubstituted or substituted by $R^2$), a hydroxyl group, a nitro group, a cyano group, a formyl group, a formamido group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

(16)

Chroman derivatives and their salts as described in the above (15), wherein $R^1$ represents a hydrogen atom, a halogen atom, a $C_{1-6}$ alkyl group (said alkyl group is unsubstituted or substituted by a halogen atom), a $C_{3-6}$ cycloalkyl group, a nitro group, a cyano group, a formyl group, a carboxyl group, a hydroxyl group, a formamido group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, or a $C_{1-6}$ alkoxycarbonyl group.

(17)

Chroman derivatives or their salts as described in the above (16), wherein $R^7$ and $R^8$ each independently represent a hydrogen atom, a $C_{1-6}$ alkyl group, a $C_{3-6}$ cycloalkyl group, or $R^7$ and $R^8$ together form a 1,4-butylene or a 1,5-pentylene, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ represents a hydrogen atom or a $C_{1-4}$ alkyl group)), or $R^7$ and $R^8$, together with the nitrogen atom to which they are bonded, form a pyrrolyl group or an imidazolyl group.

(18)

Chroman derivatives or their salts as described in the above (17), wherein the combination of X—Y—Z is —C(O)—NH—, —C(O)—NMe— or —NH—C(O)—NH—.

(19)

Chroman derivatives or their salts as described in the above (18), wherein $R^1$ represents a hydrogen atom, a nitro group, a cyano group, a carboxyl group, an amino group, a $C_{1-6}$ alkylamino group, a di $C_{1-6}$ alkylamino group, a $C_{1-6}$ alkylcarbonylamino group, an aryl $C_{1-6}$ alkylcarbonylamino group or a $C_{1-6}$ alkoxycarbonyl group.

(20)

Chroman derivatives or their salts as described in the above (19), wherein $R^1$ represents a nitro group or a cyano group.

(21)

Chroman derivatives or their salts as described in the above (20), wherein $R^7$ represents a $C_{1-6}$ alkyl group or a $C_{3-6}$ cycloalkyl group, $R^8$ represents a hydrogen atom, and $R^7$ and $R^8$ together represent a 1,4-butylene, or $R^7$ and $R^8$, together with the nitrogen atom to which they are bonded, form a pyrrolyl group.

(22)

Chroman derivatives or their salts as described in the above (21), wherein $R^1$ represents a nitro group, and $R^7$ and $R^8$ together with the nitrogen atom to which they are bonded, form a pyrrolyl group, and the combination of X—Y—Z is —C(O)—NH—, and $R^9$ represents a hydrogen atom or a $C_{1-6}$ alkoxy.

(23)

Chroman derivatives or their salts as described in the above (21), wherein $R^1$ represents a nitro group, and $R^7$ and $R^8$ together represent a 1,4-butylene, $R^9$ represents a hydrogen atom, a fluorine atom, a chlorine atom, a methyl group, a methoxy group, an ethoxy group or a nitro group.

(24)

Chroman derivatives or their salts as described in the above (21), wherein $R^1$ represents a nitro group, $R^7$ represents a cyclopropyl group, $R^8$ represents a hydrogen atom, $R^9$ represents a hydrogen atom, a methoxy group, an ethoxy group, a phenyl group, a nitro group, a hydroxyl group, a methylamino group, a dimethylamino group or an acetamido group, and the combination of X—Y—Z is —C(O)—NH—.

(25)

Chroman derivatives or their salts as described in the above (21), wherein $R^1$ represents a nitro group, $R^7$ represents a methyl group or an isopropyl group, $R^8$ represents a hydrogen atom and $R^9$ represents a hydrogen atom, a methoxy group, a phenyl group, a nitro group or an acetamido group.

The concrete examples of the compounds which can be used in the present invention will be shown hereunder. However, the present invention is not to be restricted by them. In the specification, "Me" means methyl group, "Et" means ethyl group, "Pr" means propyl group, "Bu" means butyl group, "Ac" means acetyl group ($COCH_3$) and "—" means a bond.

| $R^1$ | $R^3$ | $R^4$ | $R^5$ | $R^6$ | $R^7$ | $R^8$ | n | X | Y | Z |
|---|---|---|---|---|---|---|---|---|---|---|
| H | Me | Me | OH | H | —$(CH_2)_4$— | | 1 | CO | NH | — |
| F | Me | Me | OH | H | —$(CH_2)_4$— | | 1 | CO | NH | — |
| Br | n-Pr | n-Pr | OH | H | —$(CH_2)_4$— | | 1 | CO | NH | — |
| Me | Me | Me | OH | H | Et | H | 1 | CO | NH | — |
| $CF_3$ | Me | Et | OH | H | —$(CH_2)_4$— | | 2 | CO | NH | $CH_2$ |
| $CH_2CF_3$ | Et | Me | OH | H | —$(CH_2)_4$— | | 1 | CO | NH | — |
| $C_2F_5$ | Me | Me | bond | | Me | H | 1 | CO | NH | — |
| OMe | Me | Me | OH | H | —$(CH_2)_4$— | | 2 | CO | NH | — |
| $OCF_3$ | Me | Me | OH | H | —$(CH_2)_4$— | | 1 | CO | NH | — |
| $CH_2OMe$ | Me | Me | OH | H | —$(CH_2)_4$— | | 1 | CO | NH | — |
| c-Pr | Me | Me | OH | H | —$(CH_2)_4$— | | 3 | CO | NH | — |
| $NO_2$ | Me | Me | OH | H | —$(CH_2)_4$— | | 1 | CO | NH | — |
| CN | Me | Me | OH | H | —$(CH_2)_4$— | | 1 | CO | NH | — |
| CHO | Me | Me | OH | H | —$(CH_2)_4$— | | 1 | $CH_2$ | NH | — |
| $CO_2H$ | Me | Me | OH | H | —$(CH_2)_4$— | | 1 | CO | NH | — |
| OH | Me | Me | OH | H | —$(CH_2)_4$— | | 1 | $CH_2$ | NH | $CH_2$ |
| $CH_2OH$ | Me | Me | bond | | —$(CH_2)_4$— | | 1 | CO | NH | — |
| NHCHO | Me | Me | OH | H | —$(CH_2)_4$— | | 1 | NH | CO | NH |
| NHCN | Me | Me | OH | H | c-Pr | H | 1 | CO | NH | — |
| $NH_2$ | Me | Me | OAc | H | —$(CH_2)_4$— | | 1 | CO | NH | — |
| NHMe | Me | Me | OAc | H | —$(CH_2)_4$— | | 1 | CO | NH | — |
| $NMe_2$ | Me | Me | OAc | H | —$(CH_2)_4$— | | 1 | CO | NH | — |
| NHCOMe | Me | Me | OH | H | —$(CH_2)_4$— | | 1 | CO | NH | $CH_2$ |

-continued

| | | | | | | | | | |
|---|---|---|---|---|---|---|---|---|---|
| NHSO$_2$Me | Me | Me | OH | H | —(CH$_2$)$_4$— | 1 | CO | NH | — |
| CONH$_2$ | Me | Me | OH | H | —(CH$_2$)$_4$— | 4 | CO | NH | — |
| CONHMe | Me | Me | OH | H | —(CH$_2$)$_4$— | 3 | CO | NH | — |
| CONMe$_2$ | Me | Me | OH | H | —(CH$_2$)$_4$— | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | Ac | H | 1 | CO | NH | — |
| CO$_2$CH$_2$Ph | Me | Me | OH | H | —(CH$_2$)$_4$— | 1 | CO | NH | — |

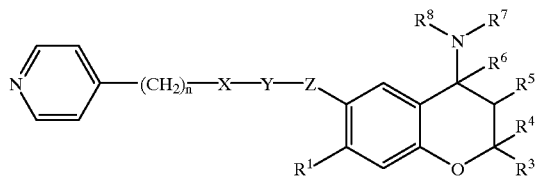

| R$^1$ | R$^3$ | R$^4$ | R$^5$ | R$^6$ | R$^7$ | R$^8$ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | bond | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | bond | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | Ac | H | 1 | CO | NH | — |
| CO$_2$CH$_2$Ph | Me | Me | OH | H | —(CH$_2$)$_4$— | | 1 | CO | NH | — |

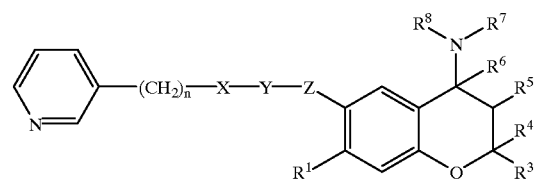

| R$^1$ | R$^3$ | R$^4$ | R$^5$ | R$^6$ | R$^7$ | R$^8$ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | bond | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |

-continued

| R¹ | R³ | R⁴ | R⁵ | R⁶ | R⁷ | R⁸ | n | X | Y | Z |
|---|---|---|---|---|---|---|---|---|---|---|
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | bond | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | Ac | H | 1 | CO | NH | — |
| CO₂CH₂Ph | Me | Me | OH | H | —(CH₂)₄— | | 1 | CO | NH | — |

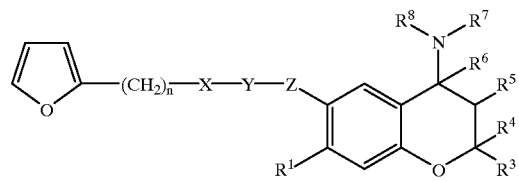

| R¹ | R³ | R⁴ | R⁵ | R⁶ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | bond | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | bond | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | Ac | H | 1 | CO | NH | — |
| CO₂CH₂Ph | Me | Me | OH | H | —(CH₂)₄— | | 1 | CO | NH | — |

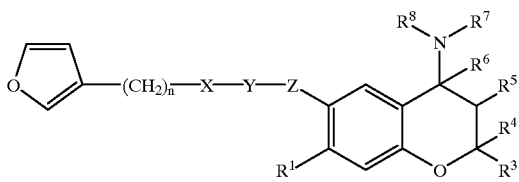

| R¹ | R³ | R⁴ | R⁵ | R⁶ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |

-continued

| | | | | | | | | | | |
|---|---|---|---|---|---|---|---|---|---|---|
| CH$_2$CF$_3$ | Et | Me | OH | H | —(CH$_2$)$_4$— | | 1 | CO | NH | — |
| C$_2$F$_5$ | Me | Me | bond | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | bond | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | Ac | H | 1 | CO | NH | — |
| CO$_2$CH$_2$Ph | Me | Me | OH | H | —(CH$_2$)$_4$— | | 1 | CO | NH | — |

| R$^1$ | R$^3$ | R$^4$ | R$^5$ | R$^6$ | R$^7$ | R$^8$ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | bond | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | bond | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | Ac | H | 1 | CO | NH | — |
| CO$_2$CH$_2$Ph | Me | Me | OH | H | —(CH$_2$)$_4$— | | 1 | CO | NH | — |

-continued

[Structure: thiophene-(CH$_2$)$_n$-X-Y-Z-chromane with R$^1$, R$^3$, R$^4$, R$^5$, R$^6$, R$^7$, R$^8$ substituents]

| R$^1$ | R$^3$ | R$^4$ | R$^5$ | R$^6$ | R$^7$ | R$^8$ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | bond | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | bond | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | Ac | H | 1 | CO | NH | — |
| CO$_2$CH$_2$Ph | Me | Me | OH | H | —(CH$_2$)$_4$— | | 1 | CO | NH | — |

[Structure: pyrrole-(CH$_2$)$_n$-X-Y-Z-chromane with R$^1$, R$^3$, R$^4$, R$^5$, R$^6$, R$^7$, R$^8$ substituents]

| R$^1$ | R$^3$ | R$^4$ | R$^5$ | R$^6$ | R$^7$ | R$^8$ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | bond | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | bond | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |

-continued

| R¹ | R³ | R⁴ | R⁵ | R⁶ | R⁷ | R⁸ | n | X | Y | Z |
|---|---|---|---|---|---|---|---|---|---|---|
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | Ac | H | 1 | CO | NH | — |
| CO₂CH₂Ph | Me | Me | OH | H | —(CH₂)₄— | | 1 | CO | NH | — |

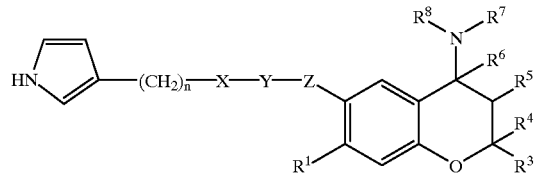

| R¹ | R³ | R⁴ | R⁵ | R⁶ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | bond | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | bond | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | Ac | H | 1 | CO | NH | — |
| CO₂CH₂Ph | Me | Me | OH | H | —(CH₂)₄— | | 1 | CO | NH | — |

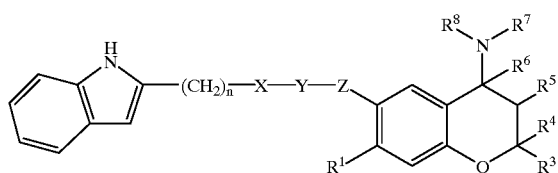

| R¹ | R³ | R⁴ | R⁵ | R⁶ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | bond | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |

-continued

| R¹ | R³ | R⁴ | R⁵ | R⁶ | R⁷ | R⁸ | n | X | Y | Z |
|---|---|---|---|---|---|---|---|---|---|---|
| OH | Me | Me | OH | H | —(CH₂)₄— | | 1 | CH₂ | NH | CH₂ |
| CH₂OH | Me | Me | bond | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | Ac | H | 1 | CO | NH | — |
| CO₂CH₂Ph | Me | Me | OH | H | —(CH₂)₄— | | 1 | CO | NH | — |

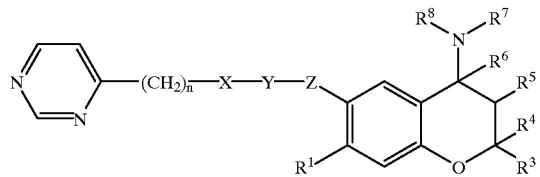

| R¹ | R³ | R⁴ | R⁵ | R⁶ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | bond | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | bond | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | Ac | H | 1 | CO | NH | — |
| CO₂CH₂Ph | Me | Me | OH | H | —(CH₂)₄— | | 1 | CO | NH | — |

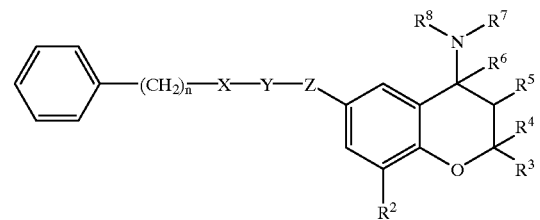

| R² | R³ | R⁴ | R⁵ | R⁶ | R⁷ | R⁸ | n | X | Y | Z |
|---|---|---|---|---|---|---|---|---|---|---|
| H | Et | Et | OH | H | —(CH₂)₄— | | 1 | CO | NH | — |
| F | Me | Me | OH | H | Et | H | 1 | CO | NH | — |
| Br | Me | Me | OH | H | —(CH₂)₄— | | 2 | CO | NH | — |
| Me | Me | Me | OH | H | —(CH₂)₄— | | 1 | CO | NH | — |

-continued

| | | | | | | | | | |
|---|---|---|---|---|---|---|---|---|---|
| CF$_3$ | Me | Me | OH | H | —(CH$_2$)$_4$— | 2 | CO | NH | — |
| CH$_2$CF$_3$ | Me | Me | OH | H | —(CH$_2$)$_4$— | 1 | CO | NH | — |
| C$_2$F$_5$ | Me | Me | OAc | H | —(CH$_2$)$_4$— | 1 | CO | NH | — |
| OMe | Me | Me | OH | H | —(CH$_2$)$_4$— | 1 | CO | NH | CH$_2$ |
| OCF$_3$ | Me | Me | OH | H | —(CH$_2$)$_4$— | 1 | CO | NH | — |
| CH$_2$OMe | Me | Me | OH | H | —(CH$_2$)$_4$— | 1 | CH$_2$ | NH | — |
| c-Pr | Me | Me | OAc | H | —(CH$_2$)$_4$— | 1 | CO | NH | — |
| NO$_2$ | Me | Me | OH | H | —(CH$_2$)$_4$— | 1 | NH | CO | NH |
| CN | Me | Me | OH | H | —(CH$_2$)$_4$— | 1 | CO | NH | — |
| CHO | Me | Me | OH | H | Et | H | 1 | CO | NH | — |
| CO$_2$H | Me | Me | OH | H | —(CH$_2$)$_4$— | 1 | CO | NH | — |
| OH | n-Bu | n-Bu | OH | H | Me | H | 1 | CO | NH | — |
| CH$_2$OH | Me | Me | OH | H | —(CH$_2$)$_4$— | 2 | CO | NH | — |
| NHCHO | Me | Me | OH | H | —(CH$_2$)$_4$— | 3 | CO | NH | — |
| NHCN | Me | Me | OAc | H | —(CH$_2$)$_4$— | 1 | CO | NH | — |
| NH$_2$ | Me | Me | OH | H | c-Pr | H | 1 | CO | NH | — |
| NHMe | Me | Me | OH | H | —(CH$_2$)$_4$— | 4 | CO | NH | — |
| NMe$_2$ | Me | Me | OH | H | —(CH$_2$)$_4$— | 1 | NH | CO | NH |
| NHCOMe | Me | Me | OH | H | —(CH$_2$)$_4$— | 1 | CO | NH | — |
| NHSO$_2$Me | Me | Me | OH | H | —(CH$_2$)$_4$— | 1 | CH$_2$ | NH | CH$_2$ |
| CONH$_2$ | Et | Et | OH | H | —(CH$_2$)$_4$— | 1 | CO | NH | — |
| CONHMe | n-Pr | n-Pr | OH | H | —(CH$_2$)$_4$— | 1 | CO | NH | — |
| CONMe$_2$ | Me | Me | OH | H | n-Bu | H | 1 | CO | NH | — |
| COMe | Me | Me | OH | H | —(CH$_2$)$_4$— | 1 | CO | NH | — |
| CO$_2$Me | Me | Me | OH | H | —(CH$_2$)$_4$— | 1 | CO | NH | — |
| CO$_2$Ph | Me | Me | bond | —(CH$_2$)$_4$— | 1 | CO | NH | — |
| CO$_2$CH$_2$Ph | Me | Me | OH | H | —(CH$_2$)$_4$— | 1 | CO | NH | — |

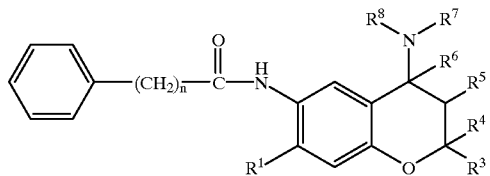

| R$^1$ | R$^3$ | R$^4$ | R$^5$ | R$^6$ | R$^7$ | R$^8$ | n |
|---|---|---|---|---|---|---|---|
| NO$_2$ | Me | Me | OH | H | —(CH$_2$)$_4$— | | 0 |
| NO$_2$ | Me | Me | bond | —(CH$_2$)$_4$— | | 1 |
| NO$_2$ | Me | Me | OH | H | —(CH$_2$)$_4$— | | 2 |
| NO$_2$ | Me | Me | OH | H | Et | H | 3 |
| NO$_2$ | Me | Me | OH | H | i-Pr | H | 4 |
| NO$_2$ | Me | Me | OH | H | —(CH$_2$)$_3$— | | 1 |
| NO$_2$ | Me | Me | OH | H | —(CH$_2$)$_5$— | | 1 |
| CN | Me | Me | OH | H | —(CH$_2$)$_4$— | | 0 |
| CN | Me | Me | bond | —(CH$_2$)$_4$— | | 1 |
| CN | Me | Me | OH | H | —(CH$_2$)$_4$— | | 2 |
| CN | Me | Me | OH | H | Et | H | 3 |
| CN | Me | Me | OH | H | i-Pr | H | 4 |
| NO$_2$ | —(CH$_2$)$_2$— | | OH | H | —(CH#4- | | 1 |
| NO$_2$ | —(CH$_2$)$_3$— | | OH | H | —(CH$_2$)$_4$— | | 1 |
| NO$_2$ | —(CH$_2$)$_4$— | | OH | H | —(CH$_2$)$_4$— | | 1 |
| NO$_2$ | —(CH$_2$)$_5$— | | OH | H | —(CH$_2$)$_4$— | | 1 |
| NO$_2$ | Et | Et | OH | H | c-Pr | H | 0 |
| NO$_2$ | Et | Et | OH | H | —(CH$_2$)$_4$— | | 1 |
| NO$_2$ | Et | Et | OH | H | —(CH$_2$)$_4$— | | 2 |
| NO$_2$ | Et | Et | OH | H | —(CH$_2$)$_4$— | | 3 |
| NO$_2$ | Et | Et | OH | H | —(CH$_2$)$_4$— | | 4 |
| CN | Et | Et | OH | H | —(CH$_2$)$_4$— | | 1 |
| NO$_2$ | n-Pr | n-Pr | OH | H | —(CH$_2$)$_4$— | | 1 |
| CN | n-Pr | n-Pr | OH | H | —(CH$_2$)$_4$— | | 1 |
| NO$_2$ | i-Pr | i-Pr | OH | H | —(CH$_2$)$_4$— | | 1 |
| CN | i-Pr | i-Pr | OH | H | —(CH$_2$)$_4$— | | 1 |
| NO$_2$ | n-Bu | n-Bu | OH | H | —(CH$_2$)$_4$— | | 1 |
| NO$_2$ | i-Bu | i-Bu | OH | H | —(CH$_2$)$_4$— | | 1 |
| NO$_2$ | t-Bu | t-Bu | OH | H | —(CH$_2$)$_4$— | | 1 |
| NO$_2$ | n-Pe | n-Pe | OH | H | —(CH$_2$)$_4$— | | 1 |
| NO$_2$ | n-Hex | n-Hex | OH | H | —(CH$_2$)$_4$— | | 1 |

-continued

| $R^1$ | $R^3$ | $R^4$ | $R^5$ | $R^6$ | $R^7$ | $R^8$ | n | X | Y | Z |
|---|---|---|---|---|---|---|---|---|---|---|
| H | Me | Me | OH | H | —(CH$_2$)$_4$— | | 2 | CO | NH | CH$_2$ |
| F | Me | Me | OH | H | —(CH$_2$)$_4$— | | 2 | CO | NH | CH$_2$ |
| Br | Me | Me | OH | H | Et | H | 2 | CO | NH | CH$_2$ |
| Me | Et | Et | OH | H | —(CH$_2$)$_4$— | | 1 | CO | NH | CH$_2$ |
| CF$_3$ | Me | Me | OH | H | —(CH$_2$)$_4$— | | 1 | CO | NH | — |
| CH$_2$CF$_3$ | Me | Me | bond | | —(CH$_2$)$_4$— | | 1 | CO | NH | CH$_2$ |
| C$_2$F$_5$ | Me | Me | OH | H | —(CH$_2$)$_4$— | | 1 | CO | NH | CH$_2$ |
| OMe | Me | Me | OH | H | —(CH$_2$)$_4$— | | 1 | CO | NH | CH$_2$ |
| OCF$_3$ | Me | Me | OH | H | —(CH$_2$)$_4$— | | 1 | CO | NH | CH$_2$ |
| CH$_2$OMe | Me | Me | OH | H | —(CH$_2$)$_4$— | | 1 | CH$_2$ | NH | — |
| c-Pr | Me | Me | OH | H | n-Pr | H | 1 | CH$_2$ | NH | — |
| NO$_2$ | Me | Me | OH | H | —(CH$_2$)$_4$— | | 1 | CH$_2$ | NH | — |
| CN | Me | Me | OH | H | —(CH$_2$)$_4$— | | 1 | CH$_2$ | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CH$_2$ | NH | — |
| OH | Me | Me | OH | H | —(CH$_2$)$_4$— | | 1 | CO | NH | — |
| CH$_2$OH | Me | Me | OH | H | c-Pr | H | 1 | CH$_2$ | NH | CH$_2$ |
| NHCHO | Me | Me | OH | H | —(CH$_2$)$_4$— | | 2 | CH$_2$ | NH | CH$_2$ |
| NHCN | Me | Me | OH | H | n-Bu | H | 2 | CH$_2$ | NH | CH$_2$ |
| NH$_2$ | Me | Me | OH | H | —(CH$_2$)$_4$— | | 4 | CH$_2$ | NH | CH$_2$ |
| NHMe | Me | Me | OH | H | —(CH$_2$)$_4$— | | 3 | CH$_2$ | NH | CH$_2$ |
| NMe$_2$ | Me | Me | OH | H | —(CH$_2$)$_4$— | | 2 | SO$_2$ | NH | — |
| NHCOMe | Et | Et | OH | H | —(CH$_2$)$_4$— | | 1 | SO$_2$ | NH | — |
| NHSO$_2$Me | Me | Me | OH | H | Ac | H | 1 | SO$_2$ | NH | — |
| CONH$_2$ | Me | Me | bond | | —(CH$_2$)$_4$— | | 1 | SO$_2$ | NH | — |
| CONHMe | Me | Me | OAc | H | —(CH$_2$)$_4$— | | 1 | SO$_2$ | NH | — |
| CONMe$_2$ | Me | Me | OH | H | —(CH$_2$)$_4$— | | 1 | SO$_2$ | NH | — |
| COMe | Me | Me | OH | H | —(CH$_2$)$_4$— | | 1 | NH | CO | NH |
| CO$_2$Me | Me | Me | OH | H | —(CH$_2$)$_4$— | | 1 | NH | CO | NH |
| CO$_2$Ph | Me | Me | OH | H | —(CH$_2$)$_4$— | | 1 | NH | CO | NH |
| CO$_2$CH$_2$Ph | Me | Me | OH | H | —(CH$_2$)$_4$— | | 1 | NH | CO | NH |

| $R^1$ | $R^5$ | $R^6$ | $R^7$ | $R^8$ | n | X | Y | Z |
|---|---|---|---|---|---|---|---|---|
| H | OH | H | H | H | 1 | CO | NH | CH$_2$ |
| F | OH | H | Ph | H | 1 | CO | NH | CH$_2$ |
| Br | bond | | Me | H | 2 | CO | NH | CH$_2$ |
| Me | OH | H | Et | H | 2 | CO | NH | CH$_2$ |
| CF$_3$ | OH | H | n-Pr | H | 1 | CO | NH | CH$_2$ |
| CH$_2$CF$_3$ | OH | H | i-Pr | H | 1 | CO | NH | CH$_2$ |
| C$_2$F$_5$ | OH | H | n-Bu | H | 1 | CO | NH | CH$_2$ |
| OMe | OH | H | t-Bu | H | 1 | CH$_2$ | NH | — |
| OCF$_3$ | OH | H | CH=CH$_2$ | H | 1 | CH$_2$ | NH | — |
| CH$_2$OMe | OH | H | CH$_2$CCH | H | 1 | CH$_2$ | NH | — |
| c-Pr | OH | H | c-Pr | H | 1 | CH$_2$ | NH | — |
| NO$_2$ | OH | H | Et | H | 1 | CH$_2$ | NH | — |
| CN | OH | H | i-Pr | H | 1 | CH$_2$ | NH | — |
| CHO | OH | H | p-MeOPh | H | 1 | CH$_2$ | NH | — |
| CO$_2$H | OH | H | c-Pentyl | H | 1 | CH$_2$ | NH | — |
| OH | OH | H | Ac | H | 4 | CH$_2$ | NH | CH$_2$ |
| CH$_2$OH | OH | H | COEt | H | 2 | CH$_2$ | NH | CH$_2$ |
| NHCHO | OH | H | CO-n-Bu | H | 1 | CH$_2$ | NH | CH$_2$ |
| NHCN | OH | H | COCH$_2$CH$_2$OH | H | 1 | GH$_2$NH | CH$_2$ | |
| NH$_2$ | bond | | COPh | H | 1 | CH$_2$ | NH | CH$_2$ |
| NHMe | bond | | —(CH$_2$)$_5$— | | 1 | SO$_2$ | NH | — |
| NMe$_2$ | OH | H | —(CH$_2$)$_2$O(CH$_2$)$_2$— | | 1 | SO$_2$ | NH | — |
| NHCOMe | OH | H | —(CH$_2$)$_2$NH(CH$_2$)$_2$— | | 1 | SO$_2$ | NH | — |

-continued

| | | | | | | | | |
|---|---|---|---|---|---|---|---|---|
| NHSO$_2$Me | OH | H | —(CH$_2$)$_3$CO— | | 1 | SO$_2$ | NH | — |
| CONH$_2$ | OH | H | —(CH$_2$)$_4$CO— | | 1 | SO$_2$ | NH | — |
| CONHMe | OH | H | Me | H | 1 | NH | CO | NH |
| CONMe$_2$ | OH | H | Et | H | 1 | NH | CO | NH |
| COMe | OH | H | n-Pr | H | 1 | NH | CO | NH |
| CO$_2$Me | OH | H | i-Pr | H | 1 | NH | CO | NH |
| CO$_2$Ph | OH | H | c-Pr | H | 1 | NH | CO | NH |
| CO$_2$CH$_2$Ph | OH | H | i-Bu | H | 1 | NH | CO | NH |

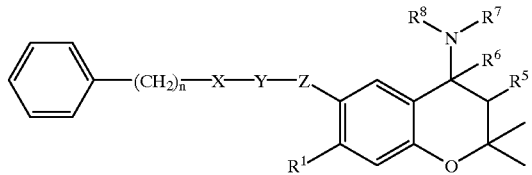

| R$^1$ | R$^5$ | R$^6$ | R$^7$ | R$^8$ | n | X | Y | Z |
|---|---|---|---|---|---|---|---|---|
| H | OH | H | H | H | 0 | NH | CO | NH |
| F | OH | H | Ph | H | 2 | CO | NH | — |
| Br | bond | | Me | H | 2 | CO | NH | — |
| Me | OH | H | Et | H | 3 | CO | NH | — |
| CF$_3$ | OH | H | n-Pr | H | 4 | CO | NH | — |
| CH$_2$CF$_3$ | OH | H | i-Pr | H | 3 | CO | NH | — |
| C$_2$F$_5$ | OH | H | n-Bu | H | 4 | CO | NH | — |
| OMe | OH | H | t-Bu | H | 0 | CO | NH | — |
| OCF$_3$ | OH | H | CH=CH$_2$ | H | 2 | CO | NH | — |
| CH$_2$OMe | OH | H | CH$_2$CCH | H | 2 | CO | NH | — |
| c-Pr | OH | H | c-Pr | H | 0 | CO | NH | — |
| NO$_2$ | OH | H | Et | H | 2 | CO | NH | — |
| CN | OH | H | i-Pr | H | 2 | CO | NH | — |
| CHO | OH | H | p-MeOPh | H | 3 | CO | NH | — |
| CO$_2$H | OH | H | c-Pentyl | H | 4 | CO | NH | — |
| OH | OH | H | Ac | H | 3 | CO | NH | — |
| CH$_2$OH | OH | H | COEt | H | 2 | CO | NH | — |
| NHCHO | OH | H | CO-n-Bu | H | 2 | CO | NH | — |
| NHCN | OH | H | COCH$_2$CH$_2$OH | H | 2 | CO | NH | — |
| NH$_2$ | bond | | COPh | H | 3 | CO | NH | — |
| NHMe | bond | | —(CH$_2$)$_5$— | | 2 | CO | NH | — |
| NMe$_2$ | OH | H | —(CH$_2$)$_2$O(CH$_2$)$_2$— | | 2 | CO | NH | — |
| NHCOMe | OH | H | —(CH$_2$)$_2$NH(CH$_2$)$_2$— | | 3 | CO | NH | — |
| NHSO$_2$Me | OH | H | —(CH$_2$)$_3$CO— | | 2 | CO | NH | — |
| CONH$_2$ | OH | H | —(CH$_2$)$_4$CO— | | 2 | CO | NH | — |
| CONHMe | OH | H | Me | H | 2 | CO | NH | — |
| CONMe$_2$ | OH | H | Et | H | 2 | CO | NH | — |
| COMe | OH | H | n-Pr | H | 2 | CO | NH | — |
| CO$_2$Me | OH | H | i-Pr | H | 2 | CO | NH | — |
| CO$_2$Ph | OH | H | c-Pr | H | 2 | CO | NH | — |
| CO$_2$CH$_2$Ph | OH | H | i-Bu | H | 2 | CO | NH | — |

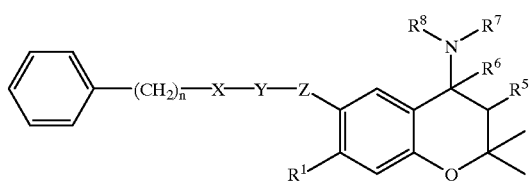

| R$^1$ | R$^5$ | R$^6$ | R$^7$ | R$^8$ | n | X | Y | Z |
|---|---|---|---|---|---|---|---|---|
| H | OH | H | CH=CH$_2$ | H | 1 | CO | NH | — |
| F | OH | H | CH$_2$CCH | H | 1 | CO | NH | — |
| Br | bond | | c-Pr | H | 1 | CO | NH | — |
| Me | OH | H | Et | H | 2 | CO | NH | — |
| CF$_3$ | OH | H | i-Pr | H | 2 | CO | NH | — |
| CH$_2$CF$_3$ | OH | H | p-MeOPh | H | 2 | CO | NH | — |
| C$_2$F$_5$ | OH | H | c-Pentyl | H | 1 | CO | NH | — |
| OMe | OH | H | Ac | H | 1 | CO | NH | — |
| OCF$_3$ | OH | H | COEt | H | 1 | CO | NH | — |
| CH$_2$OMe | OH | H | CO-n-Bu | H | 1 | CO | NH | — |
| c-Pr | OH | H | COCH$_2$CH$_2$OH | H | 1 | CO | NH | — |
| NO$_2$ | OH | H | COPh | H | 1 | CO | NH | — |
| CN | OH | H | Me | H | 1 | CO | NH | — |
| CHO | OH | H | Et | H | 1 | CO | NH | — |

-continued

| | | | | | | | | |
|---|---|---|---|---|---|---|---|---|
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

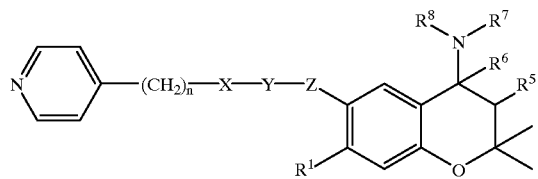

| R¹ | R⁵ | R⁶ | R⁷ | R⁸ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

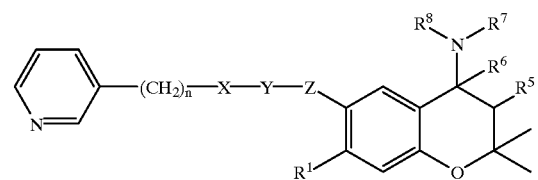

| R¹ | R⁵ | R⁶ | R⁷ | R⁸ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| Me | OH | H | Et | H | 2 | CO | NH | — |

-continued

| R¹ | R⁵ | R⁶ | R⁷ | R⁸ | n | X | Y | Z |
|---|---|---|---|---|---|---|---|---|
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

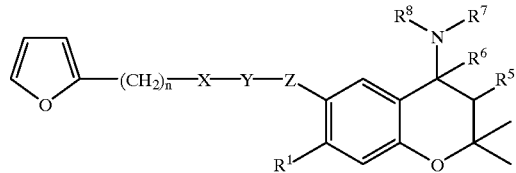

| R¹ | R⁵ | R⁶ | R⁷ | R⁸ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

-continued

Structure: Furan-(CH₂)ₙ-X-Y-Z- attached to chromane with R¹ at 7-position, R⁵ at 3, R⁶ at 4, NR⁷R⁸ at 4-position, with 2,2-dimethyl chromane.

| R¹ | R⁵ | R⁶ | R⁷ | R⁸ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

Structure: Thiophene-(CH₂)ₙ-X-Y-Z- attached to chromane with R¹ at 7-position, R⁵ at 3, R⁶ at 4, NR⁷R⁸ at 4-position, with 2,2-dimethyl chromane.

| R¹ | R⁵ | R⁶ | R⁷ | R⁸ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |

-continued

| | | | | | | | | |
|---|---|---|---|---|---|---|---|---|
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

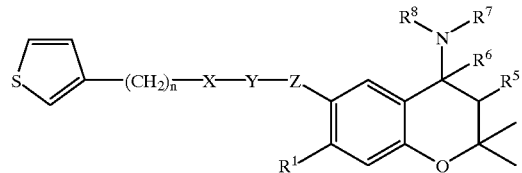

| $R^1$ | $R^5$ | $R^6$ | $R^7$ | $R^8$ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

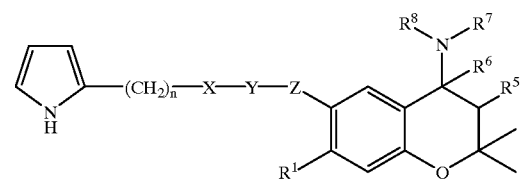

| $R^1$ | $R^5$ | $R^6$ | $R^7$ | $R^8$ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |

-continued

| | | | | | | | | |
|---|---|---|---|---|---|---|---|---|
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

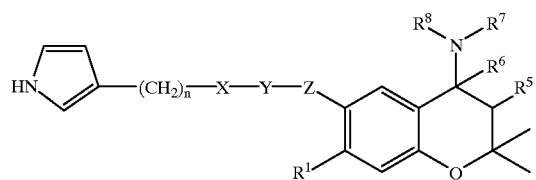

| $R^1$ | $R^5$ | $R^6$ | $R^7$ | $R^8$ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

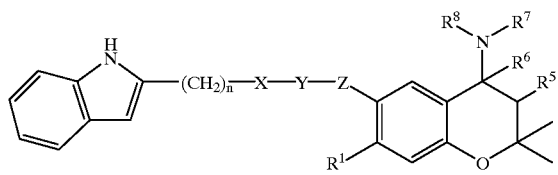

| $R^1$ | $R^5$ | $R^6$ | $R^7$ | $R^8$ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |

-continued

| R¹ | R⁵ | R⁶ | R⁷ | R⁸ | n | X | Y | Z |
|---|---|---|---|---|---|---|---|---|
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

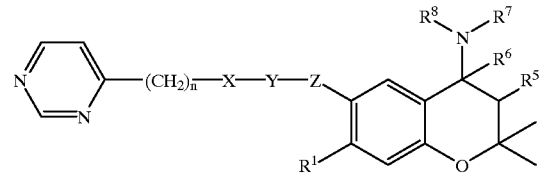

| R¹ | R⁵ | R⁶ | R⁷ | R⁸ | n | X | Y | Z |
|---|---|---|---|---|---|---|---|---|
| H | OH | H | CH=CH₂ | H | 1 | CO | NH | — |
| F | OH | H | CH₂CCH | H | 1 | CO | NH | — |
| Br | bond | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | Ac | H | 1 | CO | NH | — |
| OCF₃ | OH | H | COEt | H | 1 | CO | NH | — |
| CH₂OMe | OH | H | CO-n-Bu | H | 1 | CO | NH | — |
| c-Pr | OH | H | COCH₂CH₂OH | H | 1 | CO | NH | — |
| NO₂ | OH | H | COPh | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | bond | | Ph | H | 1 | CH₂ | NH | — |
| NHMe | bond | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | —(CH₂)₃CO— | | 1 | CO | NH | — |
| CO₂CH₂Ph | OH | H | —(CH₂)₄CO— | | 1 | CO | NH | — |

-continued

Structure: Ph-(CH$_2$)$_n$-C(=O)-NH- attached to a chroman with R$^8$R$^7$N- at position 4, R$^6$, R$^5$, R$^4$, R$^3$, R$^2$ substituents.

| R$^2$ | R$^3$ | R$^4$ | R$^5$ | R$^6$ | R$^7$ | R$^8$ | n |
|---|---|---|---|---|---|---|---|
| NO$_2$ | Me | Me | OH | H | —(CH$_2$)$_4$— | | 0 |
| NO$_2$ | Me | Me | bond | | —(CH$_2$)$_4$— | | 1 |
| NO$_2$ | Me | Me | OH | H | —(CH$_2$)$_4$— | | 2 |
| NO$_2$ | Me | Me | OH | H | —(CH$_2$)$_4$— | | 3 |
| NO$_2$ | Me | Me | OH | H | —(CH$_2$)$_4$— | | 4 |
| NO$_2$ | Me | Me | OH | H | —(CH$_2$)$_3$— | | 1 |
| NO$_2$ | Me | Me | OH | H | —(CH$_2$)$_5$— | | 1 |
| CN | Me | Me | OH | H | —(CH$_2$)$_4$— | | 0 |
| CN | Me | Me | bond | | —(CH$_2$)$_4$— | | 1 |
| CN | Me | Me | OH | H | —(CH$_2$)$_4$— | | 2 |
| CN | Me | Me | OH | H | —(CH$_2$)$_4$— | | 3 |
| CN | Me | Me | OH | H | —(CH$_2$)$_4$— | | 4 |
| NO$_2$ | —(CH$_2$)$_2$— | | OH | H | —(CH$_2$)$_4$— | | 1 |
| NO$_2$ | —(CH$_2$)$_3$— | | OH | H | —(CH$_2$)$_4$— | | 1 |
| NO$_2$ | —(CH$_2$)$_4$— | | OH | H | —(CH$_2$)$_4$— | | 1 |
| NO$_2$ | —(CH$_2$)$_5$— | | OH | H | —(CH$_2$)$_4$— | | 1 |
| NO$_2$ | Et | Et | OH | H | —(CH$_2$)$_4$— | | 0 |
| NO$_2$ | Et | Et | OH | H | —(CH$_2$)$_4$— | | 1 |
| NO$_2$ | Et | Et | OH | H | —(CH$_2$)$_4$— | | 2 |
| NO$_2$ | Et | Et | OH | H | —(CH$_2$)$_4$— | | 3 |
| NO$_2$ | Et | Et | OH | H | —(CH$_2$)$_4$— | | 4 |
| CN | Et | Et | OH | H | —(CH$_2$)$_4$— | | 1 |
| NO$_2$ | n-Pr | n-Pr | OH | H | —(CH$_2$)$_4$— | | 1 |
| CN | n-Pr | n-Pr | OH | H | —(CH$_2$)$_4$— | | 1 |
| NO$_2$ | i-Pr | i-Pr | OH | H | —(CH$_2$)$_4$— | | 1 |
| CN | i-Pr | i-Pr | OH | H | —(CH$_2$)$_4$— | | 1 |
| NO$_2$ | n-Bu | n-Bu | OH | H | —(CH$_2$)$_4$— | | 1 |
| NO$_2$ | i-Bu | i-Bu | OH | H | —(CH$_2$)$_4$— | | 1 |
| NO$_2$ | t-Bu | t-Bu | OH | H | —(CH$_2$)$_4$— | | 1 |
| NO$_2$ | n-Pe | n-Pe | OH | H | —(CH$_2$)$_4$— | | 1 |
| NO$_2$ | n-Hex | n-Hex | OH | H | —(CH$_2$)$_4$— | | 1 |

Structure: Ph-(CH$_2$)$_n$-X-Y-Z- attached to a chroman (with O$_2$N- substituent) having R$^8$R$^7$N-, R$^6$, R$^5$, R$^4$, R$^3$.

| R$^3$ | R$^4$ | R$^5$ | R$^6$ | R$^7$ | R$^8$ | n | X | Y | Z |
|---|---|---|---|---|---|---|---|---|---|
| Me | Me | OH | H | H | H | 4 | CO | NH | — |
| Me | Me | bond | | Ph | H | 3 | CO | NH | — |
| Me | Me | OH | H | Me | H | 1 | CO | NH | — |
| Me | Me | OH | H | Me | Me | 1 | CO | NH | — |
| Me | Me | OH | H | Et | H | 2 | CO | NH | — |
| Me | Me | OH | H | Et | Et | 1 | CO | NH | — |
| Me | Me | OH | H | n-Pr | H | 1 | CO | NH | — |
| Me | Me | OH | H | n-Pr | n-Pr | 1 | CH$_2$ | NH | — |
| Me | Me | bond | | i-Pr | H | 1 | CO | NH | — |
| Me | Me | OH | H | i-Pr | i-Pr | 1 | CO | NH | — |
| Me | Me | OH | H | c-Pr | H | 1 | CO | NH | — |
| Et | Et | OH | H | n-Bu | H | 1 | CO | NH | — |
| Me | Me | OH | H | t-Bu | H | 2 | CO | NH | — |
| Me | Me | OH | H | CH=CH$_2$ | H | 1 | CO | NH | CH$_2$ |
| Me | Me | OH | H | CH$_2$CCH | H | 1 | CO | NH | — |
| Me | Me | OH | H | n-Pentyl | H | 1 | CO | NH | — |
| Me | Me | OH | H | c-Pentyl | H | 1 | CO | NH | — |
| Me | Me | OH | H | n-Hexyl | H | 1 | CO | NH | — |
| Me | Me | OH | H | p-MeOPh | H | 1 | CO | NH | — |
| Me | Me | OH | H | Ac | H | 2 | CO | NH | — |
| Me | Me | OH | H | Ac | Me | 1 | CO | NH | — |

-continued

| | | | | | | | | | |
|---|---|---|---|---|---|---|---|---|---|
| Me | Me | OH | H | Ac | Et | 0 | CO | NH | — |
| Me | Me | OH | H | COEt | H | 1 | CO | NH | — |
| Me | Me | OH | H | CO-n-Bu | H | 1 | CO | NH | — |
| Me | Me | OH | H | COCH$_2$CH$_2$OH | H | 1 | CO | NH | — |
| Me | Me | OH | H | COPh | H | 1 | NH | CO | NH |
| Me | Me | OH | H | COCH$_2$Ph | H | 1 | CO | NH | — |
| Me | Me | OH | H | —(CH$_2$)$_2$O(CH$_2$)$_2$— | | 1 | CO | NH | — |
| Me | Me | OH | H | —(CH$_2$)$_2$NH(CH$_2$)$_2$— | | 1 | CO | NH | — |
| n-Pr | n-Pr | OH | H | —(CH$_2$)$_3$CO— | | 1 | CO | NH | — |
| Me | Me | OH | H | —(CH$_2$)$_4$CO— | | 1 | CO | NH | — |

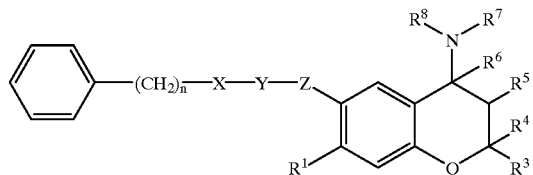

| R$^1$ | R$^3$ | R$^4$ | R$^5$ | R$^6$ | R$^7$ | R$^8$ | n | X | Y | Z |
|---|---|---|---|---|---|---|---|---|---|---|
| CN | Me | Me | OH | H | H | H | 1 | CO | NH | CH$_2$ |
| NO$_2$ | Me | Me | bond | | —(CH$_2$)$_4$— | | 1 | CO | NH | CH$_2$ |
| NO$_2$ | Me | Me | OH | H | Me | H | 1 | CO | NH | CH$_2$ |
| NO$_2$ | H | H | OH | H | Me | Me | 2 | CO | NH | CH$_2$ |
| NO$_2$ | Me | Me | OH | H | Et | H | 1 | CO | NH | CH$_2$ |
| NO$_2$ | Me | Me | OH | H | Et | Et | 1 | CO | NH | CH$_2$ |
| NO$_2$ | Me | Me | OH | H | n-Pr | H | 1 | CO | NH | CH$_2$ |
| NO$_2$ | Me | Me | OH | H | i-Pr | H | 1 | CO | NH | CH$_2$ |
| NO$_2$ | Me | Me | bond | | Me | Me | 1 | CH$_2$ | NH | — |
| NO$_2$ | Me | Me | OH | H | —(CH$_2$)$_4$— | | 1 | CH$_2$ | NH | — |
| NO$_2$ | Me | Me | OH | H | Me | H | 1 | CH$_2$ | NH | — |
| NO$_2$ | Me | Me | OH | H | Et | H | 1 | CH$_2$ | NH | — |
| NO$_2$ | Me | Me | OH | H | n-Pr | H | 1 | CH$_2$ | NH | — |
| NO$_2$ | Me | Me | OH | H | i-Pr | H | 1 | CH$_2$ | NH | — |
| CN | H | H | OH | H | Et | Et | 1 | CH$_2$ | NH | CH$_2$ |
| CN | Me | Me | OH | H | —(CH$_2$)$_4$— | | 1 | CH$_2$ | NH | CH$_2$ |
| CN | Me | Me | OH | H | Me | H | 1 | CH$_2$ | NH | CH$_2$ |
| CN | Me | Me | OH | H | Et | H | 2 | CH$_2$ | NH | OH$_2$ |
| CN | Me | Me | OH | H | n-Pr | H | 2 | CH$_2$ | NH | CH$_2$ |
| CN | Me | Me | OH | H | i-Pr | H | 2 | CH$_2$ | NH | CH$_2$ |
| NO$_2$ | Me | Me | OH | H | Me | Me | 1 | SO$_2$ | NH | — |
| NO$_2$ | Me | Me | OH | H | —(CH$_2$)$_4$— | | 1 | SO$_2$ | NH | — |
| NO$_2$ | Me | Me | OH | H | Me | H | 1 | SO$_2$ | NH | — |
| NO$_2$ | Me | Me | OH | H | Et | H | 1 | SO$_2$ | NH | — |
| NO$_2$ | Me | Me | OH | H | n-Pr | H | 1 | SO$_2$ | NH | — |
| NO$_2$ | Me | Me | OH | H | i-Pr | H | 1 | SO$_2$ | NH | — |
| NO$_2$ | Me | Me | OH | H | —(CH$_2$)$_4$— | | 0 | NH | CO | NH |
| NO$_2$ | Me | Me | OH | H | Me | H | 1 | NH | CO | NH |
| NO$_2$ | Me | Me | OH | H | Et | H | 1 | NH | CO | NH |
| NO$_2$ | Me | Me | OH | H | n-Pr | H | 1 | NH | CO | NH |
| NO$_2$ | Me | Me | OH | H | i-Pr | H | 1 | NH | CO | NH |

| R$^1$ | R$^3$ | R$^4$ | R$^5$ | R$^6$ | R$^7$ | R$^8$ | n | X | Y | Z |
|---|---|---|---|---|---|---|---|---|---|---|
| CN | Me | Me | OH | H | Et | H | 2 | CO | NH | CH$_2$ |
| CN | Me | Me | bond | | —(CH$_2$)$_4$— | | 2 | CO | NH | CH$_2$ |
| CN | Me | Me | OH | H | Me | H | 2 | CO | NH | CH$_2$ |
| CN | Me | Me | OH | H | Me | Me | 2 | CO | NH | CH$_2$ |
| CN | Me | Me | OH | H | Et | H | 3 | CO | NH | CH$_2$ |
| CN | Me | Me | OH | H | Et | Et | 2 | CO | NH | CH$_2$ |
| CN | Me | Me | OH | H | n-Pr | H | 2 | CO | NH | CH$_2$ |
| H | Me | Me | OH | H | i-Pr | H | 2 | CO | NH | CH$_2$ |
| NO$_2$ | H | H | bond | | Me | Me | 2 | CH$_2$ | NH | — |
| NO$_2$ | Me | Me | OH | H | —(CH$_2$)$_4$— | | 2 | CH$_2$ | NH | — |
| NO$_2$ | Me | Me | OH | H | Me | H | 2 | CH$_2$ | NH | — |
| NO$_2$ | Me | Me | OH | H | Et | H | 2 | CH$_2$ | NH | — |

-continued

| R¹ | R³ | R⁴ | R⁵ | R⁶ | R⁷ | R⁸ | n | X | Y | Z |
|---|---|---|---|---|---|---|---|---|---|---|
| NO₂ | Me | Me | OH | H | n-Pr | H | 2 | CH₂ | NH | — |
| NO₂ | Me | Me | OH | H | i-Pr | H | 2 | CH₂ | NH | — |
| NO₂ | H | H | OH | H | Et | Et | 2 | CH₂ | NH | CH₂ |
| NO₂ | Me | Me | OH | H | —(CH₂)₄— | | 2 | CH₂ | NH | CH₂ |
| NO₂ | Me | Me | OH | H | Me | H | 2 | CH₂ | NH | CH₂ |
| NO₂ | Me | Me | OH | H | Et | H | 1 | CH₂ | NH | CH₂ |
| NO₂ | Me | Me | OH | H | n-Pr | H | 1 | CH₂ | NH | CH₂ |
| NO₂ | Me | Me | OH | H | i-Pr | H | 1 | CH₂ | NH | CH₂ |
| NO₂ | Me | Me | OH | H | Me | Me | 2 | SO₂ | NH | — |
| NO₂ | Me | Me | OH | H | —(CH₂)₄— | | 2 | SO₂ | NH | — |
| NO₂ | Me | Me | OH | H | Me | H | 2 | SO₂ | NH | — |
| NO₂ | Me | Me | OH | H | Et | H | 2 | SO₂ | NH | — |
| NO₂ | Me | Me | OH | H | n-Pr | H | 2 | SO₂ | NH | — |
| NO₂ | Me | Me | OH | H | i-Pr | H | 2 | SO₂ | NH | — |
| NO₂ | Me | Me | OH | H | —(CH₂)₄— | | 2 | NH | CO | NH |
| NO₂ | Me | Me | OH | H | Me | H | 2 | NH | CO | NH |
| NO₂ | Me | Me | OH | H | Et | H | 2 | NH | CO | NH |
| NO₂ | Me | Me | OH | H | n-Pr | H | 2 | NH | CO | NH |
| NO₂ | Me | Me | OH | H | i-Pr | H | 2 | NH | CO | NH |

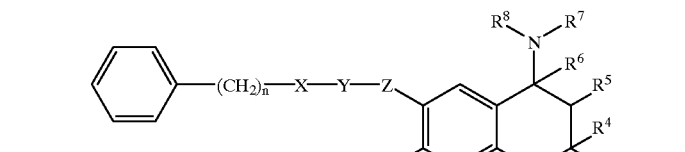

| R¹ | R³ | R⁴ | R⁵ | R⁶ | R⁷ | R⁸ | n | X | Y | Z |
|---|---|---|---|---|---|---|---|---|---|---|
| NO₂ | H | H | OH | H | i-Pr | H | 3 | CO | NH | CH₂ |
| NO₂ | Me | Me | bond | | —(CH₂)₄— | | 3 | CO | NH | CH₂ |
| NO₂ | Me | Me | OH | H | Me | H | 3 | CO | NH | CH₂ |
| CO₂Me | Me | Me | OH | H | Me | Me | 3 | CO | NH | CH₂ |
| NO₂ | Me | Me | OH | H | Et | H | 3 | CO | NH | CH₂ |
| CO₂Me | Me | Me | OH | H | Et | Et | 3 | CO | NH | CH₂ |
| NO₂ | Me | Me | OH | H | n-Pr | H | 3 | CO | NH | CH₂ |
| NO₂ | Me | Me | OH | H | i-Pr | H | 3 | CO | NH | CH₂ |
| CO₂Me | Me | Me | bond | | Me | Me | 3 | CH₂ | NH | — |
| NO₂ | Me | Me | OH | H | —(CH₂)₄— | | 3 | CH₂ | NH | — |
| NO₂ | Me | Me | OH | H | Me | H | 3 | CH₂ | NH | — |
| NO₂ | Me | Me | OH | H | Et | H | 3 | CH₂ | NH | — |
| NO₂ | Me | Me | OH | H | n-Pr | H | 3 | CH₂ | NH | — |
| NO₂ | Me | Me | OH | H | i-Pr | H | 3 | CH₂ | NH | — |
| CO₂Me | Me | Me | OH | H | Et | Et | 4 | CH₂ | NH | CH₂ |
| NO₂ | Me | Me | OH | H | —(CH₂)₄— | | 3 | CH₂ | NH | CH₂ |
| NO₂ | Me | Me | OH | H | Me | H | 3 | CH₂ | NH | CH₂ |
| NO₂ | Me | Me | OH | H | Et | H | 3 | CH₂ | NH | CH₂ |
| NO₂ | Me | Me | OH | H | n-Pr | H | 4 | CH₂ | NH | CH₂ |
| NO₂ | Me | Me | OH | H | i-Pr | H | 3 | CH₂ | NH | CH₂ |
| NO₂ | Me | Me | OH | H | Me | Me | 3 | SO₂ | NH | — |
| CO₂Me | Me | Me | OH | H | —(CH₂)₄— | | 3 | SO₂ | NH | — |
| NO₂ | Me | Me | OH | H | Me | H | 3 | SO₂ | NH | — |
| NO₂ | Me | Me | OH | H | Et | H | 3 | SO₂ | NH | — |
| NO₂ | Me | Me | OH | H | n-Pr | H | 4 | SO₂ | NH | — |
| NO₂ | Me | Me | OH | H | i-Pr | H | 3 | SO₂ | NH | — |
| NO₂ | Me | Me | OH | H | —(CH₂)₄— | | 3 | NH | CO | NH |
| NO₂ | Me | Me | OH | H | Me | H | 3 | NH | CO | NH |
| NO₂ | Me | Me | OH | H | Et | H | 3 | NH | CO | NH |
| CO₂Me | Me | Me | OH | H | n-Pr | H | 4 | NH | CO | NH |
| NO₂ | Me | Me | OH | H | i-Pr | H | 3 | NH | CO | NH |

| R⁵ | R⁶ | R⁷ | R⁸ | n | X | Y | Z |
|---|---|---|---|---|---|---|---|
| OH | H | c-Pr | H | 1 | CO | NH | |
| bond | | Ph | H | 0 | CO | NH | — |
| OH | H | Me | H | 2 | CO | NH | — |

-continued

| | | | | | | | |
|---|---|---|---|---|---|---|---|
| OH | H | Me | Me | 2 | CO | NH | — |
| OH | H | Et | H | 2 | CO | NH | — |
| OH | H | Et | Et | 2 | CO | NH | — |
| OH | H | n-Pr | H | 2 | CO | NH | — |
| OH | H | n-Pr | n-Pr | 2 | CO | NH | — |
| bond | | i-Pr | H | 2 | CO | NH | — |
| OH | H | i-Pr | i-Pr | 2 | CO | NH | — |
| OH | H | c-Pr | H | 2 | CO | NH | — |
| OH | H | n-Bu | H | 2 | CO | NH | — |
| OH | H | t-Bu | H | 2 | CO | NH | — |
| OH | H | CH=CH$_2$ | H | 2 | CO | NH | — |
| OH | H | CH$_2$CCH | H | 2 | CO | NH | — |
| OH | H | n-Pentyl | H | 2 | CO | NH | — |
| OH | H | c-Pentyl | H | 3 | CO | NH | — |
| OH | H | n-Hexyl | H | 3 | CO | NH | — |
| OH | H | p-MeOPh | H | 3 | CO | NH | — |
| OH | H | Ac | H | 2 | CO | NH | — |
| OH | H | Ac | Me | 2 | CO | NH | — |
| OH | H | Ac | Et | 4 | CO | NH | — |
| OH | H | COEt | H | 2 | CO | NH | — |
| OH | H | CO-n-Bu | H | 2 | CO | NH | — |
| OH | H | OOCH$_2$CH$_2$OH | H | 2 | CO | NH | — |
| OH | H | COPh | H | 3 | CO | NH | — |
| OH | H | COCH$_2$Ph | H | 3 | CO | NH | — |
| OH | H | —(CH$_2$)$_2$O(CH$_2$)$_2$— | | 2 | CO | NH | — |
| OH | H | —(CH$_2$)$_2$NH(CH$_2$)$_2$— | | 2 | CO | NH | — |
| OH | H | —(CH$_2$)$_3$CO— | | 2 | CO | NH | — |
| OH | H | —(CH$_2$)$_4$CO— | | 3 | CO | NH | — |

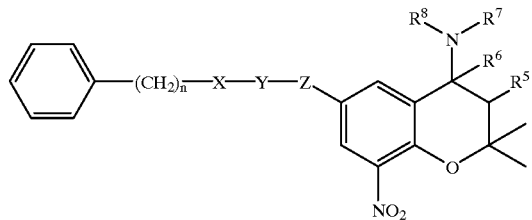

| R$^5$ | R$^6$ | R$^7$ | R$^8$ | n | X | Y | Z |
|---|---|---|---|---|---|---|---|
| OH | H | H | H | 3 | CO | NH | CH$_2$ |
| bond | | —(CH$_2$)$_4$— | | 1 | CO | NH | CH$_2$ |
| OH | H | Me | H | 1 | CO | NH | CH$_2$ |
| OH | H | Me | Me | 1 | CO | NH | CH$_2$ |
| OH | H | Et | H | 1 | CO | NH | CH$_2$ |
| OH | H | Et | Et | 3 | CO | NH | CH$_2$ |
| OH | H | n-Pr | H | 1 | CO | NH | CH$_2$ |
| OH | H | i-Pr | H | 1 | CO | NH | CH$_2$ |
| bond | | Me | Me | 4 | CH$_2$ | NH | — |
| OH | H | —(CH$_2$)$_4$— | | 1 | CH$_2$ | NH | — |
| OH | H | Me | H | 1 | CH$_2$ | NH | — |
| OH | H | Et | H | 1 | CH$_2$ | NH | — |
| OH | H | n-Pr | H | 1 | CH$_2$ | NH | — |
| OH | H | i-Pr | H | 1 | CH$_2$ | NH | — |
| OH | H | Et | Et | 1 | CH$_2$ | NH | CH$_2$ |
| OH | H | —(CH$_2$)$_4$— | | 1 | CH$_2$ | NH | CH$_2$ |
| OH | H | Me | H | 1 | CH$_2$ | NH | CH$_2$ |
| OH | H | Et | H | 1 | CH$_2$ | NH | CH$_2$ |
| OH | H | n-Pr | H | 1 | CH$_2$ | NH | CH$_2$ |
| OH | H | i-Pr | H | 1 | CH$_2$ | NH | CH$_2$ |
| OH | H | Me | Me | 1 | SO$_2$ | NH | — |
| OH | H | —(CH$_2$)$_4$— | | 1 | SO$_2$ | NH | — |
| OH | H | Me | H | 1 | SO$_2$ | NH | — |
| OH | H | Et | H | 1 | SO$_2$ | NH | — |
| OH | H | n-Pr | H | 1 | SO$_2$ | NH | — |
| OH | H | i-Pr | H | 1 | SO$_2$ | NH | — |
| OH | H | —(CH$_2$)$_4$— | | 1 | NH | CO | NH |
| OH | H | Me | H | 1 | NH | CO | NH |
| OH | H | Et | H | 1 | NH | CO | NH |
| OH | H | n-Pr | H | 1 | NH | CO | NH |
| OH | H | i-Pr | H | 1 | NH | CO | NH |

-continued

Structure: (R⁹)ₘ-phenyl-CH₂-C(=O)-NH- attached to a chroman ring bearing O₂N, with R⁵, R⁶, R⁷, R⁸ substituents (NR⁷R⁸ at position 4, R⁶ and R⁵ on the ring, 2,2-dimethyl chroman).

| R⁵ | R⁶ | R⁷ | R⁸ | R⁹ | m |
|---|---|---|---|---|---|
| OH | H | c-Pr | H | p-OEt | 1 |
| OH | H | —(CH₂)₄— | | p-OMe | 1 |
| OH | H | Me | Me | p-OMe | 1 |
| OH | H | Me | Me | m,p-(OMe)₂ | 2 |
| OH | H | Et | H | p-OMe | 1 |
| OH | H | Et | Et | p-OMe | 1 |
| OH | H | c-Pr | H | p-OMe | 1 |
| OH | H | i-Pr | H | p-OMe | 1 |
| OH | H | c-Pr | H | p-OMe | 2 |
| OH | H | —(CH₂)₄— | | m,p-(OMe)₂ | 2 |
| OH | H | Me | H | p-F | 1 |
| OH | H | Et | H | m,p-(OMe)₂ | 2 |
| OH | H | n-Pr | H | p-NHMe | 1 |
| OH | H | i-Pr | H | m,p-(OMe)₂ | 2 |
| OH | H | c-Pr | H | m,p-(OMe)₂ | 2 |
| OH | H | —(CH₂)₄— | | m-OMe | 1 |
| OH | H | c-Pr | H | m-OMe | 1 |
| OH | H | Et | H | m-OMe | 1 |
| OH | H | c-Pr | H | o-OMe | 1 |
| OH | H | i-Pr | H | m-OMe | 1 |
| OH | H | c-Pr | H | p-NO₂ | 1 |
| OH | H | —(CH₂)₄— | | p-CN | 1 |
| OH | H | Me | H | p-NMe₂ | 1 |
| bond | | Et | H | p-Me | 1 |
| OH | H | c-Pr | H | p-OH | 1 |
| OH | H | i-Pr | H | p-Cl | 1 |
| OH | H | —(CH₂)₄— | | p-Ac | 1 |
| OH | H | Me | H | p-CO₂Me | 1 |
| OH | H | Et | H | p-NHAc | 1 |
| OH | H | c-Pr | H | p-NHAc | 1 |
| OH | H | i-Pr | H | p-NHAc | 1 |

Structure: (R⁹)ₘ-phenyl-CH₂-X-Y-Z- attached to a chroman ring bearing O₂N, with R⁵, R⁶, R⁷, R⁸ substituents.

| R⁵ | R⁶ | R⁷ | R⁸ | R⁹ | m | X | Y | Z |
|---|---|---|---|---|---|---|---|---|
| OH | H | Et | H | p-OMe | 1 | CO | NMe | — |
| OH | H | c-Pr | H | m,p-OCH₂O— | 1 | CO | NH | — |
| OH | H | Me | H | p-OMe | 1 | CO | NH | CH₂ |
| OH | H | Me | Me | p-F | 1 | CO | NH | CH₂ |
| OH | H | Et | H | p-OMe | 1 | CO | NH | CH₂ |
| OH | H | Et | Et | p-Me | 1 | CO | NH | CH₂ |
| OH | H | n-Pr | H | m,p-(OMe)₂ | 2 | CO | NH | CH₂ |
| OH | H | i-Pr | H | p-OMe | 1 | CO | NH | CH₂ |
| bond | | Me | Me | p-Br | 1 | CH₂ | NH | — |
| OH | H | —(CH₂)₄— | | m,p-(OMe)₂ | 2 | CH₂ | NH | — |
| OH | H | Me | H | m,p-Me₃ | 3 | CH₂ | NH | — |
| OH | H | Et | H | m,p-(OMe)₂ | 2 | CH₂ | NH | — |
| OH | H | n-Pr | H | p-NMe₂ | 1 | CH₂ | NH | — |
| OH | H | c-Pr | H | p-OMe | 1 | CH₂ | NH | — |
| OH | H | Et | Et | p-NHMe | 1 | CH₂ | NH | CH₂ |
| OH | H | —(CH₂)₄— | | m-OMe | 1 | CH₂ | NH | CH₂ |
| OH | H | Me | H | p-NH₂ | 1 | CH₂ | NH | CH₂ |
| OH | H | Et | H | p-NHCONH₂ | 1 | CH₂ | NH | CH₂ |
| OH | H | n-Pr | H | p-CN | 1 | CH₂ | NH | CH₂ |
| OH | H | i-Pr | H | p-NO₂ | 1 | CH₂ | NH | CH₂ |
| OH | H | Me | Me | p-Ac | 1 | SO₂ | NH | — |
| OH | H | —(CH₂)₄— | | p-CO₂Me | 1 | SO₂ | NH | — |
| OH | H | Me | H | p-CONH₂ | 1 | SO₂ | NH | — |

-continued

| | | | | | | | | |
|---|---|---|---|---|---|---|---|---|
| OH | H | Et | H | p-COPh | 1 | SO₂ | NH | — |
| OH | H | n-Pr | H | p-NHAc | 1 | SO₂ | NH | — |
| OH | H | i-Pr | H | p-CF₃ | 1 | SO₂ | NH | — |
| OH | H | —(CH₂)₄— | | p-OMe | 1 | NH | CO | NH |
| OH | H | Me | H | p-OMe | 1 | NH | CO | NH |
| OH | H | Et | H | m,p-(OMe)₂ | 2 | NH | CO | NH |
| OH | H | n-Pr | H | p-OCF₃ | 1 | NH | CO | NH |
| OH | H | i-Pr | H | p-OMe | 1 | NH | CO | NH |

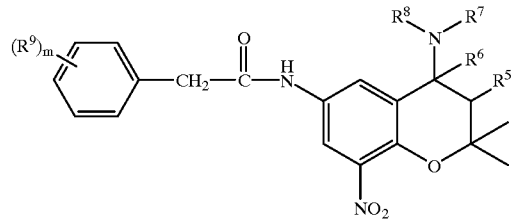

| R⁵ | R⁶ | R⁷ | R⁸ | R⁹ | m |
|---|---|---|---|---|---|
| OH | H | H | H | p-Cl | 1 |
| bond | | —(CH₂)₄— | | p-OMe | 1 |
| OH | H | Me | H | p-OMe | 1 |
| OH | H | Me | Me | m,p-(OMe)₂ | 2 |
| OH | H | Et | H | p-OMe | 1 |
| OH | H | Et | Et | p-OMe | 1 |
| OH | H | n-Pr | H | p-OMe | 1 |
| OH | H | i-Pr | H | p-OMe | 1 |
| bond | | Me | Me | p-OMe | 1 |
| OH | H | —(CH₂)₄— | | m,p-(OMe)₂ | 2 |
| OH | H | Me | H | p-F | 1 |
| OH | H | Et | H | m,p-(OMe)₂ | 2 |
| OH | H | n-Pr | H | p-NHMe | 1 |
| OH | H | i-Pr | H | m,p-(OMe)₂ | 2 |
| OH | H | c-Pr | H | m,p-(OMe)₂ | 2 |
| OH | H | —(CH₂)₄— | | m-OMe | 1 |
| OH | H | Me | H | m-OMe | 1 |
| OH | H | Et | H | m-OMe | 1 |
| OH | H | n-Pr | H | o-OMe | 1 |
| OH | H | i-Pr | H | m-OMe | 1 |
| OH | H | Me | Me | p-NO₂ | 1 |
| OH | H | —(CH₂)₄— | | p-CN | 1 |
| OH | H | Me | H | p-NMe₂ | 1 |
| OH | H | Et | H | p-Me | 1 |
| OH | H | n-Pr | H | p-Cl | 1 |
| OH | H | i-Pr | H | p-Cl | 1 |
| OH | H | —(CH₂)₄— | | p-Ac | 1 |
| OH | H | Me | H | p-CO₂Me | 1 |
| OH | H | Et | H | p-NHCONH₂ | 1 |
| OH | H | n-Pr | H | p-NHAc | 1 |
| OH | H | i-Pr | H | p-NHCONH₂ | 1 |

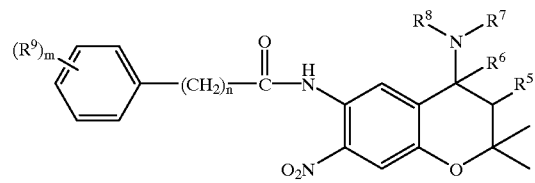

| R⁵ | R⁶ | R⁷ | R⁸ | R⁹ | m | n |
|---|---|---|---|---|---|---|
| OH | H | H | H | p-Cl | 1 | 2 |
| bond | | —(CH₂)₄— | | p-OMe | 1 | 2 |
| OH | H | Me | H | p-OMe | 1 | 2 |
| OH | H | i-Pr | H | m,p-(OMe)₂ | 2 | 1 |
| OH | H | Et | H | p-OMe | 1 | 2 |
| OH | H | c-Pr | H | p-OMe | 1 | 2 |
| OH | H | —(CH₂)₄— | | p-OMe | 1 | 2 |
| OH | H | i-Pr | H | p-OMe | 1 | 2 |
| bond | | Me | Me | p-OMe | 1 | 2 |
| OH | H | —(CH₂)₄— | | m,p-(OMe)₂ | 2 | 2 |
| OH | H | —(CH₂)₄— | | p-F | 1 | 1 |
| OH | H | Et | H | m,p-(OMe)₂ | 2 | 2 |

-continued

| | | | | | | |
|---|---|---|---|---|---|---|
| OH | H | n-Pr | H | p-NHMe | 1 | 2 |
| OH | H | i-Pr | H | m,p-(OMe)$_2$ | 2 | 2 |
| OH | H | c-Pr | H | m,p-(OMe)$_2$ | 2 | 2 |
| OH | H | —(CH$_2$)$_4$— | | m-OMe | 1 | 2 |
| OH | H | Me | H | m-OMe | 1 | 3 |
| OH | H | Et | H | m-OMe | 1 | 2 |
| OH | H | n-Pr | H | o-OMe | 1 | 4 |
| OH | H | i-Pr | H | m-OMe | 1 | 2 |
| OH | H | —(CH$_2$)$_4$— | | p-NO$_2$ | 1 | 1 |
| OH | H | —(CH$_2$)$_4$— | | p-CN | 1 | 2 |
| OH | H | c-Pr | H | p-NMe$_2$ | 1 | 1 |
| OH | H | —(CH$_2$)$_4$— | | p-Me | 1 | 1 |
| OH | H | —(CH$_2$)$_4$— | | p-Cl | 1 | 1 |
| OH | H | c-Pr | H | p-Ph | 1 | 1 |
| OH | H | —(CH$_2$)$_4$— | | p-Ac | 1 | 4 |
| OH | H | Me | H | p-CO$_2$Me | 1 | 2 |
| OH | H | i-Pr | H | p-NO$_2$ | 1 | 1 |
| OH | H | n-Pr | H | p-NHAc | 1 | 2 |
| OH | H | i-Pr | H | p-NHCONH$_2$ | 1 | 2 |

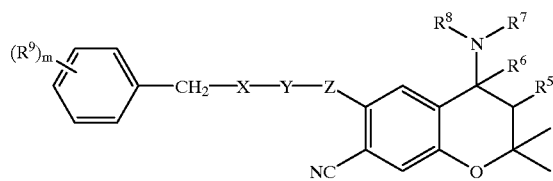

| R$^5$ | R$^6$ | R$^7$ | R$^8$ | R$^9$ | m | X | Y | Z |
|---|---|---|---|---|---|---|---|---|
| OH | H | H | H | p-Cl | 1 | CO | NH | CH$_2$ |
| bond | | —(CH$_2$)$_4$— | | p-OMe | 1 | CO | NH | CH$_2$ |
| OH | H | Me | H | p-OMe | 1 | CO | NH | CH$_2$ |
| OH | H | Me | Me | p-F | 1 | CO | NH | CH$_2$ |
| OH | H | Et | H | p-OMe | 1 | CO | NH | CH$_2$ |
| OH | H | Et | Et | p-Me | 1 | CO | NH | CH$_2$ |
| OH | H | n-Pr | H | m,p-(OMe)$_2$ | 2 | CO | NH | CH$_2$ |
| OH | H | i-Pr | H | p-OMe | 1 | CO | NH | CH$_2$ |
| bond | | Me | Me | p-Br | 1 | CH$_2$ | NH | — |
| OH | H | —(CH$_2$)$_4$— | | m,p-(OMe)$_2$ | 2 | CH$_2$ | NH | — |
| OH | H | Me | H | m,p-Me$_3$ | 3 | CH$_2$ | NH | — |
| OH | H | Et | H | m,p-(OMe)$_2$ | 2 | CH$_2$ | NH | — |
| OH | H | n-Pr | H | p-NMe$_2$ | 1 | CH$_2$ | NH | — |
| OH | H | i-Pr | H | p-t-Bu | 1 | CH$_2$ | NH | — |
| OH | H | Et | Et | p-NHMe | 1 | CH$_2$ | NH | CH$_2$ |
| OH | H | —(CH$_2$)$_4$— | | mOMe | 1 | CH$_2$ | NH | CH$_2$ |
| OH | H | Me | H | p-NH$_2$ | 1 | CH$_2$ | NH | CH$_2$ |
| OH | H | Et | H | p-NHCONH$_2$ | 1 | CH$_2$ | NH | CH$_2$ |
| OH | H | n-Pr | H | p-CN | 1 | CH$_2$ | NH | CH$_2$ |
| OH | H | i-Pr | H | p-NO$_2$ | 1 | CH$_2$ | NH | CH$_2$ |
| OH | H | Me | Me | p-Ac | 1 | SO$_2$ | NH | — |
| OH | H | —(CH$_2$)$_4$— | | p-CO$_2$Me | 1 | SO$_2$ | NH | — |
| OH | H | Me | H | p-CONH$_2$ | 1 | SO$_2$ | NH | — |
| OH | H | Et | H | p-COPh | 1 | SO$_2$ | NH | — |
| OH | H | n-Pr | H | p-NHAc | 1 | SO$_2$ | NH | — |
| OH | H | i-Pr | H | p-CF$_3$ | 1 | SO$_2$ | NH | — |
| OH | H | —(CH$_2$)$_4$— | | p-OMe | 1 | NH | CO | NH |
| OH | H | Me | H | p-OMe | 1 | NH | CO | NH |
| OH | H | Et | H | m,p-(OMe)$_2$ | 2 | NH | CO | NH |
| OH | H | n-Pr | H | p-OCF$_3$ | 1 | NH | CO | NH |
| OH | H | i-Pr | H | p-OMe | 1 | NH | CO | NH |

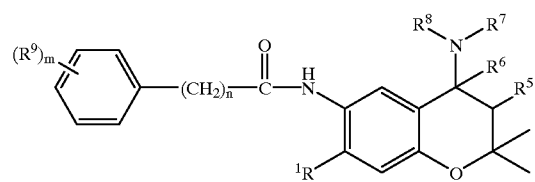

| R$^1$ | R$^5$ | R$^6$ | R$^7$ | R$^8$ | R$^9$ | m | n |
|---|---|---|---|---|---|---|---|
| NO$_2$ | OH | H | c-Pr | H | m-Ph | 1 | 1 |
| CO$_2$Me | bond | | —(CH$_2$)$_4$— | | p-OMe | 1 | 2 |
| CO$_2$Me | OH | H | Me | H | p-OMe | 1 | 1 |

-continued

| | | | | | | | |
|---|---|---|---|---|---|---|---|
| CO₂Et | OH | H | Me | Me | p-F | 1 | 1 |
| CO₂Me | OH | H | Et | H | p-OMe | 1 | 1 |
| NO₂ | OH | H | c-Pr | H | o-Ph | 1 | 1 |
| CO₂Me | OH | H | n-Pr | H | m,p-(OMe)₂ | 2 | 1 |
| CO₂Me | OH | H | i-Pr | H | p-OMe | 1 | 1 |
| NO₂ | OH | H | Et | H | p-NO₂ | 1 | 1 |
| CO₂Et | OH | H | —(CH₂)₄— | | m,p-(OMe)₂ | 2 | 1 |
| CO₂Me | OH | H | Me | H | m,p-Me₃ | 3 | 1 |
| CO₂Me | OH | H | Et | H | m,p-(OMe)₂ | 2 | 1 |
| CO₂Et | OH | H | n-Pr | H | p-NMe₂ | 1 | 1 |
| CO₂Et | OH | H | i-Pr | H | p-t-Bu | 1 | 2 |
| CO₂Et | OH | H | Et | Et | p-NHMe | 1 | 1 |
| CO₂H | OH | H | —(CH₂)₄— | | m-OMe | 1 | 1 |
| CO₂H | OH | H | Me | H | p-NH₂ | 1 | 1 |
| CO₂H | OH | H | Et | H | p-NHCONH₂ | 1 | 1 |
| Ac | OH | H | n-Pr | H | p-CN | 1 | 1 |
| CO₂H | OH | H | i-Pr | H | p-NO₂ | 1 | 1 |
| CO₂H | OH | H | Me | Me | p-Ac | 1 | 3 |
| Ac | OH | H | —(CH₂)₄— | | p-CO₂Me | 1 | 1 |
| Ac | OH | H | Me | H | p-CONH₂ | 1 | 1 |
| Ac | OH | H | Et | H | p-COPh | 1 | 1 |
| Ac | OH | H | n-Pr | H | p-NHAc | 1 | 1 |
| Ac | OH | H | i-Pr | H | p-CF₃ | 1 | 4 |
| Ac | OH | H | —(CH₂)₄— | | p-OMe | 1 | 1 |
| CO₂Me | OH | H | Me | H | p-OMe | 1 | 1 |
| CO₂Me | OH | H | Et | H | m,p-(OMe)₂ | 2 | 1 |
| CO₂Me | OH | H | n-Pr | H | p-OCF₃ | 1 | 1 |
| CO₂Me | OH | H | i-Pr | H | p-OMe | 1 | 1 |

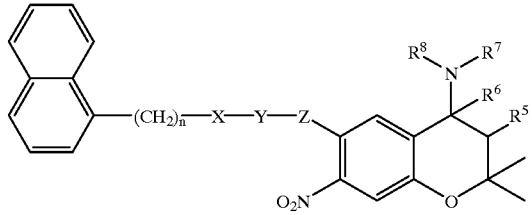

| R⁵ | R⁶ | R⁷ | R⁸ | n | X | Y | Z |
|---|---|---|---|---|---|---|---|
| OH | H | c-Pr | H | 1 | CO | NH | — |
| bond | | Ph | H | 0 | CO | NH | — |
| OH | H | i-Pr | H | 1 | CO | NH | — |
| OH | H | Me | Me | 1 | CO | NH | — |
| OH | H | Et | H | 1 | CO | NH | — |
| OH | H | Et | Et | 1 | CO | NH | — |
| OH | H | n-Pr | H | 1 | CO | NH | — |
| OH | H | n-Pr | n-Pr | 1 | CO | NH | — |
| bond | | i-Pr | H | 1 | CO | NH | — |
| OH | H | i-Pr | i-Pr | 1 | CO | NH | — |
| OH | H | c-Pr | H | 2 | CO | NH | — |
| OH | H | n-Bu | H | 1 | CO | NH | — |
| OH | H | t-Bu | H | 1 | CO | NH | — |
| OH | H | CH=CH₂ | H | 1 | CO | NH | — |
| OH | H | CH₂CCH | H | 1 | CO | NH | — |
| OH | H | n-Pentyl | H | 2 | CO | NH | — |
| OH | H | c-Pentyl | H | 3 | CO | NH | — |
| OH | H | n-Hexyl | H | 3 | CO | NH | — |
| OH | H | p-MeOPh | H | 3 | CO | NH | — |
| OH | H | Ac | H | 2 | CO | NH | — |
| OH | H | Ac | Me | 2 | CO | NH | — |
| OH | H | Ac | Et | 4 | CO | NH | — |
| OH | H | COEt | H | 2 | CO | NH | — |
| OH | H | CO-n-Bu | H | 2 | CO | NH | — |
| OH | H | COCH₂CH₂OH | H | 2 | CO | NH | — |
| OH | H | COPh | H | 3 | CO | NH | — |
| OH | H | COCH₂Ph | H | 3 | CO | NH | — |
| OH | H | —(CH₂)₂O(CH₂)₂— | | 2 | CO | NH | — |
| OH | H | —(CH₂)₂NH(CH₂)₂— | | 2 | CO | NH | — |
| OH | H | —(CH₂)₃CO— | | 2 | CO | NH | — |
| OH | H | —(CH₂)₄CO— | | | CO | NH | — |

-continued

[Structure: naphthalene-(CH2)n-X-Y-Z-chroman with O2N, R8R7N, R6, R5, and 2,2-dimethyl substituents]

| R5 | R6 | R7 | R8 | n | X | Y | Z |
|---|---|---|---|---|---|---|---|
| OH | H | c-Pr | H | 1 | CO | NH | — |
| bond | | Ph | H | 0 | CO | NH | — |
| OH | H | i-Pr | H | 1 | CO | NH | — |
| OH | H | Me | Me | 1 | CO | NH | — |
| OH | H | Et | H | 1 | CO | NH | — |
| OH | H | Et | Et | 1 | CO | NH | — |
| OH | H | n-Pr | H | 1 | CO | NH | — |
| OH | H | n-Pr | n-Pr | 1 | CO | NH | — |
| bond | | i-Pr | H | 1 | CO | NH | — |
| OH | H | i-Pr | i-Pr | 1 | CO | NH | — |
| OH | H | c-Pr | H | 2 | CO | NH | — |
| OH | H | n-Bu | H | 1 | CO | NH | — |
| OH | H | t-Bu | H | 1 | CO | NH | — |
| OH | H | CH=CH2 | H | 1 | CO | NH | — |
| OH | H | CH2CCH | H | 1 | CO | NH | — |
| OH | H | n-Pentyl | H | 2 | CO | NH | — |
| OH | H | c-Pentyl | H | 3 | CO | NH | — |
| OH | H | n-Hexyl | H | 3 | CO | NH | — |
| OH | H | p-MeOPh | H | 3 | CO | NH | — |
| OH | H | Ac | H | 2 | CO | NH | — |
| OH | H | Ac | Me | 2 | CO | NH | — |
| OH | H | Ac | Et | 4 | CO | NH | — |
| OH | H | COEt | H | 2 | CO | NH | — |
| OH | H | CO-n-Bu | H | 2 | CO | NH | — |
| OH | H | COCH2CH2OH | H | 2 | CO | NH | — |
| OH | H | COPh | H | 3 | CO | NH | — |
| OH | H | COCH2Ph | H | 3 | CO | NH | — |
| OH | H | —(CH2)2O(CH2)2— | | 2 | CO | NH | — |
| OH | H | —(CH2)2NH(CH2)2— | | 2 | CO | NH | — |
| OH | H | —(CH2)3CO— | | 2 | CO | NH | — |
| OH | H | —(CH2)4CO— | | 3 | CO | NH | — |

The compounds of the present invention have asymmetric carbon atoms at the 3-position and 4-position in the pyran ring and therefore, include optically active compounds based on the asymmetric carbon atoms. Such optically active compounds may be used in the present invention, like the racemic modifications. In addition, cis- or trans-isomers based on the sterorconfiguration at the 3-position and 4-position in the pyran ring are included. It is preferable to use the trans-isomers. If the compounds may form salts, their pharmaceutically acceptable salts may be used as the active ingredients of the present invention.

The methods for producing the compounds of the present invention will be explained.

Of the compounds of the formula (I), as shown in the following reaction scheme, compounds in which $R^7$ and $R^8$ each independently represent a hydrogen atom, a $C_{1-6}$ alkyl group, a $C_{2-6}$ alkenyl group, a $C_{2-6}$ alkynyl group, a $C_{3-6}$ cycloalkyl group or a phenyl group, or $R^7$ and $R^8$ together form a 1,4-butylene or a 1,5-pentylene, or $R^7$ and $R^8$ together represent $(CH_2)_t X^1 (CH_2)_p$ are obtained by reacting a compound of the formula (2) and a compound of the formula (3) in an inert solvent.

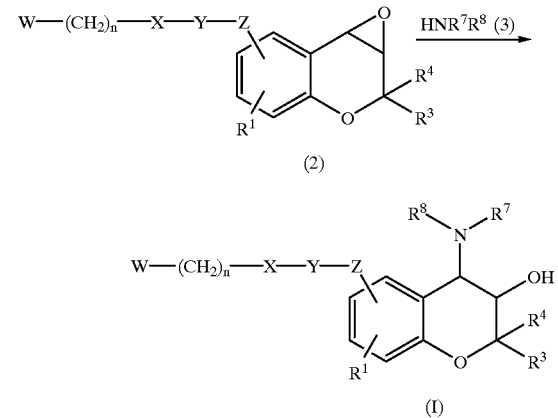

As the solvent used for the reaction of the compound of the formula (2) with the compound of the formula (3), the following solvents are exemplified.

Such solvents are sulfonixde solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, alcohol solvents such as methanol, ethanol or propanol. Further, the reaction can be conducted in the absence of a solvent. Of these, alcohol solvents are preferable.

The reaction temperature in this reaction is, usually, from −20° C. to a reflux temperature for the reaction solvent used, preferably, from 60° C. to 100° C.

Regarding molar ratio of the reaction materials, the ratio of the compound (3)/the compound (2) is within the range of from 0.5 to 4.0, preferably, 1.0 to 2.0.

Compounds in which both $R^7$ and $R^8$ are not a hydrogen atom can be obtained by reacting a compound (6) which is obtained by deprotecting an acetyl group of a compound (5) (the compound (5) can be synthesized by known methods described in, e.g., J. M. Evans et al., J. Med. Chem. 1984, 27, 1127, J. Med. Chem. 1986, 29, 2194, J. T. North et al., J. Org. Chem. 1995, 60, 3397, Japanese Patent Application Laid-open No. Sho 56-57785, Japanese Patent Application Laid-open No. Sho 56-57786 and Japanese Patent Application Laid-open No. Sho 58-188880) with an acid chloride (7) in the presence of a base, or reacting the compound (6) with a carboxlyic acid (8) by using a condensation agent.

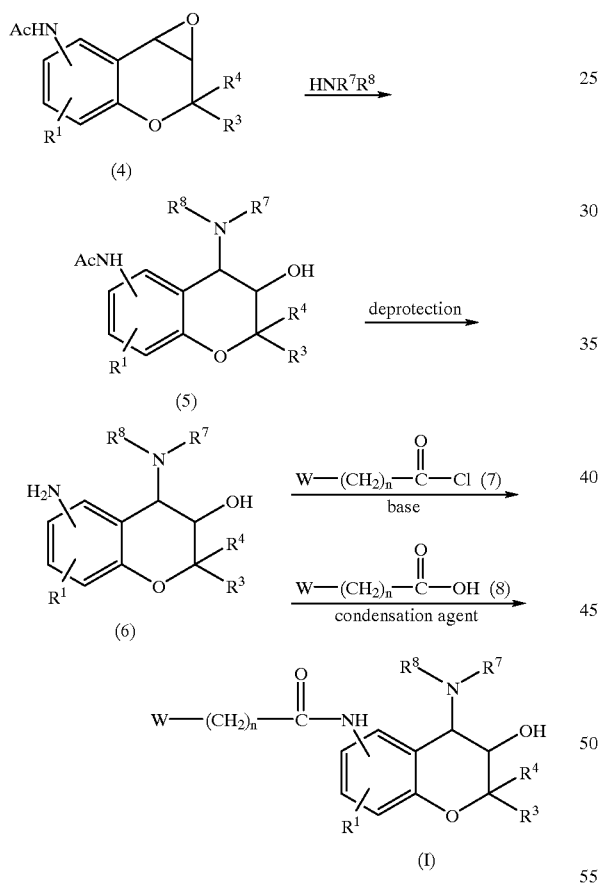

Of the compounds of the formula (2), a compound (12) in which X represents C=O, Y represents NH and Z means a bond can be synthesized by known methods described by J. M. Evans et al., J. Med. Chem. 1984, 27, 1127, J. Med. Chem. 1986, 29, 2194, J. T. North et al., Org. Chem. 1995, 60, 3397, Japanese Patent Application Laid-open No. Sho 56-57785, Japanese Patent Application Laid-open No. Sho 56-57786 and Japanese Patent Application Laid-open No. Sho 58-188880).

Namely, the compound (12) can be obtained by the process that a compound (9) is reacted with the acid chloride (7) in the presence of a base or the compound (9) is reacted with the carboxylic acid (8) by using a condensation agent to obtain a compound (10), and the obtained compound (10) is rendered to a bromohydrin (11) by N-bromosuccinic acid imide, and then, the bromohydrin is subject to an epoxidation in the presence of a base. The compound (10) may be directly subjected to an epoxidation by using a peroxide.

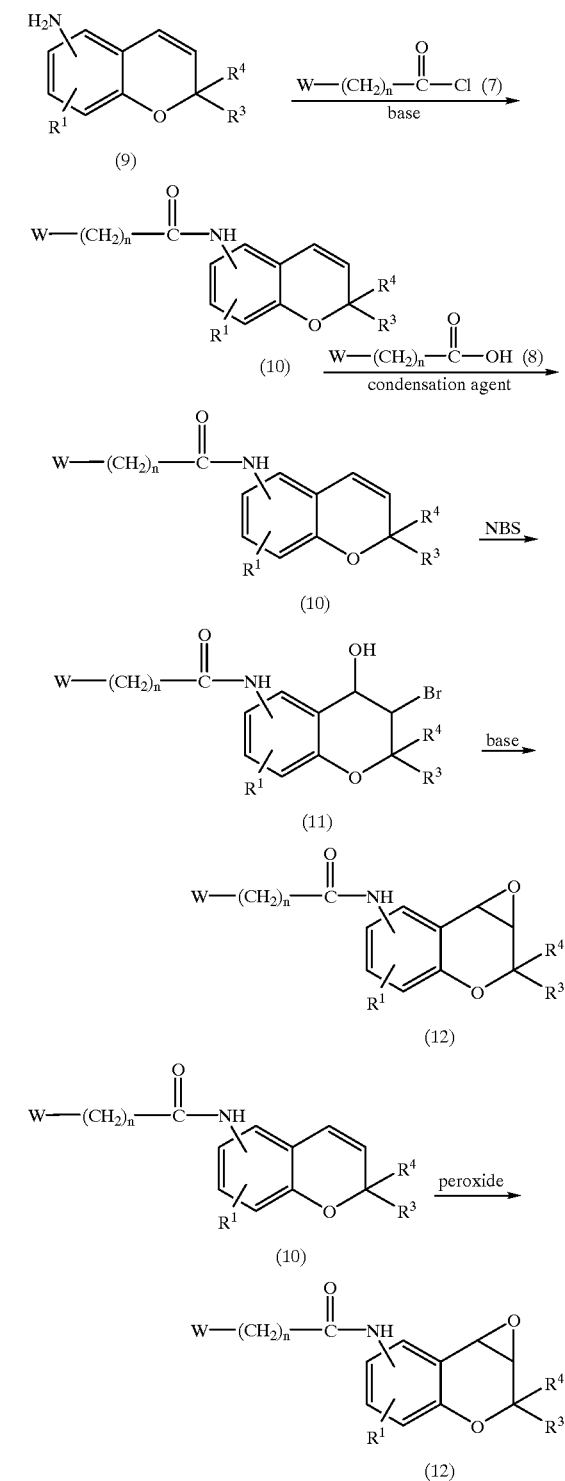

The compound (12) may be obtained in the process that after an acetyl group of the compound (4) is deprotected by using a base, the deprotected compound is reacted with the acid chloride (7) is reacted in the presence of a base or is reacted with the carboxlyic acid (8) by using a condensation agent.

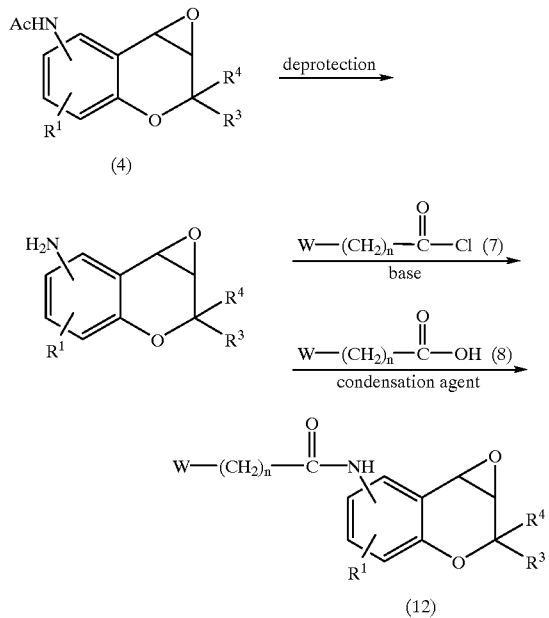

(4)

(12)

Of the compounds of the formula (2), a compound (14) in which X represents $CH_2$, Y represents NH and Z means a bond are obtained by dealing with a compound (13) which is obtained by reducing the compound (10) by using a reducing agent, in the same method mentioned above. Further, the compound (13) is obtained by reacting the compound (9) with a compound (15) in the presence of a base or reducing a compound (17) by using a suitable reducing agent.

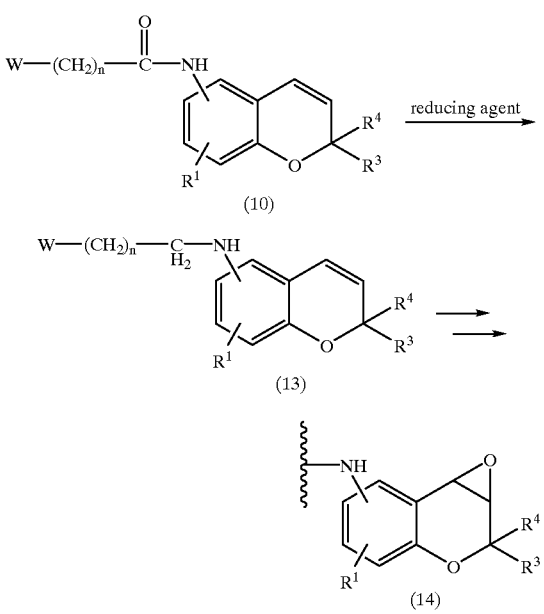

(10)

(13)

(14)

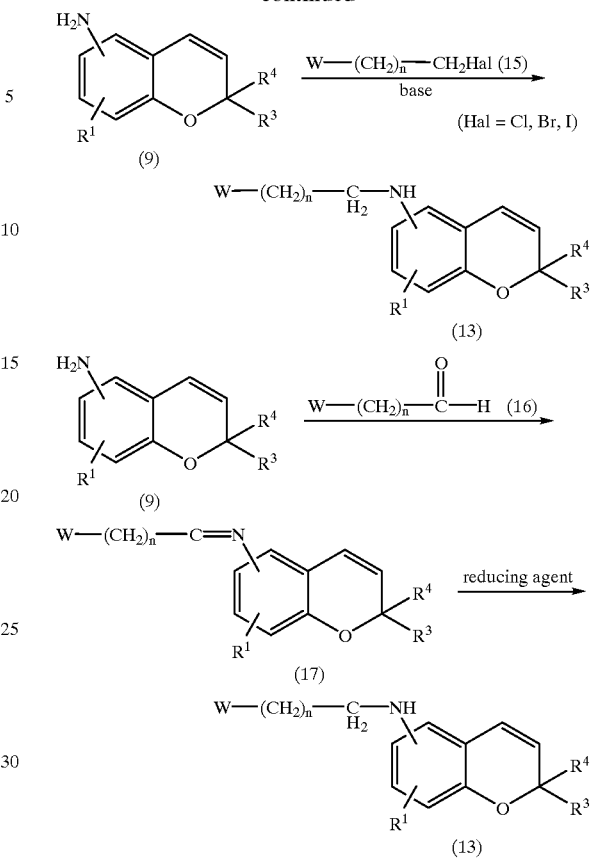

(9)

(13)

(9)

(17)

(13)

Of the compounds of the formula (2), a compound (20) in which X represents $SO_2$, Y represents NH and Z means a bond is obtained by dealing with a compound (19) which is obtained by reacting the compound (9) with the compound (18) in the presence of a base, in the same method mentioned above.

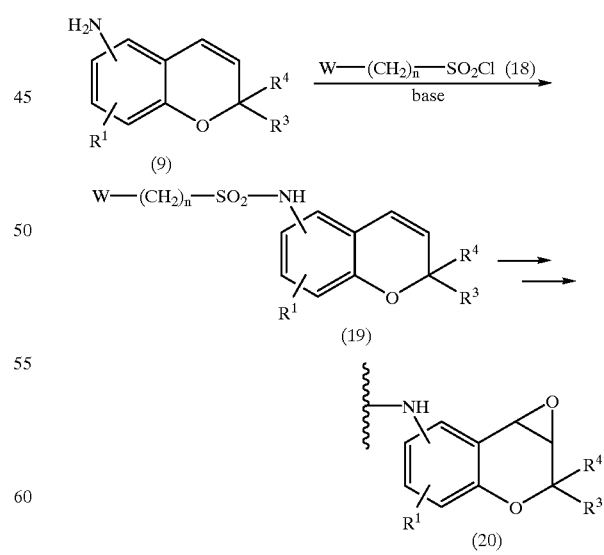

(9)

(19)

(20)

Of the compounds of the formula (2), a compound (23) in which X represents NH, Y represents C=O, Z represents NH is obtained by dealing with a compound (22) which is obtained by reacting the compound (9) with the compound (21), in the same method mentioned above.

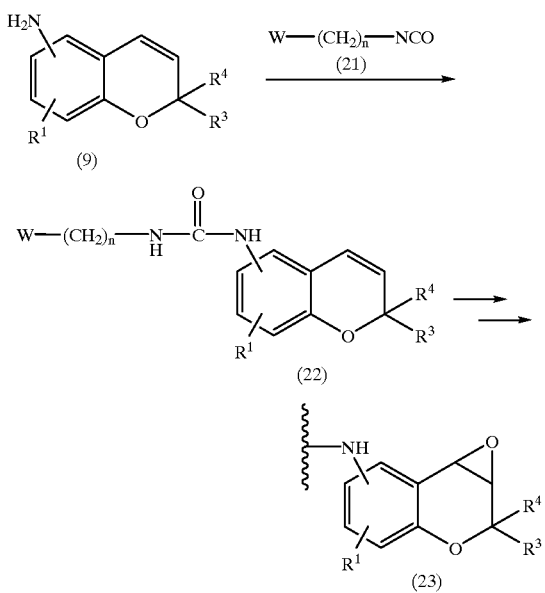

Of the compounds of the formula (I), as shown in the following reaction scheme, a compound (26) in which $R^7$ and $R^8$ each independently represent a hydrogen atom or a $C(=Y^1)Z^1R^{10}$ is obtained by reacting a compound of the formula (24) which is easily obtained by dealing with a compound of the formula (2) with an ammonia (the conversion of the compound of the formula (2) into the compound of the formula (24) has been known and the conversion can be accomplished according to, for example, Japanese Patent Application Laid-open No. Sho 58-67683, Japanese Patent Application Laid-open No. Sho 58-188880 and Japanese Patent Application Laid-open No. Sho 58-201776) and a compound of the formula (25) in an inert solvent in the presence of a base.

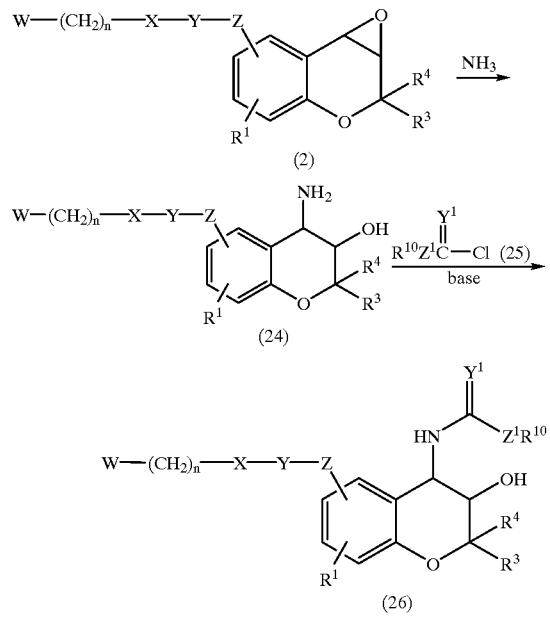

A compound (24) is obtained by reacting the compound (2) with an ammonia in an inert solvent.

As the solvent used for this reaction, the following ones are mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, alcohol solvents such as methanol or ethanol. Of these, alcohol solvents are preferable.

The reaction temperature in this reaction is, usually, from ice-cooled temperature to the reflux temperature for the reaction solvent used, preferably, from 40° C. to 80° C.

The reaction is preferably conducted in a pressure glass tube or an autoclave.

As the solvent used for the reaction of a compound of the formula (24) and a compound of the formula (25), the following ones are mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, alcohol solvents such as methanol, ethanol or propanol. The reaction can be conducted in the absence of a solvent. Of these, halogenated solvents are preferable.

The base to be used for the reaction includes, for example, trialkylamines such as triethylamine and ethyldiisopropylamine, pyridineamines such as pyridine, 2,6-lutidine, 2,6-di-t-butylpyridine and 2,6-di-t-butyl-4-methylpyridine, preferably, triethylamine, ethyldiisopropylamine and pyridine.

The reaction temperature in this reaction is, usually, from −20° C. to a reflux temperature for the reaction solvent used, preferably, from 0° C. to 60° C.

Regarding molar ratio of the reaction materials, the ratio of the base/the compound (25) is within the range of from 0.5 to 2.0, preferably, 1.0 to 1.5.

Regarding molar ratio of the reaction materials, the ratio of the compound (25)/the compound (24) is within the range of from 0.5 to 2.0, preferably, 1.0 to 2.0.

Of the compounds of the formula (I), as shown in the following reaction scheme, a compound (28) in which $R^7$ and $R^8$ together represents $(CH_2)_qZ^1C(=Y^1)$ is obtained by reacting a compound of the formula (27) in an inert solvent in the presence of a base.

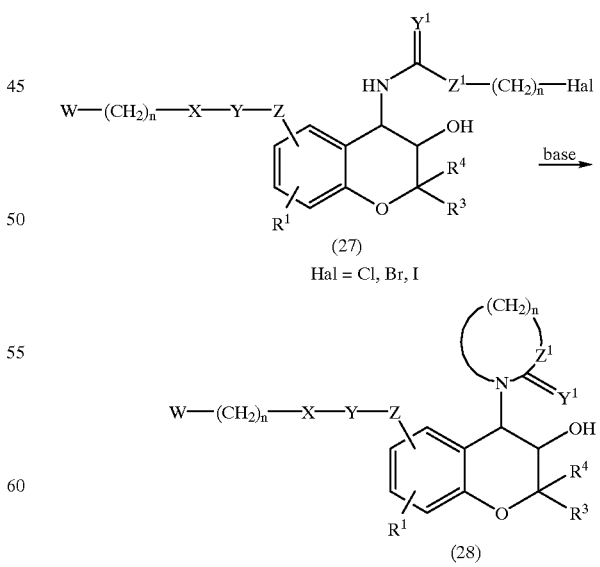

As the solvent used for the reaction of the compound of the formula (27) and the base, the following ones are mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, alcohol solvents such as methanol, ethanol or propanol. Of these, alcohol solvents are preferable. The reaction can be conducted in the abasence of a solvent. Preferable solvents are sulfoxide solvents and amid solvents.

As the base, sodium hydride, potassium hydride, potassium alkoxides such as potassium-t-butoxide, sodium alkoxides such as sodium methoxide and sodium ethoxide, tetraalkyl-ammonium hydroxides such as tetramethylammonium hydroxide and tetraethylammonium hydroxide, quarternary-ammonium halides such as trimethylbenzylammonium bromide, inorganic alkali metal salts such as potassium carbonate, potassium hydrogencarbonate, potassium hydroxide, sodium carbonate, sodium hydrogencarbonate and sodium hydroxide are mentioned. Preferable ones are sodium alkoxide, tetraalkylammonium-hydroxide.

The reaction temperature in this reaction is, usually, from $-20°$ C. to a reflux temperature for the reaction solvent used, preferably, from $0°$ C. to $60°$ C.

Regarding molar ratio of the reaction materials, the ratio of the base/the compound (27) is within the range of from 0.5 to 2.0, preferably, 1.0 to 1.5.

Of the compounds of the formula (I), as shown in the following reaction scheme, a compound (30) in which $R^7$ and $R^8$, together with a nitrogen atom to which they are bonded, form a pyrrolyl group is synthesized from a compund (24).

As the acid catalyst used, a hydrochloric acid, a sulfuric acid, a formic acid, an acetic acid and a propionic acid are mentioned.

Of the compounds of the formula (I), as shown in the following reaction scheme, a compound (33) and a compound (34) in which $R^7$ and $R^8$, together with the nitrogen atom to which they are bonded, form a pyrazolyl group are synthesized from the compound (2) by two steps.

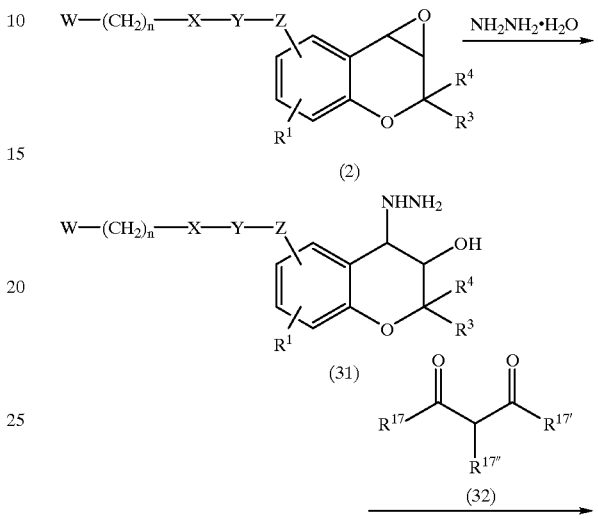

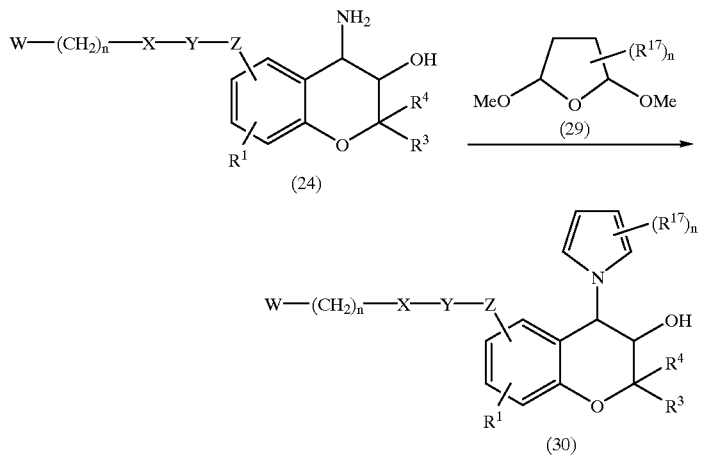

The compound (30) is obtained by reacting the compound (24) with a compound (29) in an insert solvent in the presence of an acid catalyst.

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane. The reaction can be conducted in the absence of a solvent. The acid catalyst can be used as a solvent as it is.

The reaction temperature in this reaction is, usually, from ice-cooled temperature to a reflux temperature for the reaction solvent used, preferably, the reflux temperature.

Regarding molar ratio of the reaction materials, the ratio of the compound (29)/the compound (24) is within the range of from 0.5 to 4.0, preferably, 1.0 to 2.0.

-continued

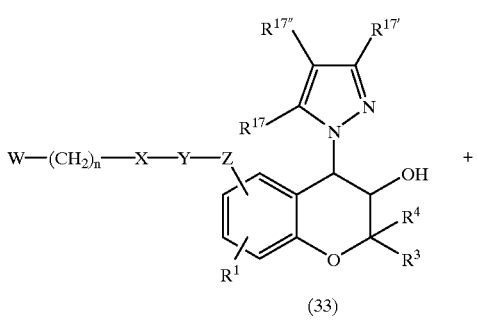

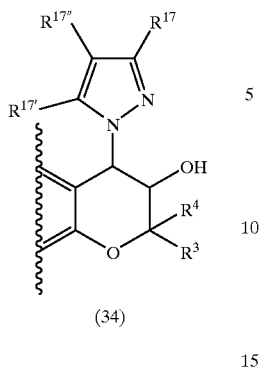

(34)

A compound (31) is obtained by reacting the compound (2) with a hydrazine monohydrate in an inert solvent.

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, and alcohols such as methanol and ethanol. Preferable solvents are the alcohols.

The reaction temperature in this reaction is, usually, from ice-cooled temperature to a reflux temperature for the reaction solvent used, preferably, from 40° C. to 80° C.

Regarding molar ratio of the reaction materials, the ratio of the hydrazine monohydrate/the compound (2) is within the range of from 0.5 to 10.0, preferably, 1.0 to 2.0.

The compound (33) and the compound (34) are obtained by reacting the compound (31) with the compound (32) in an inert solvent.

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, and alcohols such as methanol and ethanol. The reaction can be conducted in the absence of a solvent.

The reaction temperature in this reaction is, usually, from ice-cooled temperature to a reflux temperature for the reaction solvent used.

Regarding molar ratio of the reaction materials, the ratio of the compound (32)/the compound (31) is within the range of from 0.5 to 5.0, preferably, 1.0 to 2.0.

The compound (33) and the compound (34) are isolated by the known isolation method in the organic chemistry such as recrystalization or column chromatography.

Of the compounds of the formula (I), as shown in the following reaction scheme, a compound (36) in which $R^7$ and $R^8$, together with a nitrogen atom to which they are bonded, form an imidazolyl group is obtained by reacting the compound (2) with the compound (35) in an inert solvent in the presence of sodium hydride. Coexistence with a phase transfer catalyst such as 18-crown-6 is preferable.

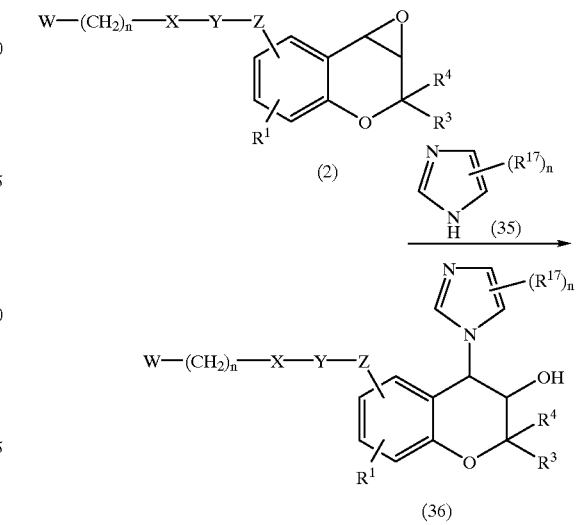

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane and aromatic solvents such as benzene and toluene, preferably, aromatic solvents.

The reaction temperature in this reaction is, usually, from ice-cooled temperature to a reflux temperature for the reaction solvent used.

Regarding molar ratio of the reaction materials, the ratio of the compound (35)/the compound (2) is within the range of from 0.5 to 5.0, preferably, 1.0 to 2.0.

Of the compounds of the formula (I), as shown in the following reaction scheme, a compound (38) in which $R^7$ and $R^8$, together with a nitrogen atom to which they are bonded, form a 1,2,4-triazolyl group is obtained by reacting the compound (2) with the compound (37) in an inert solvent in the presence of a sodium hydride. Coexistence with a phase transfer catalyst such as 18-crown-6 is preferable.

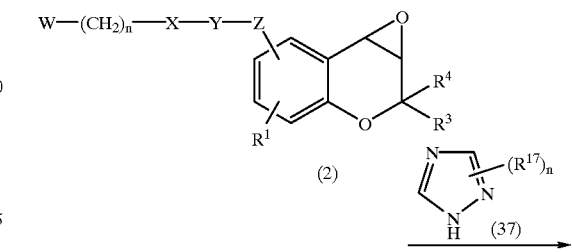

-continued

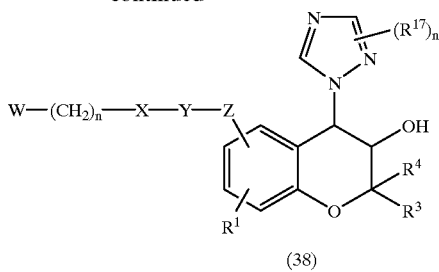
(38)

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, and aromatic solvents such as benzene and toluene. The aromatic solvents are preferable.

The reaction temperature in this reaction is, usually, from ice-cooled temperature to a reflux temperature for the reaction solvent used.

Regarding molar ratio of the reaction materials, the ratio of the compound (37)/the compound (2) is within the range of from 0.5 to 5.0, preferably, 1.0 to 2.0.

Of the compounds of the formula (I), as shown in the following reaction scheme, a compound (40) in which $R^7$ and $R^8$, together with a nitrogen atom to which they are bonded, form a 1,2,3-triazolyl group is obtained by reacting the compound (2) with the compound (39) in an inert solvent in the presence of a sodium hydride. Coexistence with a phase transfer catalyst such as 18-crown-6 is preferable.

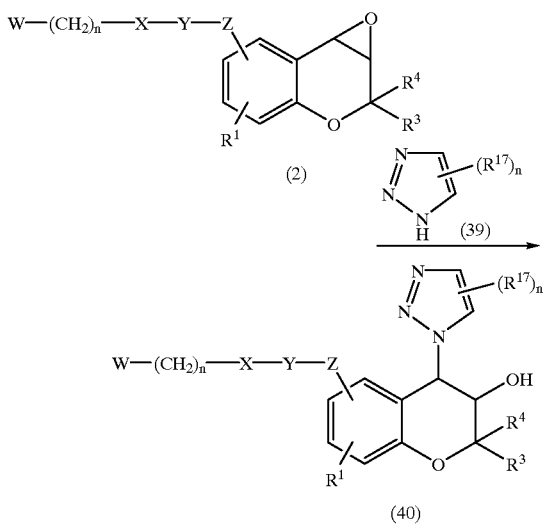

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, and aromatic solvents such as benzene and toluene. The aromatic solvents are preferable.

The reaction temperature in this reaction is, usually, from ice-cooled temperature to a reflux temperature for the reaction solvent used.

Regarding molar ratio of the reaction materials, the ratio of the compound (39)/the compound (2) is within the range of from 0.5 to 5.0, preferably, 1.0 to 2.0.

The compound (40) can be synthesized from the compound (2) by two steps, as shown in the following reaction scheme.

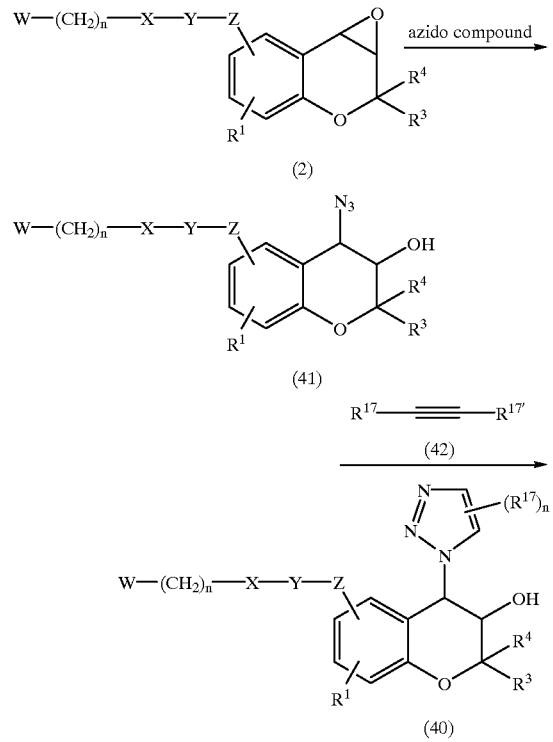

A compound (41) is obtained by reacting the compound (2) with azido compounds such as sodium azide, lithium azide and trimethylsilyl azide in an inert solvent.

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, and aromatic solvents such as benzene and toluene. The aromatic solvents are preferable.

The reaction temperature in this reaction is, usually, from ice-cooled temperature to a reflux temperature for the reaction solvent used.

Regarding molar ratio of the reaction materials, the ratio of the azido compound/the compound (2) is within the range of from 0.5 to 5.0, preferably, 1.0 to 2.0.

The compound (40) is obtained by reacting the compound (41) with the compound (42) in an inert solvent.

As the solvent used for the reaction, the following is mentioned.

Such solvents are sulfoxide solvents such as dimethylsulfoxide, amide solvents such as dimethylformamide and dimethylacetamide, ethereal solvents such as ethyl ether, dimethoxyethane and tetrahydrofuran, halogenated solvents such as dichloromethane, chloroform and dichloroethane, and aromatic solvents such as benzene and toluene. The aromatic solvents are preferable.

The reaction temperature in this reaction is, usually, from 5° C. to 140° C., preferably, from 80° C. to 120° C.

Regarding molar ratio of the reaction materials, the ratio of the compound (42)/the compound (41) is within the range of from 0.5 to 5.0, preferably, 1.0 to 2.0.

It is preferable to conduct this reaction in a pressure glass tube or an autoclave.

Of the compounds of the formula (I), as shown in the following reaction scheme, a compound (43) in which $R^5$ represents $C_{1-6}$ alkylcarbonyloxy group can be synthesized by reacting the compound (I) with an acylating agent in an inert solvent in the presence of a suitable base.

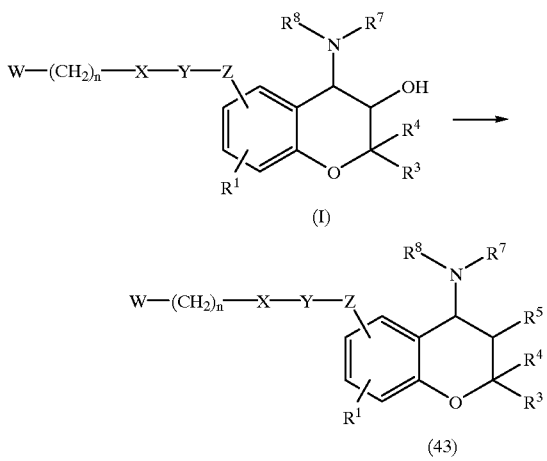

Such solvents are sulfoxide solvents such as dimethylsulfoxide, amide solvents such as dimethylformamide and dimethylacetamide, ethereal solvents such as ethyl ether, dimethoxyethane and tetrahydrofuran, and halogenated solvents such as dichloromethane, chloroform and dichloroethane. The reaction can be conducted in the absence of a solvent.

The reaction temperature in this reaction is, usually, from ice-cooled temperature to a reflux temperature for the reaction solvent used.

As the base to be used for this reaction, triethylamine, pyridine, diisopropylethylamine and DBU (diazabicycloundecene) are mentioned.

As the acylating agent, acid halides such a acid chloride and acid bromide, and acid anhydrides.

Regarding molar ratio of the reaction materials, the ratio of the compound (I)/the acylating agent is within the range of from 0.5 to 4.0, preferably, 1.0 to 2.0.

Of the compounds of the formula (I), a compound (44) in which $R^5$ and $R^6$ together form a bond is obtained by reacting the compound (I) in an inert solvent in the presence of inorganic bases such as potassium carbonate, sodium hydroxide, potassium hydroxide and sodium hydride or organic bases such as tetraalkylammoniumhydroxide.

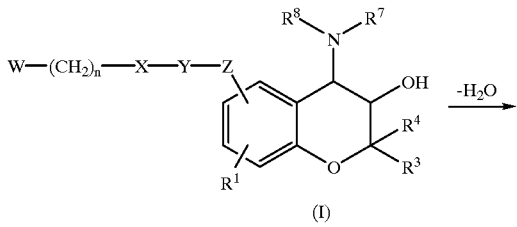

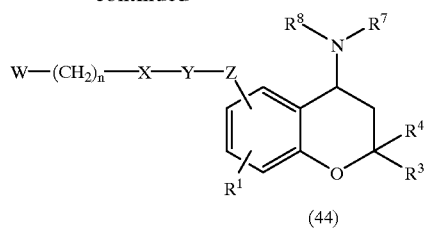

Of the compounds of the formula (I), optically active isomers may be produced, for example, by methods of optical resolution of racemic modification (Japanese Patent Application Laid-open No. Hei 3-141286, U.S. Pat. No. 5,097,037 and EP-A-409 165). The synthesis of optically active isomers of the compounds of the formulas (6) and (24) may be produced by the methods of asymmetric synthesis (Japanese National Publication No. Hei 5-507645, Japanese Patent Application Laid-open No. Hei 5-301878, Japanese Patent Application Laid-open No. Hei 7-285983, EP-A-535 377 and U.S. Pat. No. 5,420,314).

As mentioned above, the present invention have found that the compounds of the formula (I) have a strong activity of reducing the heart rate. Since the compounds of the present invention have no activity of retarding cardiac functions but rather have an activity of reducing the heart rate, they may exert the activity of enhancing the contraction of cardiac muscles even when they are administered in the same amount as that necessary for expressing the cardiotonic activity. Because of their activities, it is considered that the compounds according to the present invention may reduce the amount of oxygen to be consumed by cardiac muscles to therefore reduce the motility load of cardiac muscles and exert the anti-stenocardiac activity. In addition, it is also considered that they have an activity of prolonging the effective refractory period to thereby exert an antiarrhythmic activity. Therefore, it is expected that the compounds of the present invention are useful for curing cardiovascular disorders in consideration of the oxygen consumption, the energy consumption or the metabolism caused by the cardiac motility and also for curing other cardiac disorder essentially in consideration of the activity of the compounds of reducing the heart rate. For example, the compounds of the present invention are useful as medicines for cardiac insufficiency of mammals including human beings and also as medicines for curing cardiovascular disorders causing cardiac insufficiency of them such as, for example, medicines for curing isochemic cardiopathy, medicines for curing hypertension, medicines for curing cardiac fluid retention, medicines for curing pulmonary hypertension, medicines for curing valvulitis, medicines for curing congenital cardiac disorders, medicines for curing cardiomuscular disorders, medicines for curing pulmonary edema, medicines for curing angina of effort, medicines for curing myocardial infarction, medicines for curing arrhythma, and medicines for curing atrial fibrillation.

The present invention provides pharmaceutical compositions containing an effective amount of the compounds of the formula (I) for curing these diseases.

As the manner of administration of the compounds of the present invention, there may be mentioned parenterally administration by injections (subcutaneous, intravenous, intramuscular or intraperitoneal injection), ointments, suppositories or aerosols, or an oral administration in the form of tablets, capsules, granules, pills, syrups, liquids, emulsions or suspensions.

The above pharmacological or veterinary composition of the present invention contain the above-mentioned compounds of the present invention in an amount of from about 0.01 to 99.5% by weight, preferably from about 0.1 to 30% by weight, based on the total weight of the composition.

To the compounds of the present invention or to the compositions containing the present compounds, other pharmacologically or veterinarily active compounds may be incorporated. Further, the compositions of the present invention may contain a plurality of the compounds of the present invention.

The clinical dose of the compounds of the present invention varies depending upon the age, the body weight, the sensitivity or the sympton, etc. of the patient. In general, however, the effective daily dose is usually from about 0.003 to 1.5 g, preferably from about 0.01 to 0.6 g for an adult. If necessary, however, an amount outside the above range may be employed.

The compounds of the present invention may be prepared into various suitable formulations depending upon the manner of administration, in accordance with conventional methods commonly employed for the preparations of pharmaceutical formulations.

Namely, tablets, capsules, granules or pills for oral administration, may be prepared by using excipients such as white sugar, lactose, glucose, starch or mannitol; binders such as hydroxypropyl cellulose, syrups, arabic gum, gelatin, sorbitol, tragacanth gum, methyl cellulose or polyvinylpyrrolidone; disintegrants such as starch, carboxymethyl cellulose (CMC) or its calcium salt, crystal cellulose powder or polyethylene glycol (PEG); lubricants such as talc, magnesium or calcium stearate, silica; and smoothers such as sodium laurate, glycerol, etc.

The injections, solutions (liquids), emulsions, suspensions, syrups or aerosol may be prepared using a solvent for the active ingredient such as water, ethyl alcohol, isopropyl alcohol, propylene glycol, 1,3-butylene glycol or polyethylene glycol; surfactants such as sorbitan fatty acid esters, polyoxyethylene sorbitan fatty acid esters, polyoxyethylene fatty acid esters, polyoxyethylene ether of hydrogenated castor oil, lecithin; suspending agents such as cellulose derivatives such as sodium salt of carboxymethyl cellulose derivatives such as methyl cellulose or natural rubbers such as tragacanth or arabic gum; or preservatives such as para-hydroxybenzoic acid, benzalkonium chloride, salts of sorbic acid, etc.

Ointments which are an endermic preparation may be prepared by using, e.g., white vaseline, liquid paraffin, higher alcohols, Macrogol ointment, hydrophilic ointment base or hydrogel base, etc.

The suppositories may be prepared by using, e.g., cacao butter, polyethylene glycol, lanolin, fatty acid triglycerides, coconut oil, polysorbate, etc.

BEST MODE FOR CARRYING OUT THE INVENTION

Now, the present invention is explained referring to examples, but it is not to be limited to these examples.

SYNTHESIS EXAMPLE

Referential Example 1

Synthesis of 6-(benzoylamino)-2,2-dimethyl-7-nitro-2H-1-benzopyran (IV-1)

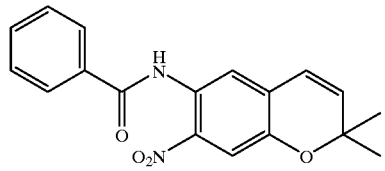

Benzoyl chloride (0.55 mL, 1.5 eq.) was added to a chloroform (10 mL) solution of 6-amino-2,2-dimethyl-7-nitro-2H-1-benzopyran (which was synthesized according to the method of Evans, J. M. et al., J. Med. Chem. 1984, 27, 1127) (700 mg, 3.18 mmol) and triethylamine. (0.58 mL, 1.3 eq.) at 0° C. The mixture was stirred at 0° C. for three hours and at room temperature for one and half hours. After a saturated aqueous ammonium chloride solution was added to the resulting mixture, the mixture was extracted with chloroform and dried over sodium sulfurate anhydride. After the solvent was distilled off, the obtained residue was purified through silica gel column chromatography (hexane:ethyl acetate=5:1) to obtain the intended product (570 mg, 55%) as an orange solid.

$^1$H NMR (CDCl$_3$) δ: 1.45 (s, 6H), 5.87 (d, J=10 Hz, 1H),
6.40 (d, J=10 Hz, 1H),
7.40–8.05 (m, 7H), 8.56 (s, 1H).

The following compounds were obtained in the same manner of the Referential Example 1 by using, instead of the benzoyl chloride, acid chlorides (which are commercially available to obtain as a reagent or can be synthesized by using a thionyl chloride from a corresponding calboxylic acid) corresponding to compounds IV-2 to IV-21. Compounds IV-8 was obtained by using a phenyl isocyanate instead of the acid chloride.

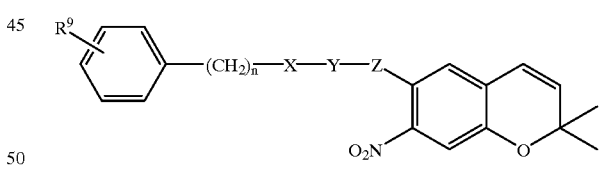

| Compound | R$^9$ | n | X | Y | Z |
|---|---|---|---|---|---|
| IV-2 | H | 1 | CO | NH | — |
| IV-3 | H | 2 | CO | NH | — |
| IV-4 | m,p-(OMe)$_2$ | 1 | CO | NH | — |
| IV-5 | p-OMe | 1 | CO | NH | — |
| IV-6 | p-Me | 1 | CO | NH | — |
| IV-7 | p-Cl | 1 | CO | NH | — |
| IV-8 | H | 0 | NH | CO | NH |
| IV-9 | p-F | 1 | CO | NH | — |
| IV-10 | p-NO$_2$ | 1 | CO | NH | — |
| IV-11 | m,p-(OMe)$_2$ | 2 | CO | NH | — |
| IV-12 | p-OMe | 2 | CO | NH | — |
| IV-13 | m-OMe | 1 | CO | NH | — |
| IV-14 | o-OMe | 1 | CO | NH | — |
| IV-15 | p-Ph | 1 | CO | NH | — |
| IV-16 | p-OEt | 1 | CO | NH | — |
| IV-17 | p-Br | 1 | CO | NH | — |
| IV-18 | o-Ph | 1 | CO | NH | — |

-continued

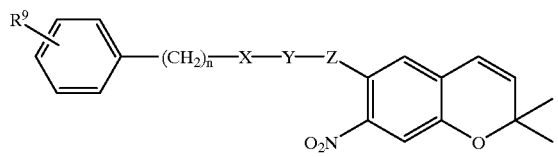

| Compound | R⁹ | n | X | Y | Z |
|---|---|---|---|---|---|
| IV-19 | m-Ph | 1 | CO | NH | — |
| IV-20 | p-NHAc | 1 | CO | NH | — |
| IV-21 | p-OH | 1 | CO | NH | — |

Compound IV-2
¹H NMR (CDCl₃) δ: 1.41 (s, 6H), 3.73 (s, 2H),
5.79 (d, J=10 Hz, 1H),
6.29 (d, J=10 Hz, 1H),
7.04–7.36 (m, 5H), 7.42 (s, 1H)
8.29 (s, 1H), 9.97 (bs, 1H).
MS (FAB) m/z: 157, 339[M+H]⁺.

Compound IV-3
¹H NMR (CDCl₃) δ: 1.42 (s, 6H), 2.52–3.22 (m, 4H),
5.78 (d, J=9 Hz, 1H),
6.30 (d, J=9 Hz, 1H),
7.14 (s, 5H), 7.43 (s, 1H)
8.34 (s, 1H), 10.09 (bs, 1H).
MS (FAB) m/z: 157(bp), 353[M+H]⁺.

Compound IV-4
¹H NMR (CDCl₃) δ: 1.44 (s, 6H), 3.69 (s, 2H), 3.87 (s, 6H),
5.80 (d, J=9 Hz, 1H),
6.31 (d, J=9 Hz, 1H),
6.83 (s, 3H), 7.47 (s, 1H)
8.29 (s, 1H), 10.04 (bs, 1H).
MS (FAB) m/z: 151(bp), 399[M+H]⁺.

Compound IV-5
¹H NMR (CDCl₃) δ: 1.39 (s, 6H), 3.63 (s, 2H), 3.72 (s, 3H),
5.75 (d, J=9 Hz, 1H),
6.23 (d, J=9 Hz, 1H),
6.61–7.21 (m, 4H), 7.39 (s, 1H)
8.25 (s, 1H), 9.94 (bs, 1H).
MS (FAB) m/z: 121(bp), 369[M+H]⁺.

Compound IV-6
¹H NMR (CDCl₃) δ: 1.44 (s, 6H), 2.35 (s, 3H), 3.73 (s, 2H),
5.79 (d, J=10 Hz, 1H),
6.29 (d, J=10 Hz, 1H),
7.14 (s, 4H), 7.46 (s, 1H)
8.31 (s, 1H), 10.02 (bs, 1H).
MS (FAB) m/z: 105, 353[M+H]⁺ (bp).

Compound IV-7
¹H NMR (CDCl₃) δ: 1.40 (s, 6H), 3.73 (s, 2H),
5.79 (d, J=9 Hz, 1H),
6.28 (d, J=9 Hz, 1H),
7.26 (s, 4H), 7.47 (s, 1H)
8.28 (s, 1H), 10.10 (bs, 1H).
MS (FAB) m/z: 125(bp), 373[M+H]⁺.

Compound IV-8
¹H NMR (CDCl₃) δ: 1.41 (s, 6H),
5.78 (d, J=10 Hz, 1H),
6.25 (d, J=10 Hz, 1H),
6.90–7.54 (m, 7H), 8.16 (s, 1H)
9.69 (bs, 1H).
MS (FAB) m/z: 157(bp), 340[M+H]⁺.

Compound IV-9
¹H NMR (CDCl₃) δ: 1.41 (s, 6H), 3.67 (s, 2H),
5.75 (d, J=10 Hz, 1H),
6.25 (d, J=10 Hz, 1H),
6.77–7.37 (m, 4H), 7.40 (s, 1H)
8.13 (s, 1H), 9.95 (bs, 1H).
MS (FAB) m/z: 109(bp), 357[M+H]⁺, mp. 160–162° C.

Compound IV-10
¹H NMR (CDCl₃) δ: 1.47 (s, 6H), 3.89 (s, 2H),
5.87 (d, J=9 Hz, 1H),
6.32 (d, J=9 Hz, 1H),
7.29–7.62 (m, 3H),
7.99–8.34 (m, 3H), 10.18 (bs, 1H).
MS (EI) m/z: 322(bp), 383[M+], mp. 188–191° C.

Compound IV-11
¹H NMR (CDCl₃) δ: 1.44 (s, 6H), 2.53–3.20 (m, 4H),
3.80 (s, 6H),
5.80 (d, J=10 Hz, 1H),
6.29 (d, J=10 Hz, 1H),
6.70 (s, 3H), 7.46 (s, 3H)
8.27 (s, 1H), 10.00 (bs, 1H).
MS (FAB) m/z: 96(bp), 413[M+H]⁺.

Compound IV-12
¹H NMR (CDCl₃) δ: 1.45 (s, 6H), 2.48–3.18 (m, 4H),
3.74 (s, 3H),
5.82 (d, J=10 Hz, 1H),
6.32 (d, J=10 Hz, 1H),
6.66–7.28 (m, 4H), 7.49 (s, 3H)
8.31 (s, 1H), 10.05 (bs, 1H).
MS (FAB) m/z: 121(bp), 383[M+H]⁺, mp. 100–102° C.

Compound IV-13
¹H NMR (CDCl₃) δ: 1.41 (s, 6H), 3.69 (s, 2H),
3.76 (s, 3H),
5.76 (d, J=10 Hz, 1H),
6.28 (d, J=10 Hz, 1H),
6.64–6.96 (m, 3H), 7.08–7.36 (m, 1H)
7.41 (s, 1H), 8.27 (s, 1H), 9.99 (bs, 1H).
MS (FAB) m/z: 121(bp), 369[M+H]⁺, mp. 82–83° C.

Compound IV-14
¹H NMR (CDCl₃) δ: 1.41 (s, 6H), 3.72 (s, 2H), 3.94 (s, 3H),
5.79 (d, J=10 Hz, 1H),
6.30 (d, J=10 Hz, 1H),
6.74–7.36 (m, 4H), 7.44 (s, 1H)
8.30 (s, 1H), 10.13 (bs, 1H).
MS (FAB) m/z: 185(bp), 369[M+H]⁺, mp. 103–104° C.

Compound IV-15
¹H NMR (CDCl₃) δ: 1.40 (s, 6H), 3.76 (s, 2H),
5.79 (d, J=10 Hz, 1H), 6.30 (d, J=10 Hz, 1H), 7.15–7.75 (m, 10H), 8.33 (s, 1H), 10.11 (bs, 1H).

MS (FAB) m/z: 167(bp), 415[M+H]$^+$, mp. 103–105° C.

Compound IV-16

$^1$H NMR (CDCl$_3$) δ: 1.40 (t, J=7 Hz, 3H), 1.44 (s, 6H), 3.69 (s, 2H), 4.01 (q, J=7 Hz, 2H), 5.81 (d, J=10 Hz, 1H), 6.33 (d, J=10 Hz, 1H), 6.77–7.39 (m, 4H), 7.48 (s, 1H), 8.34 (s, 1H), 10.04 (bs, 1H).

MS (FAB) m/z: 135(bp), 383[M+H]$^+$, mp. 102–104° C.

Compound IV-17

$^1$H NMR (CDCl$_3$) δ: 1.42 (s, 6H), 3.69 (s, 2H), 5.80 (d, J=11 Hz, 1H), 6.30 (d, J=11 Hz, 1H), 7.09–7.52 (m, 5H), 8.28 (s, 1H) 10.10 (bs, 1H).

MS (EI) m/z: 90(bp), 416[M–1]

Compound IV-18

$^1$H NMR (CDCl$_3$) δ: 1.43 (s, 6H), 3.77 (s, 2H), 5.87 (d, J=10 Hz, 1H), 6.34 (d, J=10 Hz, 1H), 7.26–7.43 (m, 9H), 7.53 (s, 1H)

8.33 (s, 1H), 9.95 (bs, 1H).

MS (EI) m/z: 205(bp), 415[M+1]

Compound IV-19

$^1$H NMR (CDCl$_3$) δ: 1.43 (s, 6H), 3.85 (s, 2H), 5.88 (d, J=10 Hz, 1H), 6.37 (d, J=10 Hz, 1H), 7.26–7.62 (m, 10H), 8.41 (s, 1H)

10.21 (bs, 1H).

MS (EI) m/z: 353(bp), 415[M+1]

Compound IV-20

$^1$H NMR (CDCl$_3$) δ: 1.40 (s, 6H), 2.10 (s, 3H), 3.71 (s, 2H), 5.83 (d, J=10 Hz, 1H), 6.32 (d, J=10 Hz, 1H), 7.13–7.80 (m, 6H), 8.30 (s, 1H)

10.01 (bs, 1H).

MS (EI) m/z: 106(bp), 395[M$^+$]

Compound IV-21

$^1$H NMR (CDCl$_3$) δ: 1.43 (s, 6H), 3.67 (s, 2H), 5.49 (s, 1H), 5.81 (d, J=10 Hz, 1H), 6.14 (d, J=10 Hz, 1H), 6.29 (d, J=8 Hz, 2H), 7.15 (d, J=8 Hz, 2H), 7.47 (s, 1H)

8.39 (s, 1H), 10.04 (bs, 1H).

MS (EI) m/z: 77(bp), 354[M$^+$]

Compound IV-22

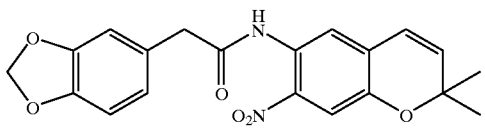

$^1$H NMR (CDCl$_3$) δ: 1.43 (s, 6H), 3.66 (s, 2H), 5.91 (s, 2H), 5.84 (d, J=10 Hz, 1H), 6.33 (d, J=10 Hz, 1H), 6.78 (s, 3H), 7.49 (s, 1H), 8.33 (s, 1H), 10.10 (bs, 1H).

MS (FAB) m/z: 135(bp), 383[M+H]$^+$, mp. 136–138° C.

Compound IV-23

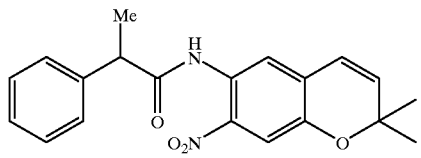

$^1$H NMR (CDCl$_3$) δ: 1.40 (s, 6H), 1.60 (d, J=7 Hz, 3H), 3.71 (q, J=7 Hz, 1H), 5.74 (d, J=10 Hz, 1H), 6.23 (d, J=10 Hz, 1H), 7.06–7.36 (m, 5H), 7.40 (s, 1H), 8.31 (s, 1H), 10.03 (bs, 1H).

MS (EI) m/z: 58(bp), 352[M+]

Compound IV-24

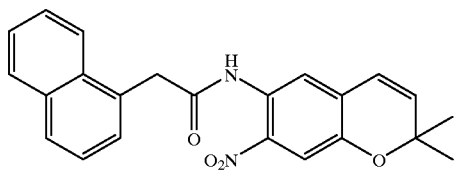

$^1$H NMR (CDCl$_3$) δ: 1.39 (s, 6H), 4.19 (s, 2H), 5.78 (d, J=10 Hz, 1H), 6.29 (d, J=10 Hz, 1H), 7.35–8.15 (m, 8H), 8.34 (s, 1H), 10.05 (bs, 1H).

MS (FAB) m/z: 141(bp), 389[M+H]$^+$, mp. 111–114° C.

Compound IV-25

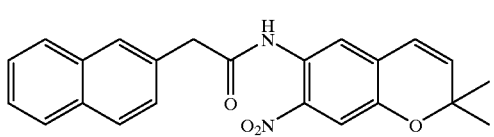

$^1$H NMR (CDCl$_3$) δ: 1.40 (s, 6H), 3.90 (s, 2H), 5.79 (d, J=10 Hz, 1H), 6.30 (d, J=10 Hz, 1H), 7.30–8.00 (m, 8H), 8.33 (s, 1H), 10.15 (bs, 1H).

MS (FAB) m/z: 141(bp), 389[M+H]$^+$, mp. 152–155° C.

Compound IV-26

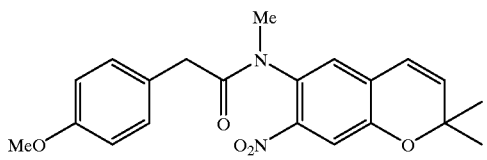

A 60% sodium hydride (77 mg, 1.2 eq.) was added to a DMF (5 mL) solution of the compound IV-5 (1.0 g, 2.7 mmol) at 0° C. and the mixture was stirred at 0° C. for ten minutes. Further, a methyl iodide (0.19 mL, 1.1 eq.) was added to the mixture at 0° C., and stirred at 0° C. and at room temperature for one hour. The resulting mixture was diluted with water and then extracted with an ethyl acetate and dried over an sodium sulfate anhydride. After the solvent was distilled off, the obtained residue was purified through silica gel column chromatography (hexane:ethyl acetate=2:1) to obtain the intended product (0.63 g, 61%) as a light brown oil.

$^1$H NMR (CDCl$_3$) δ: 1.50 (s, 6H), 3.15 (s, 3H), 3.31 (s, 2H), 3.72 (s, 3H), 5.79 (d, J=11 Hz, 1H), 6.27 (d, J=11 Hz, 1H), 6.60–7.33 (m, 6H).

MS (FAB) m/z: 121(bp), 383[M+H]$^+$.

Compound IV-27

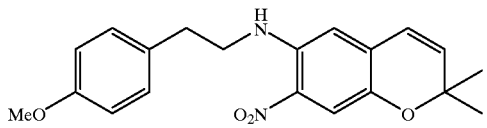

A DMF (13 mL) solution of 6-amino-2,2-dimethyl-7-nitro-2H-1-benzopyran (1.3 g, 6.0 mmol), a 60% sodium hydride (0.20 g, 1.4 eq.) and 2-(4'-methoxyphenyl)ethane iodide was stirred at 100° C. for thirteen hours and heated under reflux for three hours. After the solvent was distilled off and water was added to the solution, the resulting solution was extracted with an ethyl acetate and dried over a sodium sulfate anhydride. After the solvent was distilled off, the obtained residue was purified through silica gel column chromatography (hexane:ethyl acetate=9:1) to obtain the intended product (0.58 g, 27%) as a red oil.

$^1$H NMR (CDCl$_3$) δ: 1.41 (s, 6H), 2.95 (t, J=7 Hz, 2H), 3.47–3.52 (m, 2H), 3.80 (s, 3H), 5.95 (d, J=10 Hz, 1H), 6.31 (d, J=10 Hz, 1H), 6.45 (s, 1H), 6.87 (d, J=9 Hz, 2H), 7.18 (d, J=9 Hz, 2H), 7.59 (s, 1H), 7.99 (bs, 1H).

MS (EI) m/z: 355[M+1](bp).

Compound IV-28

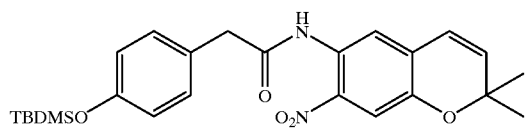

A DMF (1.0 mL) solution of a 6-(4'-hydroxybenzoyl)amino-2,2-dimethyl-7-nitro-2H-1-benzopyran (IV-21) (0.10 g, 0.28 mmol), a t-butyl-dimethylsilyl chloride (89 mg, 2.1 eq.) and an imidazol (75 mg, 4.0 eq.) was stirred at room temperature for five hours. After the solvent was distilled off, the resulting solution was added with water, extracted with ethyl acetate and dried over a sodium sulfate anhydride. The solvent was distilled off from the resulting product to obtain the intended product (0.13 g, 96%) as a light brown oil.

$^1$H NMR (CDCl$_3$) δ: 0.22 (s, 6H), 0.99 (s, 9H), 1.41 (s, 6H), 3.27 (s, 2H), 5.88 (d, J=9 Hz, 1H), 6.37 (d, J=10 Hz, 1H), 6.86 (d, J=8 Hz, 2H), 7.21 (d, J=8 Hz, 2H), 7.46 (s, 1H), 8.33 (s, 1H), 10.02 (bs, 1H).

MS (EI) m/z: 181(bp), 469[M$^+$].

Compound IV-29

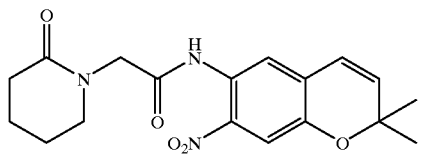

A DMF (0.4 ml) solution of δ-valerolactam (63 mg, 0.64 mmol) was added with a 60% sodium hydride (31 mg, 1.2 eq.) at room temperature and stirred at 65° C. for two and half hours. The mixture was added with 0.5 ml of DMF and cooled to 0° C. Then, a DMF(0.5 ml) solution of a 6-(chloroacetylamino)-2,2-dimethyl-7-nitro-2H-1-benzopyran (48 mg, 0.16 mmol) was added to the resulting mixture and stirred at room temperature for four hours. After water was added to the resulting mixture, the mixture was extracted with ethyl acetate and dried over a sodium sulfuric anhydride. After the solvent was distilled off, the obtained solution was purified through a silica gel thin layer chromatography to obtain the intended product (51 mg, 89%) as a light brown oil.

$^1$H NMR (CDCl$_3$) δ: 1.45 (s, 6H), 1.80–2.00 (m, 4H), 2.40–2.65 (m, 2H), 3.30–3.50 (m, 2H), 4.17 (s, 2H), 5.97 (d, J=11 Hz, 1H), 6.34 (d, J=11 Hz, 1H), 7.52 (s, 1H), 8.33 (s, 1H), 10.03 (bs, 1H).

MS (EI) m/z: 139(bp), 359[M$^+$].

Referetial Example 2

Synthesis of 6-(benzoylamino)-3-bromo-3,4-dihydro-2,2-dimethyl-7-nitro-2H-1-benzopyran-4-or (III-1)

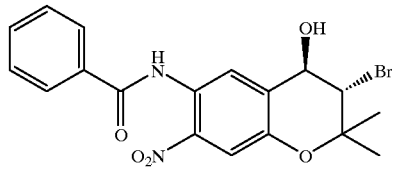

A mixed solution of a dimethylsulfoxide (DMSO) (15 mL) and water (1.2 mL) in which a 6-(benzoylamino)-2,2-dimethyl-7-nitro-2H-1-benzopyran (IV-1)(570 mg, 1.76 mmol) was dissolved was added with a N-bromosuccinic acid imide (688 mg, 2.2 eq.) stirred at room temperature for twenty three hours. After the resulting mixture was added with water and extracted with ethyl acetate, the organic layer was washed with an aqueous saturated sodium chloride solution and dried over a sodium sulfate anhydride. After the solvent was distilled off, the resulting product was purified through silica gel column chromatography (hexane:ethyl acetate=3:1) to obtain the intended product (223 mg, 30%) as a yellow amorphous.

$^1$H NMR (CDCl$_3$) δ: 1.40 (s, 3H), 1.59 (s, 3H),
  4.11 (d, J=9 Hz, 1H),
  4.19 (bs, 1H), 4.97 (d, J=9 Hz, 1H),
  7.34–8.04 (m, 6H), 8.95 (s, 1H),
  10.84 (bs, 1H).
MS (FAB) m/z: 71(bp), 421[M+H]$^+$.

The following compounds were obtained in the method of the Referential Example 2 by using the compounds IV-2 to IV-13 instead of the compound IV-1.

| Compound | R$^9$ | n | X | Y | Z |
|---|---|---|---|---|---|
| III-2 | H | 1 | CO | NH | — |
| III-3 | H | 2 | CO | NH | — |
| III-4 | m,p-(OMe)$_2$ | 1 | CO | NH | — |
| III-5 | p-OMe | 1 | CO | NH | — |
| III-6 | p-Me | 1 | CO | NH | — |
| III-7 | p-Cl | 1 | CO | NH | — |
| III-8 | H | 0 | NH | CO | NH |
| III-9 | F | 1 | CO | NH | — |
| III-10 | NO$_2$ | 1 | CO | NH | — |
| III-11 | m,p-(OMe)$_2$ | 2 | CO | NH | — |
| III-12 | p-Me | 2 | CO | NH | — |
| III-13 | m-Me | 1 | CO | NH | — |

Compound III-2
$^1$H NMR (CDCl$_3$) δ: 1.39 (s, 3H), 1.59 (s, 3H),
  3.36 (d, J=5 Hz, 1H), 3.77 (s, 2H),
  4.07 (d, J=9 Hz, 1H),
  4.89 (dd, J=9 Hz, 5 Hz, 1H),
  7.19–7.34 (m, 5H), 7.46 (s, 1H),
  8.70 (s, 1H), 9.74 (bs, 1H).
MS (FAB) m/z: 71(bp), 435[M+H]$^+$.

Compound III-3
$^1$H NMR (CDCl$_3$) δ: 1.37 (s, 3H), 1.58 (s, 3H),
  2.51–3.26 (m, 4H),
  4.09 (d, J=10 Hz, 1H),
  4.20 (d, J=5 Hz, 1H),
  4.87 (dd, J=10 Hz, 5 Hz, 1H),
  7.16 (s, 5H), 7.48 (s, 1H),
  8.66 (s, 1H), 9.75 (bs, 1H).
MS (FAB) m/z: 105(bp), 449[M+H]$^+$.

Compound III-4
$^1$H NMR (CDCl$_3$) δ: 1.39 (s, 3H), 1.59 (s, 3H),
  3.70 (s, 2H), 3.84 (s, 7H),
  4.08 (d, J=9 Hz, 1H),
  4.88 (dd, J=9 Hz, 5 Hz, 1H),
  6.80 (m, 3H), 7.48 (s, 1H),
  8.70 (bs, 1H), 9.78 (bs, 1H).
MS (FAB) m/z: 151(bp), 495[M+H]$^+$.

Compound III-5
$^1$H NMR (CDCl$_3$) δ: 1.38 (s, 3H), 1.59 (s, 3H),
  3.70 (s, 2H), 3.78 (s, 3H),
  4.06 (d, J=9 Hz, 1H), 4.31 (bs, 1H),
  4.98 (d, J=9 Hz, 1H),
  6.17–7.31 (m, 4H), 7.45 (s, 1H)
  8.70 (s, 1H), 9.76 (bs, 1H).
MS (FAB) m/z: 121(bp), 465[M+H]$^+$.

Compound III-6
$^1$H NMR (CDCl$_3$) δ: 1.21 (s, 3H), 1.42 (s, 3H),
  2.18 (s, 3H), 3.54 (s, 3H),
  3.90 (d, J=9 Hz, 1H),
  4.73 (d, J=9 Hz, 1H),
  7.00 (s, 4H), 7.33 (s, 1H)
  8.58 (s, 1H), 9.62 (bs, 1H).
MS (FAB) m/z: 105(bp), 449[M+H]$^+$.

Compound III-7
$^1$H NMR (CDCl$_3$) δ: 1.48 (s, 3H), 1.69 (s, 3H), 3.81 (s, 2H),
  4.16 (d, J=10 Hz, 1H),
  5.00 (d, J=10 Hz, 1H),
  7.35 (s, 4H), 7.60 (s, 1H)
  8.80 (s, 1H), 9.92 (bs, 1H).
MS (FAB) m/z: 125(bp), 469[M+H]$^+$.

Compound III-8
$^1$H NMR (CDCl$_3$) δ: 1.31 (s, 3H), 1.55 (s, 3H),
  3.99 (d, J=9 Hz, 1H),
  4.73 (d, J=9 Hz, 1H),
  6.96–7.71 (m, 7H), 8.55 (s, 1H),
  9.40 (bs, 1H).
MS (FAB) m/z: 71, 319, 436[M+H]$^+$ (bp).

Compound III-9
$^1$H NMR (CDCl$_3$) δ: 1.38 (s, 3H), 1.58 (s, 3H), 3.74 (s, 2H),
  4.07 (d, J=9 Hz, 1H),
  4.17 (d, J=5 Hz, 1H),
  4.88 (dd, J=5 Hz, 9 Hz, 1H),
  6.84–7.45 (m, 4H), 7.49 (s, 1H), 8.72 (s, 1H), 9.84 (bs, 1H).
MS (FAB) m/z: 109(bp), 453[M+H]$^+$, mp. 153–156° C.

Compound III-10
$^1$H NMR (CDCl$_3$) δ: 1.39 (s, 3H), 1.60 (s, 3H),
3.25 (d, J=5 Hz, 1H),
3.87 (s, 2H), 4.08 (d, J=10 Hz, 1H),
4.89 (dd, J=5 Hz, 10 Hz, 1H),
7.35–7.68 (m, 3H), 8.03–8.35 (m, 2H),
8.70 (s, 1H), 9.95 (bs, 1H).
MS (EI) m/z: 136(bp), 479[M+H]$^+$, mp. 171–174° C.

Compound III-11
$^1$H NMR (CDCl$_3$) δ: 1.39 (s, 3H), 1.59 (s, 3H),
2.50–3.17 (m, 4H), 3.80 (s, 6H),
3.87 (bs, 1H), 4.08 (d, J=10 Hz, 1H),
4.90 (dd, J=4 Hz, 10 Hz, 1H),
6.69 (s, 3H), 7.50 (s, 1H),
8.66 (s, 1H), 9.73 (bs, 1H).
MS (FAB) m/z: 185(bp), 508[M+H]$^+$.

Compound III-12
$^1$H NMR (CDCl$_3$) δ: 1.40 (s, 3H), 1.60 (s, 3H),
2.50–3.20 (m, 4H), 3.74 (s, 3H),
4.10 (d, J=9 Hz, 1H), 4.30 (bs, 1H),
4.90 (dd, J=4 Hz, 9 Hz, 1H),
6.65–7.25 (m, 4H), 7.52 (s, 1H),
8.70 (s, 1H), 9.78 (bs, 1H).
MS (FAB) m/z: 121(bp), 479[M+H]$^+$, mp. 169–171° C.

Compound III-13
$^1$H NMR (CDCl$_3$) δ: 1.34 (s, 3H), 1.54 (s, 3H),
3.72 (s, 2H), 3.75 (s, 3H),
4.03 (d, J=9 Hz, 1H),
4.32 (d, J=5 Hz, 1H),
4.85 (dd, J=5 Hz, 9 Hz, 1H),
6.65–6.97 (m, 3H), 7.09–7.42 (m, 1H),
7.44 (s, 1H), 8.71 (s, 1H), 9.80 (bs, 1H).
MS (FAB) m/z: 121(bp), 465[M+H]$^+$, mp. 141–142° C.

Referential Example 3

Synthesis of 6-(benzoylamino)-3,4-epoxy-3,4-dihydro-2,2-dimethyl-7-nitro-2H-1-benzopyran (II-1)

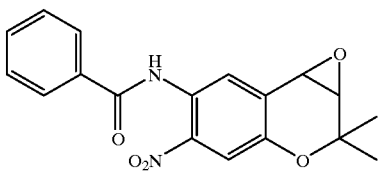

A mixed solution of a 1,4-dioxane (5 mL) and water (2.5 mL) in which a 6-(benzoylamino)-3-bromo-3,4-dihydro-2,2-dimethyl-7-nitro-2H-1-benzopyran-4-ol (III-1) (223 mg, 0.53 mmol) was dissolved was added with a sodium hydroxide (25.5 mg, 1.2 eq.) and stirred at room temperature for one hour. After the solution was diluted with water, the resulting mixture was extracted with an ethyl acetate and the organic layer was washed with an aqueous saturated sodium chloride solution, the layer was dried over a sodium sulfate anhydride. After the solvent was distilled off, the obtained residue was purified through silica gel column chromatography (hexane:ethyl acetate=4:1) to obtain the intended product (147 mg, 81%) as a yellow solid.
$^1$H NMR (CDCl$_3$) δ: 1.29 (s, 3H), 1.60 (s, 3H),
3.05 (d, J=4 Hz, 1H),
3.98 (d, J=4 Hz, 1H),
7.40–8.10 (m, 6H), 8.97 (s, 1H).
MS (FAB) m/z: 105(bp), 341[M+H]$^+$.

The following compounds were obtained in the method of the Referential Example 3 using the compounds III-2 to III-13 instead of the compound III-1.

| Compound | R$^9$ | n | X | Y | Z |
|---|---|---|---|---|---|
| II-2 | H | 1 | CO | NH | — |
| II-3 | H | 2 | CO | NH | — |
| II-4 | m,p-(OMe)$_2$ | 1 | CO | NH | — |
| II-5 | p-OMe | 1 | CO | NH | — |
| II-6 | p-Me | 1 | CO | NH | — |
| II-7 | p-Cl | 1 | CO | NH | — |
| II-8 | H | 0 | NH | CO | NH |
| II-9 | F | 1 | CO | NH | — |
| II-10 | NO$_2$ | 1 | CO | NH | — |
| II-11 | m,p-(OMe)$_2$ | 2 | CO | NH | — |
| II-12 | p-OMe | 2 | CO | NH | — |
| II-13 | m-OMe | 1 | CO | NH | — |

Compound II-2
MS (FAB) m/z: 237(bp), 355[M+H]$^+$.

Compound II-3
$^1$H NMR (CDCl$_3$) δ: 1.25 (s, 3H), 1.35 (s, 3H),
2.53–3.25 (m, 4H),
3.46 (d, J=4 Hz, 1H),
3.87 (d, J=4 Hz, 1H),
7.15 (s, 5H), 7.48 (s, 1H)
8.66 (s, 1H), 9.85 (bs, 1H).
MS (FAB) m/z: 105(bp), 369[M+H]$^+$.

Compound II-4
$^1$H NMR (CDCl$_3$) δ: 1.21 (s, 3H), 1.54 (s, 3H),
3.47 (d, J=4 Hz, 1H),
3.67 (s, 2H), 3.75–3.98 (m, 7H),
6.78 (s, 3H), 7.41 (s, 1H)
8.65 (s, 1H), 9.87 (bs, 1H).
MS (FAB) m/z: 151(bp), 415[M+H]$^+$.

Compound II-5
$^1$H NMR (CDCl$_3$) δ: 1.21 (s, 3H), 1.53 (s, 3H),
3.50 (d, J=4 Hz, 1H),
3.68 (s, 2H), 3.74 (s, 3H),
3.90 (d, J=4 Hz, 1H),
6.77–7.37 (m, 4H), 7.49 (s, 1H)
8.72 (s, 1H), 9.93 (bs, 1H).
MS (FAB) m/z: 121(bp), 385[M+H]$^+$.

Compound II-6
$^1$H NMR (CDCl$_3$) δ: 1.22 (s, 3H), 1.56 (s, 3H),
2.33 (s, 3H), 3.47 (d, J=4 Hz, 1H), 3.72 (s, 2H), 3.90 (d, J=4 Hz, 1H),
7.18 (s, 4H), 7.50 (s, 1H),
8.74 (s, 1H), 9.95 (bs, 1H).
MS (FAB) m/z: 105(bp), 369[M+H]$^+$.

Compound II-7

$^1$H NMR (CDCl$_3$) δ: 1.21 (s, 3H), 1.54 (s, 3H),
3.47 (d, J=4 Hz, 1H), 3.71 (s, 2H),
3.88 (d, J=4 Hz, 1H),
7.23 (s, 4H), 7.48 (s, 1H)
8.67 (s, 1H), 9.92 (bs, 1H).
MS (FAB) m/z: 125(bp), 389[M+H]$^+$.

Compound II-8

MS (FAB) m/z: 237(bp), 356[M+H]$^+$.

Compound II-9

$^1$H NMR (CDCl$_3$) δ: 1.24 (s, 3H), 1.55 (s, 3H),
3.50 (d, J=4 Hz, 1H),
3.74 (s, 2H), 3.88 (d, J=4 Hz, 1H),
6.80–7.45 (m, 4H), 7.48 (s, 1H),
8.69 (s, 1H), 9.94 (bs, 1H).
MS (FAB) m/z: 109(bp), 373[M+H]$^+$.

Compound II-10

$^1$H NMR (CDCl$_3$) δ: 1.35 (s, 3H), 1.55 (s, 3H),
3.50 (d, J=5 Hz, 1H),
3.87–3.93 (m, 3H), 7.40–8.70 (m, 6H),
10.15 (bs, 1H).
MS (EI) m/z: 83(bp), 399[M$^+$].

Compound II-11

$^1$H NMR (CDCl$_3$) δ: 1.24 (s, 3H), 1.55 (s, 3H),
2.53–3.18 (m, 4H),
3.48 (d, J=4 Hz, 1H),
3.82 (s, 6H), 3.89 (d, J=4 Hz, 1H),
6.71 (s, 3H), 7.49 (s, 1H),
8.67 (s, 1H), 9.87 (bs, 1H).
MS (FAB) m/z: 151(bp), 429[M+H]$^+$, mp. 93–95° C.

Compound II-12

$^1$H NMR (CDCl$_3$) δ: 1.23 (s, 3H), 1.54 (s, 3H),
2.47–3.17 (m, 4H),
3.46 (d, J=4 Hz, 1H),
3.61 (s, 3H), 3.87 (d, J=4 Hz, 1H),
6.57–7.22 (m, 4H), 7.47 (s, 1H),
8.66 (s, 1H), 9.82 (bs, 1H).
MS (FAB) m/z: 71(bp), 399[M+H]$^+$, mp. 136–137° C.

Compound II-13

$^1$H NMR (CDCl$_3$) δ: 1.21 (s, 3H), 1.54 (s, 3H),
3.48 (d, J=4 Hz, 1H),
3.76 (s, 3H), 3.88 (d, J=4 Hz, 1H),
6.60–6.98 (m, 3H), 7.08–7.40 (m, 1H),
7.42 (s, 1H), 8.68 (s, 1H), 9.90 (bs, 1H).
MS (FAB) m/z: 121(bp), 385[M+H]$^+$.

Referential Example 4

Synthesis of 6-(4'-phenylphenylacetylamino)-3,4-epoxy-3,4-dihydro-2,2-dimethyl-7-nitro-2H-1-benzopyran (II-14)

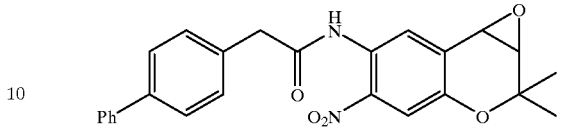

A chloroform (10 mL) solution of the compound IV-15 (1.6 g, 3.86 mmol) was added with a 3-chloroperbenzoic acid (1.46 g, 2.2 eq.) at 0° C. and stirred at 0° C. for four hours and at room temperature for twenty four hours. After the mixture was added with an aqueous saturated sodium hydrogencarbonate solution, the mixture was extracted with a chloroform and dried over a sodium sulfate anhydride. After the solvent was distilled off, the obtained residue was purified through silica gel column chromatography (hexane:ethyl acetate=3:1) to obtain the intended product (1.47 g, 89%) as a pale yellow solid.

$^1$H NMR (CDCl$_3$) δ: 1.24 (s, 3H), 1.59 (s, 3H),
3.47 (d, J=4 Hz, 1H),
3.79 (s, 2H), 3.89 (d, J=4 Hz, 1H),
7.19–7.74 (m, 10H), 8.75 (s, 1H),
9.92 (bs, 1H).
MS (FAB) m/z: 167(bp), 430[M$^+$], mp. 171–174° C.

The following compounds were obtained in the method of the Referential Example 4 by using the compound IV-14 and IV-20 instead of the compound IV-15.

| Compound | R$^9$ | n | X | Y | Z |
|---|---|---|---|---|---|
| II-15 | o-OMe | 1 | CO | NH | — |
| II-16 | p-NHAc | 1 | CO | NH | — |

Compound II-15

$^1$H NMR (CDCl$_3$) δ: 1.21 (s, 3H), 1.54 (s, 3H),
3.45 (d, J=4 Hz, 1H),
3.75 (s, 2H), 3.85 (s, 3H),
3.87 (d, J=4 Hz, 1H),
6.73–7.43 (m, 4H), 7.45 (s, 1H),
8.71 (s, 1H), 10.05 (bs, 1H).
MS (FAB) m/z: 121(bp), 385[M+H]$^+$, mp. 134–135° C.

Compound II-16

$^1$H NMR (CDCl$_3$) δ: 1.24 (s, 3H), 1.58 (s, 3H), 2.19 (s, 3H),
3.53 (d, J=4 Hz, 1H),
3.77 (s, 2H), 3.95 (d, J=4 Hz, 1H),
7.20 (bs, 1H), 7.31 (d, J=8 Hz, 2H),
7.56–7.59 (m, 3H), 8.82 (s, 1H),
10.04 (bs, 1H).
MS (FAB) m/z: 106(bp), 412[M+H]$^+$.

The following compounds were obtained in the method of the Referential Example 4 by using the compound IV-22 instead of the compound IV-15.

Compound II-17

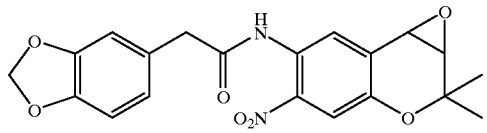

¹H NMR (CDCl₃) δ: 1.22 (s, 3H), 1.54 (s, 3H),
3.45 (d, J=4 Hz, 1H), 3.64 (s, 2H),
3.88 (d, J=4 Hz, 1H), 5.91 (s, 2H),
6.73 (s, 3H), 7.50 (s, 1H),
8.72 (s, 1H), 9.96 (bs, 1H).
MS (FAB) m/z: 135(bp), 399[M+H]⁺, mp. 146–147° C.

The following compounds were obtained in the method of the Referential Example 4 by using the compound IV-23 instead of the compound IV-15.

Compound II-18

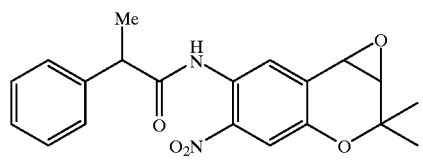

¹H NMR (CDCl₃) δ: 1.21 (s, 3H), 1.55 (s, 3H),
1.61 (d, J=7 Hz, 3H),
3.46 (d, J=4 Hz, 1H),
3.78 (q, J=7 Hz, 1H),
3.85 (d, J=4 Hz, 1H),
7.18–7.41 (m, 5H), 7.44 (s, 1H),
8.70 (s, 1H), 9.94 (bs, 1H).
MS (EI) m/z: 105(bp), 368[M⁺].

The following compounds were obtained in the method of the Referential Example 4 by using the compound IV-26 instead of the compound IV-15.

Compound II-19

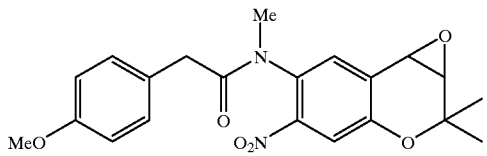

¹H NMR (CDCl₃) δ: 1.32 (s, 3H), 1.63 (s, 3H),
3.21 (s, 3H), 3.24–3.81 (m, 7H),
6.76–6.87 (m, 2H), 6.87–6.91 (m, 2H),
7.02 (s, 1H), 7.42 (s, 1H).
MS (EI) m/z: 352(bp), 398[M⁺].

Referential Example 5

Synthesis of 6-(4'-methoxyphenylacetylamino)-3,4-epoxy-3,4-dihydro-2,2-dimethyl-7-nitro-2H-1benzopyran (II-20)

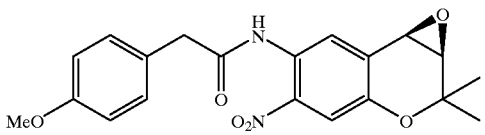

An ethyl acetate (180 mL) solution of the compound IV-5 (3.5 g, 9.5 mmol) was added with a salen manganese complex (the compound 45) (492.1 mg, 5 mol %) and a 4-phenylpyridine N-oxide (162.7 mg, 10 mol %). After the temperature was cooled to 0° C., the mixture was added with a sodium hypochlorite (1.645 mol/l) solution (6.35 ml, 1.1. eq.) and the mixture was stirred at 0° C. for one hour. The mixture was added with water and extracted with an ethyl acetate. After the extracted organic layer was combined and washed with a saturated saline water, the resulting product was dried over sodium sulfuric anhydride. After the solvent was distilled off, the obtained residue was purified through silica gel column chromatography (hexane:ethyl acetate= 3:1) to obtain the intended product (2.69 g, 74%) as yellow crystals.

(45)

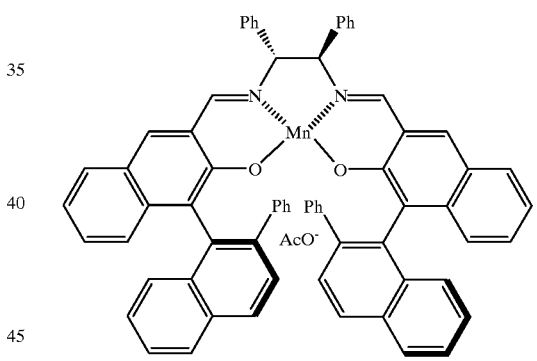

Spectral data was completely accorded with those of the compound II-5.

The following compounds were obtained in the method of the Referential Example 4 by using the compound IV-16 instead of the compound IV-5.

| Compound | R⁹ | n | X | Y | Z |
|---|---|---|---|---|---|
| II-21 | p-OEt | 1 | CO | NH | — |
| II-22 | p-OTBDMS | 1 | CO | NH | — |

-continued

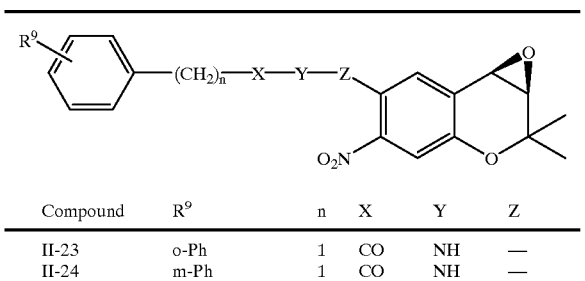

| Compound | R⁹ | n | X | Y | Z |
|---|---|---|---|---|---|
| II-23 | o-Ph | 1 | CO | NH | — |
| II-24 | m-Ph | 1 | CO | NH | — |

TBDMS: tert-butyldimethylsilyl

Compound II-21
$^1$H NMR (CDCl$_3$) δ: 1.24 (s, 3H), 1.40 (t, J=7 Hz, 3H),
1.58 (s, 3H), 3.48 (d, J=4 Hz, 1H),
3.69 (s, 2H), 3.90 (d, J=4 Hz, 1H),
4.00 (q, J=7 Hz, 2H),
6.77–7.36 (m, 4H), 7.50 (s, 1H),
8.74 (s, 1H), 9.94 (bs, 1H).
MS (EI) m/z: 107(bp), 398[M$^+$], mp. 101–103° C.

The following compounds were obtained in the method of the Referential Example 5 by using the compound IV-28 instead of the compound IV-5.

Compound II-22
$^1$H NMR (CDCl$_3$) δ: 0.21 (s, 6H), 1.00 (s, 9H),
1.33 (s, 3H), 1.54 (s, 3H),
3.47 (d, J=5 Hz, 1H), 3.70 (s, 2H),
3.90 (d, J=5 Hz, 1H),
6.87 (d, J=7 Hz, 2H),
7.15 (d, J=7 Hz, 2H),
7.94 (s, 1H), 8.70 (s, 1H),
9.89 (bs, 1H).
MS (EI) m/z: 220(bp), 485[M$^+$].
[α]$^{20}$+4.0° (CHCl$_3$).

The following compounds were obtained in the method of the Referential Example 5 by using the compound IV-18 instead of the compound IV-5.

Compound II-23
$^1$H NMR (CDCl$_3$) δ: 1.24 (s, 3H), 1.57 (s, 3H),
3.52 (d, J=4 Hz, 1H), 3.80 (s, 2H),
3.91 (d, J=4 Hz, 1H),
7.26–7.44 (m, 9H),
7.57 (s, 1H), 8.74 (s, 1H),
9.85 (bs, 1H).
MS (EI) m/z: 167(bp), 430[M$^+$].

The following compounds were obtained in the method of the Referential Example 5 by using the compound IV-19 instead of the compound IV-5.

Compound II-24
$^1$H NMR (CDCl$_3$) δ: 1.23 (s, 3H), 1.57 (s, 3H),
3.52 (d, J=4 Hz, 1H), 3.87 (s, 2H),
3.94 (d, J=4 Hz, 1H),
7.52–7.62 (m, 10H),
8.83 (s, 1H), 10.11 (bs, 1H).
MS (EI) m/z: 167(bp), 431[M+1].

The following compounds were obtained in the method of the Referential Example 5 by using the compound IV-22 instead of the compound IV-5.

Compound II-25

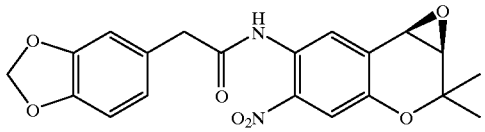

$^1$H NMR (CDCl$_3$) δ: 1.25 (s, 3H), 1.58 (s, 3H),
3.50 (d, J=4 Hz, 1H), 3.68 (s, 2H),
3.92 (d, J=4 Hz, 1H), 5.95 (s, 2H),
6.78 (s, 3H), 7.53 (s, 1H),
8.77 (s, 1H), 9.99 (bs, 1H).
MS (EI) m/z: 135(bp), 398[M$^+$], mp. 135–138° C.

The following compounds were obtained in the method of the Referential Example 5 by using the compound IV-24 instead of the compound IV-5.

Compound II-26

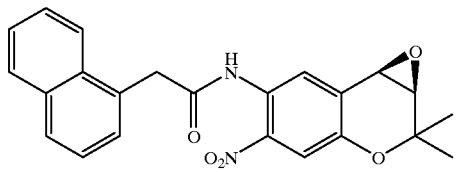

$^1$H NMR (CDCl$_3$) δ: 1.21 (s, 3H), 1.57 (s, 3H),
3.48 (d, J=4 Hz, 1H),
3.90 (d, J=4 Hz, 1H),
4.26 (s, 2H), 7.38–8.09 (m, 8H),
8.78 (s, 1H), 9.96 (bs, 1H).
MS (EI) m/z: 141(bp), 404[M$^+$].

The following compounds were obtained in the method of the Referential Example 5 by using the compound IV-25 instead of the compound IV-5.

Compound II-27

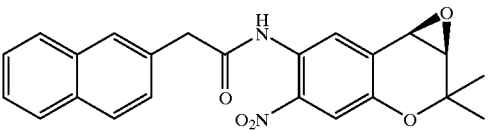

$^1$H NMR (CDCl$_3$) δ: 1.20 (s, 3H), 1.55 (s, 3H),
3.45 (d, J=4 Hz, 1H),
3.87 (d, J=4 Hz, 1H),
3.91 (s, 2H), 7.17–7.97 (m, 8H),
8.74 (s, 1H), 10.02 (bs, 1H).
MS (EI) m/z: 141(bp), 404[M$^+$], mp. 140–142° C.

The following compounds were obtained in the method of the Referential Example 5 by using the compound IV-27 instead of the compound IV-5.

Compound II-28

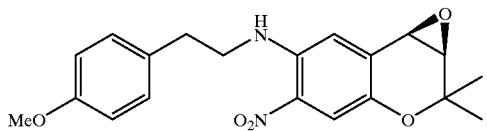

$^1$H NMR (CDCl$_3$) δ: 1.21 (s, 3H), 1.56 (s, 3H),
2.96 (t, J=7 Hz, 2H),
3.49 (d, J=4 Hz, 1H),
3.51–3.53 (m, 2H), 3.79 (s, 3H),
3.84 (d, J=4 Hz, 1H),
6.83–6.88 (m, 2H),
7.18 (d, J=8 Hz, 2H), 7.62 (s, 1H),
7.87 (bs, 1H).
MS (EI) m/z: 370[M$^+$](bp).

The following compounds were obtained in the method of the Referential Example 5 by using the compound IV-29 instead of the compound IV-5.

Compound II-29

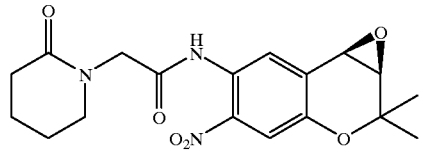

$^1$H NMR (CDCl$_3$) δ: 1.22 (s, 3H), 1.54 (s, 3H),
1.80–2.00 (m, 4H), 2.40–2.60 (m, 2H),
3.32–3.45 (m, 2H),
3.50 (d, J=4.2 Hz, 1H),
3.92 (d, J=4.2 Hz, 1H),
4.17 (s, 2H), 7.51 (s, 1H),
8.71 (s, 1H), 10.40 (bs, 1H).
MS (EI) m/z: 140(bp), 375[M$^+$].

Referential Example 6

Compound II-30

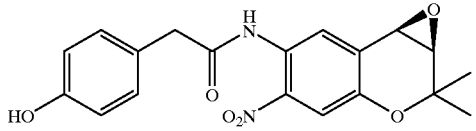

A tetrahydrofuran (0.39 mL) solution of a 6-(4-(t-butyl-dimethylsiloxy)benzoyl)amino-3,4-epoxy-3,4-dihydro-2,2-dimethyl-7-nitro-2H-1-benzopyran (II-22) (39 mg, 0.080 mmol) and a tetrabutylammonium fluoride 1.0 M tetrahydrofuran solution (0.12 mL, 1.5 eq.) were stirred at 0° C. for one hour and at room temperature for one hour. After the mixture was diluted with water, the mixture was extracted with an ethyl acetate. After the solvent was distilled off, the obtained residue was purified through silica gel thin layer chromatography (hexane:ethyl acetate=3:1 ) to obtain the intended product (24 mg, 81%) as an yellow oil.
$^1$H NMR (CDCl$_3$) δ: 1.24 (s, 3H), 1.57 (s, 3H),
3.53 (d, J=4 Hz, 1H), 3.74 (s, 2H),
3.94 (d, J=4 Hz, 1H),
6.88 (d, J=8 Hz, 2H),
7.20 (d, J=8 Hz, 2H),
7.58 (s, 1H), 8.79 (s, 1H),
16.04 (bs, 1H).
MS (EI) m/z: 370[M$^+$](bp).
[α]$^{20}$+3.8° (CHCl$_3$).

Referential Example 7

Compound II-31

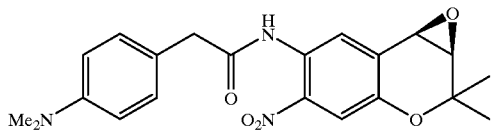

A mixed solution of a 1,4-dioxane (152 mL) and water (76 mL) in which a 6-acetoamido-3,4-epoxy-3,4-dihydro-2,2-dimethyl-7-nitro-2H-1-benzopyran (synthesized according to the method of Evans, J. M., et al., J. Med. Chem. 1984, 27, 1127) (7.6 g, 27 mmol) and sodium hydroxide (5.6 g, 5.0 eq.) were dissolved was stirred at room temperature for four hours. After the mixture was neutralized with hydrochloric acid, the resulting product was diluted by a saturated saline water, extracted with an ethyl acetate and then, dried over a sodium sulfate anhydride. After the solvent was distilled off, the resulting product was recrystallized from a mixed solvent of ethanol and hexane to obtain a 6-amino-3,4-epoxy-3,4-dihydro-2,2-dimethyl-7-nitro-2H-1-benzopyran (1.4 g, 22%) as orange crystals.

A dichloromethane (1.0 mL) solution of a 4-dimethylaminophenyl acetic acid (0.10 g, 0.56 mmol) and DMF (0.01 mL) was added a thionyl chloride (0.07 g, 1 eq.) at 0° C. and stirred at 0° C. for two hours. The mixture was added with a triethylamine (0.08 mL, 1 eq.) at 0° C., and stirred at 0° C. for ten minutes. Then, a DMF (0.7 mL) solution of a 6-amino-3,4-epoxy-3,4-dihydro-2,2-dimethyl-7-nitro-2H-1-benzopyran (66 mg, 0.28 mmol) and a 60% sodium hydride (12 mg, 0.31 mmol) was dropwise added to the stirred solution which was stirred at 0° C. for ten minutes and stirred at 0° C. for two hours. After water was added, the organic layer was extracted and dried over a sodium sulfate anhydride. After the solvent was distilled off, the obtained residue was purified through silica gel thin chromatography (hexane:ethyl acetate=3:1) to obtain the intended product (25 mg, 22%) as a light brown oil.

$^1$H NMR (CDCl$_3$) δ: 1.24 (s, 3H), 1.58 (s, 3H), 2.97 (s, 6H),
3.53 (d, J=4 Hz, 1H), 3.70 (s, 2H),
3.95 (d, J=4 Hz, 1H),
6.77 (d, J=7 Hz, 2H),
7.20 (d, J=7 Hz, 2H),
7.58 (s, 1H), 8.82 (s, 1H),
10.03 (bs, 1H).
MS (EI) m/z: 397[M$^+$](bp).

Referential Example 8

Compound II-32

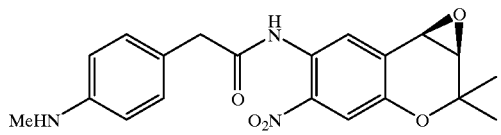

A THF (0.24 mL)-methanol (0.18 mL) mixed solution of a 6-(4-N,N-dimethylaminophenylacetyl-amino)-3,4-epoxy-3,4-dihydro-2,2-dimethyl-7-nitro-2H-1-benzopyran (II-31) (30 mg, 0.075 mmol) and a potassium oxide (36 mg, 8.5 gq.) was added with a THF (0.04 ml) solution of an iodine (43 mg, 2.3 eq.) at 0° C. and stirred at 0° C. for six hours. After dichloromethane (5 mL) was added to the mixture, unsoluble matters were filtered off, the obtained filtrate was added with an aqueous solution of 15% sodium thiosulfate and extracted with a dichloromethane and dried over a sodium sulfuric anhydride. After the solvent was distilled off, the obtained residue was purified through silica gel thin layer chromatography to obtain the intended product (13 mg, 45%) as an yellow oil.

$^1$H NMR (CDCl$_3$) δ: 1.24 (s, 3H), 1.58 (s, 3H), 2.85 (s, 3H),
3.53 (d, J=4 Hz, 1H), 3.69 (s, 2H),
3.95 (d, J=4 Hz, 1H),
6.66 (d, J=7 Hz, 2H),
7.16 (d, J=7 Hz, 2H), 7.58 (s, 1H),
8.82 (s, 1H), 10.03 (bs, 1H).
MS (EI) m/z: 120(bp), 383[M$^+$].
[α]$^{25}$–6.0 (CHCl$_3$).

Example I-1

Synthesis of trans-6-(benzoylamino)-3,4-dihydro-2,2-dimethyl-7-nitro-4-(1-pyrrolidinyl)-2H-1-benzopyran-3-ol

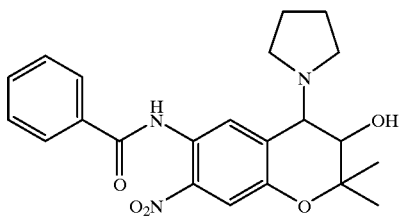

A solution of an ethanol (5 mL) solution of a 6-(benzoylamino)-3,4-epoxy-3,4-dihydro-2,2-dimethyl-7-nitro-2H-1-benzopyran (II-1) (147 mg, 0.43 mmol) was added with a pyrrolidine (0.07 mL) and heated under reflux for two hours. After the mixture was cooled to room temperature, the mixture was concentrated and the obtained residue was purified through silica gel column chromatography (hexane:ethyl acetate=3:1) to obtain the intended product (40.3 mg, 23%) as a brown solid.

$^1$H NMR (CDCl$_3$) δ: 1.25 (s, 3H), 1.53 (s, 3H),
1.79–2.14 (m, 4H),
2.84–3.29 (m, 5H),
3.57 (d, J=10 Hz, 1H),
4.04 (d, J=10 Hz, 1H),
7.34–8.03 (m, 6H),
8.88 (s, 1H), 11.08 (bs, 1H).
MS (FAB) m/z: 105(bp), 412[M+H]$^+$.

Example I-2

Synthesis of a trans-6-(phenylacetylamino)-3,4-dihydro-2,2-dimethyl-7-nitro-4-(1-pyrrolidinyl)-2H-1-benzopyran-3-ol

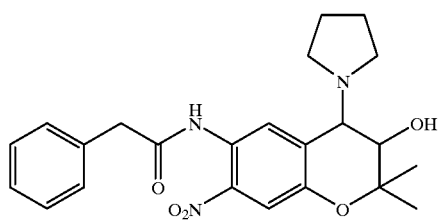

An ethanol (3 mL) solution of the compound II-2 (100 mg, 0.28 mmol) was added a pyrrolidine and heated under reflux for forty five minutes. After the mixture was cooled to room temperature and concentrated, the obtained residue was purified through slica gel column chromatography (hexane:ethyl acetate=2:1) to obtain the intended product (47.8 mg, 40%) as an yellow powder.

$^1$H NMR (CDCl$_3$) δ: 1.27 (s, 3H), 1.57 (s, 3H),
1.85–2.20 (m, 4H),
2.90–3.30 (m, 5H),
3.59 (d, J=10 Hz, 1H), 3.83 (s, 2H),
4.03 (d, J=10 Hz, 1H),
7.23 (s, 1H), 7.35 (s, 5H),
7.54 (s, 1H), 8.70 (bs, 1H).
MS (FAB) m/z: 95(bp), 426[M+H]$^+$.

The following compounds were obtained by using the compounds II-2 to II-13 instead of the compound II-2.

| Compound | R$^9$ | n | X | Y | Z | R$^7$ | R$^8$ |
|---|---|---|---|---|---|---|---|
| I-3 | m,p-(OMe)$_2$ | 1 | CO | NH | — | —(CH$_2$)$_4$— | |
| I-4 | H | 1 | CO | NH | — | Q1 | H |
| I-5 | m,p-(OMe)$_2$ | 1 | CO | NH | — | Et | H |
| I-6 | H | 2 | CO | NH | — | —(CH$_2$)$_4$— | |
| I-7 | H | 2 | CO | NH | — | Et | H |
| I-8 | H | 0 | NH | CO | NH | —(CH$_2$)$_4$— | |
| I-9 | p-OMe | 1 | CO | NH | — | —(CH$_2$)$_4$— | |
| I-10 | p-OMe | 1 | CO | NH | — | Et | H |
| I-11 | m,p-(OMe)$_2$ | 1 | CO | NH | — | i-Pr | H |
| I-12 | m,p-(OMe)$_2$ | 1 | CO | NH | — | c-Pr | H |
| I-13 | p-Me | 1 | CO | NH | — | —(CH$_2$)$_4$— | |
| I-14 | p-Cl | 1 | CO | NH | — | —(CH$_2$)$_4$— | |
| I-15 | p-F | 1 | CO | NH | — | —(CH$_2$)$_4$— | |
| I-16 | m,p-(OMe)$_2$ | 2 | CO | NH | — | Et | H |
| I-17 | p-OMe | 2 | CO | NH | — | Et | H |
| I-18 | p-OMe | 2 | CO | NH | — | i-Pr | H |
| I-19 | p-OMe | 2 | CO | NH | — | —(CH$_2$)$_4$— | |
| I-20 | p-OMe | 1 | CO | NH | — | i-Pr | H |
| I-21 | p-OMe | 1 | CO | NH | — | c-Pr | H |
| I-22 | p-OMe | 1 | CO | NH | — | Me | Me |

-continued

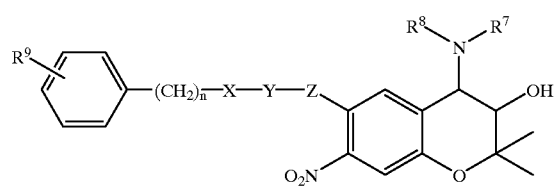

| Compound | R⁹ | n | X | Y | Z | R⁷ | R⁸ |
|---|---|---|---|---|---|---|---|
| I-23 | m-OMe | 1 | CO | NH | — | —(CH₂)₄— | |
| I-24 | m-OMe | 1 | CO | NH | — | Et | H |
| I-25 | m-OMe | 1 | CO | NH | — | c-Pr | H |

Q1:

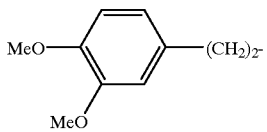

Example I-3
$^1$H NMR (CDCl$_3$) δ: 1.20 (s, 3H), 1.50 (s, 3H),
1.80–2.10 (m, 4H),
2.80–3.26 (m, 4H),
3.01 (d, J=10 Hz, 1H),
3.17 (s, 2H), 3.83 (s, 6H),
3.95 (d, J=10 Hz, 1H),
6.80 (s, 3H), 7.48 (s, 1H),
8.60 (s, 1H), 9.87 (bs, 1H).
MS (FAB) m/z: 151(bp), 486[M+H]$^+$.

Example I-4
$^1$H NMR (CDCl$_3$) δ: 1.15 (s, 3H), 1.46 (s, 3H),
2.24–3.12 (m, 6H),
3.42 (d, J=10 Hz, 1H),
3.66 (d, J=10 Hz, 1H),
3.74 (s, 2H), 3.80 (s, 6H),
6.69 (s, 3H), 7.30 (s, 5H),
7.47 (s, 1H), 8.56 (s, 1H),
9.82 (bs, 1H).
MS (FAB) m/z: 85(bp), 536[M+H]$^+$.

Example I-5
$^1$H NMR (CDCl$_3$) δ: 0.99–1.39 (m, 6H),
1.49 (s, 3H), 2.28–2.95 (m, 4H),
3.50–4.07 (m, 10H),
6.69–6.89 (m, 3H),
7.45 (s, 1H), 8.55 (bs, 1H),
9.95 (bs, 1H).
MS (FAB) m/z: 151(bp), 460[M+H]$^+$.

Example I-6
$^1$H NMR (CDCl$_3$) δ: 1.21 (s, 3H), 1.49 (s, 3H),
1.72–2.07 (m, 4H), 2.47–3.27 (m, 9H),
3.52 (d, J=10 Hz, 1H),
3.96 (d, J=10 Hz, 1H),
7.13 (s, 5H), 7.51 (s, 1H),
8.58 (s, 1H), 9.82 (bs, 1H),
MS (FAB) m/z: 105(bp), 440[M+H]$^+$.

Example I-7
$^1$H NMR (CDCl$_3$) δ: 1.16 (t, J=7 Hz, 3H), 1.20 (s, 3H),
1.50 (s, 3H), 2.25–3.31 (m, 8H),
3.46 (d, J=10 Hz, 1H),
3.67 (d, J=10 Hz, 1H),
7.17 (s, 5H), 7.50 (s, 1H),
8.60 (s, 1H), 9.87 (bs, 1H),
MS (FAB) m/z: 105(bp), 414[M+H]$^+$.

Example I-8
$^1$H NMR (CDCl$_3$) δ: 1.18 (s, 3H), 1.48 (s, 3H),
2.62–3.31 (m, 5H),
3.51 (d, J=10 Hz),
3.90 (d, J=10 Hz),
6.75–7.74 (m, 7H), 8.41 (s, 1H),
9.42 (bs, 1H),
MS (FAB) m/z: 96, 427[M+H]$^+$ (bp).

Example I-9
$^1$H NMR (CDCl$_3$) δ: 1.20 (s, 3H), 1.50 (s, 3H),
1.79–2.12 (m, 4H), 2.69–3.25 (m, 5H),
3.53 (d, J=10 Hz, 1H), 3.70 (s, 2H),
3.80 (s, 3H), 2.96 (d, J=10 Hz, 1H),
6.80–7.38 (m, 4H), 7.54 (s, 1H),
8.71 (s, 1H), 9.92 (bs, 1H),
MS (FAB) m/z: 121(bp), 456[M+H]$^+$.

Example I-10
$^1$H NMR (CDCl$_3$) δ: 1.16 (t, J=7 Hz, 3H),
1.19 (s, 3H), 1.30 (S, 3H),
2.25–3.02 (m, 4H),
3.47 (d, J=10 Hz, 1H),
3.70 (d, J=10 Hz, 1H),
3.70 (s, 2H), 3.79 (s, 3H),
6.79–7.38 (m, 4H), 7.53 (s, 1H),
8.69 (s, 1H), 9.93 (bs, 1H),
MS (FAB) m/z: 121(bp), 430[M+H]$^+$.

Example I-11
$^1$H NMR (CDCl$_3$) δ: 0.99–1.40 (m, 9H),
1.47 (s, 3H), 2.14–2.68 (m, 2H),
3.04–3.61 (m, 3H), 3.68 (s, 2H),
3.85 (s, 6H), 6.83 (s, 3H),
7.46 (s, 1H), 8.75 (s, 1H),
9.94 (bs, 1H),
MS (FAB) m/z: 151(bp), 474[M+H]$^+$.

Example I-12
$^1$H NMR (CDCl$_3$) δ: 0.25–0.68 (m, 4H),
1.21 (s, 3H), 1.51 (s, 3H),
1.99–2.98 (m, 3H),
3.56 (d, J=10 Hz, 1H), 3.70 (s, 2H),
3.74 (d, J=10 Hz, 1H),
3.86 (s, 6H), 6.83 (s, 3H),
7.49 (s, 1H), 8.76 (s, 1H),
9.91 (bs, 1H).
MS (FAB) m/z: 151(bp), 472[M+H]$^+$.

Example I-13
$^1$H NMR (CDCl$_3$) δ: 1.19 (s, 3H), 1.48 (s, 3H),
1.75–2.10 (m, 4H), 2.32 (s, 3H), 2.75–3.25 (m, 5H),
3.49 (d, J=10 Hz, 1H),
3.67 (s, 2H), 3.91 (d, J=10 Hz, 1H),
7.11 (s, 4H), 7.46 (s, 1H),
8.62 (s, 1H), 9.83 (bs, 1H).
MS (FAB) m/z: 105(bp), 440[M+H]⁺.

Example I-14

¹H NMR (CDCl₃) δ: 1.21 (s, 3H), 1.50 (s, 3H),
1.75–2.17 (m, 4H), 2.72–3.22 (m, 5H),
3.52 (d, J=10 Hz, 1H), 3.72 (s, 2H),
4.00 (d, J=10 Hz, 1H),
7.04–7.44 (m, 4H), 7.52 (s, 1H),
8.63 (s, 1H), 9.92 (bs, 1H).
MS (FAB) m/z: 125(bp), 460[M+H]⁺.

Example I-15

¹H NMR (CDCl₃) δ: 1.22 (s, 3H), 1.51 (s, 3H),
1.78–2.10 (m, 4H), 2.70–2.85 (m, 5H),
3.54 (d, J=10 Hz, 1H), 3.74 (s, 2H),
3.97 (d, J=10 Hz, 1H),
6.85–7.50 (m, 4H), 7.54 (s, 1H),
8.67 (s, 1H), 9.95 (bs, 1H).
MS (FAB) m/z: 185, 444[M+H]⁺.

Example I-16

¹H NMR (CDCl₃) δ: 1.18 (t, J=7 Hz, 3H), 1.21 (s, 3H),
1.50 (s, 3H), 2.35–3.22 (m, 8H),
3.40–4.00 (m, 8H), 6.71 (s, 3H),
7.51 (s, 1H), 8.62 (s, 1H),
9.89 (bs, 1H).
MS (FAB) m/z: 151, 474[M+H]⁺.

Example I-17

¹H NMR (CDCl₃) δ: 1.28 (t, J=7 Hz, 3H), 1.21 (s, 3H),
1.51 (s, 3H), 2.39–3.19 (m, 7H),
3.40–3.87 (m, 5H), 6.67–7.28 (m, 4H),
7.53 (s, 1H), 8.64 (s, 1H),
9.88 (bs, 1H).
MS (FAB) m/z: 121(bp), 444[M+H]⁺.

Example I-18

¹H NMR (CDCl₃) δ: 1.08–1.32 (m, 9H), 1.48 (s, 3H),
2.16–3.61 (m, 8H), 3.73 (s, 3H),
6.63–7.26 (m, 4H), 7.48 (s, 1H),
8.72 (s, 1H), 9.86 (bs, 1H),
MS (FAB) m/z: 121(bp), 458[M+H]⁺, mp. 109–111° C.

Example I-19

¹H NMR (CDCl₃) δ: 1.27 (s, 3H), 1.54 (s, 3H),
1.80–2.20 (m, 4H), 2.50–3.35 (m, 9H),
3.57 (d, J=10 Hz, 1H), 3.78 (s, 3H),
4.00 (d, J=10 Hz, 1H),
6.66–7.30 (m, 4H), 7.55 (s, 1H),
8.65 (s, 1H), 9.89 (bs, 1H).
MS (FAB) m/z: 121(bp), 470[M+H]⁺.

Example I-20

¹H NMR (CDCl₃) δ: 1.08–1.33 (m, 9H), 1.48 (s, 3H),
2.14–2.70 (m, 2H), 3.06–3.64 (m, 3H),
3.72 (s, 2H), 3.79 (s, 3H),
6.81–7.42 (m, 4H),
7.52 (s, 1H), 8.55 (s, 1H),
9.97 (bs, 1H).
MS (FAB) m/z: 121(bp), 444[M+H]⁺, mp. 115–117° C.

Example I-21

¹H NMR (CDCl₃) δ: 0.25–0.65 (m, 4H), 1.20 (s, 3H),
1.50 (s, 3H), 2.07–2.95 (m, 3H),
3.68 (m, 2H), 3.73 (s, 3H),
3.81 (s, 3H), 6.77–7.45 (m, 4H),
7.56 (s, 1H), 8.55 (s, 1H),
9.97 (bs, 1H).
MS (FAB) m/z: 121(bp), 442[M+H]⁺.

Example I-22

¹H NMR (CDCl₃) δ: 1.19 (s, 3H), 1.50 (s, 3H),
2.50 (s, 6H), 2.97 (bs, 1H),
3.59–3.94 (m, 7H), 6.81–7.44 (m, 4H),
7.58 (s, 1H), 8.79 (s, 1H),
9.97 (bs, 1H).
MS (FAB) m/z: 121(bp), 430[M+H]⁺, mp. 156–158° C.

Example I-23

¹H NMR (CDCl₃) δ: 1.20 (s, 3H), 1.50 (s, 3H),
1.76–2.10 (m, 4H), 2.50–3.22 (m, 5H),
3.51 (d, J=10 Hz, 1H), 3.72 (s, 2H),
3.80 (s, 3H), 3.96 (d, J=10 Hz, 1H),
6.70–7.00 (m, 3H), 7.12–7.48 (m, 1H),
7.50 (s, 1H), 8.67 (s, 1H), 9.90 (bs, 1H).
MS (FAB) m/z: 121(bp), 456[M+H]⁺.

Example I-24

¹H NMR (CDCl₃) δ: 1.15 (t, J=7 Hz, 3H), 1.18 (s, 3H),
1.50 (s, 3H), 2.36–2.96 (m, 4H),
3.55–3.91 (m, 7H),
6.66–7.01 (m, 3H), 7.14–7.46 (m, 1H),
7.51 (s, 1H), 8.66 (s, 1H), 9.91 (bs, 1H).
MS (FAB) m/z: 121(bp), 430[M+H]⁺, mp. 106–109° C.

Example I-25

¹H NMR (CDCl₃) δ: 0.32–0.66 (m, 4H), 1.20 (s, 3H),
1.49 (s, 3H), 2.08–2.82 (m, 3H),
3.62–3.92 (m, 2H), 3.72 (s, 2H),
3.79 (s, 3H), 6.67–6.97 (m, 3H),
7.12–7.32 (m, 1H), 7.48 (s, 1H),
8.67 (s, 1H), 9.90 (bs, 1H).
MS (FAB) m/z: 185(bp), 442[M+H]⁺.

The following compounds were obtained using the compounds II-10 and II-14 to II-16 instead of the compound II-2.

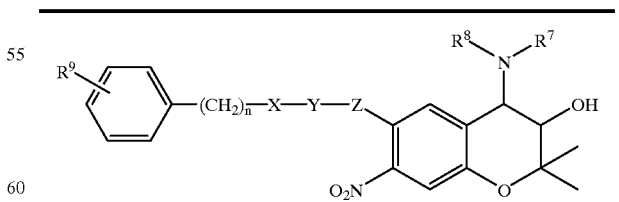

| Compound | R⁹ | n | X | Y | Z | R⁷ | R⁸ |
|---|---|---|---|---|---|---|---|
| I-26 | o-OMe | 1 | CO | NH | — | c-Pr | H |
| I-27 | p-Ph | 1 | CO | NH | — | c-Pr | H |
| I-28 | p-NO₂ | 1 | CO | NH | — | —(CH₂)₄— | |
| I-29 | p-NO₂ | 1 | CO | NH | — | Et | H |

-continued

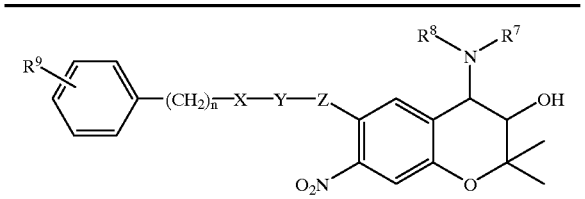

| Compound | R⁹ | n | X | Y | Z | R⁷ | R⁸ |
|---|---|---|---|---|---|---|---|
| I-30 | p-NO₂ | 1 | CO | NH | — | c-Pr | H |
| I-31 | p-NO₂ | 1 | CO | NH | — | i-Pr | H |
| I-32 | p-NHAc | 1 | CO | NH | — | c-Pr | H |
| I-33 | p-NHAc | 1 | CO | NH | — | Et | H |

Example I-26

$^1$H NMR (CDCl$_3$) δ: 0.20–0.67 (m, 4H), 1.19 (s, 3H),
1.49 (s, 3H), 2.17–2.94 (m, 3H),
3.64 (m, 2H), 3.75 (s, 2H), 3.86 (s, 3H),
6.73–7.44 (m, 3H), 7.48 (s, 1H),
8.78 (s, 1H), 10.02 (bs, 1H).
MS (FAB) m/z: 121(bp), 442[M+H]$^+$.

Example I-27

$^1$H NMR (CDCl$_3$) δ: 0.30–0.62 (m, 4H), 1.19 (s, 3H),
1.50 (s, 3H), 2.15–2.70 (m, 3H),
3.62 (d, 2H), 3.79 ( s, 2H) ,
7.15–7.70 (m, 10H), 8.80 (s, 1H),
9.99 (bs, 1H).
MS (FAB) m/z: 109( bp), 524[M+H]$^+$.

Example I-28

$^1$H NMR (CDCl$_3$) δ: 1.21 (s, 3H), 1.51 (s, 3H),
1.19–1.96 (m, 4H), 2.92–2.94 (m, 2H),
3.07–3.11 (m, 2H), 3.22 (s, 1H),
3.57 (d, J=10 Hz, 1H), 3.89 (s, 2H),
3.98 (m, J=10 Hz, 1H),
7.55 (d, J=8 Hz, 2H), 7.63 (s, 1H),
8.27 (d, J=8 Hz, 2H),
8.70 (s, 1H), 10.15 (bs, 1H).
MS (FAB) m/z: 471[M$^+$] (bp).

Example I-29

$^1$H NMR (CDCl$_3$) δ: 1.22 (s, J=7 Hz, 3H), 1 .26 (s, 3H),
1.58 (s, 3H), 2.67–2.76 ( m, 2H),
3.61 (d, J=10 Hz, 1H),
3.75 (d, J=10 Hz, 1H), 3.97 (s, 2H),
7.33 (s, 3H), 7.61 (d, J=8 Hz, 2H),
8.33 (d, J=8 Hz, 2H), 8.75 (s, 1H),
10.23 (bs, 1H).
MS (FAB) m/z: 445[M+H]$^+$(bp).

Example I-30

$^1$H NMR (CDCl$_3$) δ: 0.41–0.53 (m, 4H), 1.20 (s, 3H),
1.52 (s, 3H), 2.33–2.36 (m, 1H),
3.65 (d, J=10 Hz, 1H),
3.72 (d, J=10 Hz, 1H), 3.91 (s, 2H),
7.55 (d, J=9 Hz, 2H),
7.64 (s, 1H), 8.28 (d, J=9 Hz, 2H),
8.84 (s, 1H), 10.20 (bs, 1H).
MS (FAB) m/z: 90(bp), 457[M+H]$^+$.

Example I-31

$^1$H NMR (CDCl$_3$) δ: 1.15 (s, 3H), 1.24–1.26 (m, 6H),
1.50 (s, 3H), 3.27–3.35 (m, 2H),
3.60 (d, J=9 Hz, 1H), 3.90 (s, 2H),
7.55 (d, J=9 Hz, 2H), 7.60 (s, 1H),
8.25–8.28 (m, 2H), 8.82 (s, 1H),
10.18 (bs, 1H).
MS (FAB) m/z: 185(bp), 459[M+H]$^+$.

Example I-32

$^1$H NMR (CDCl$_3$) δ: 0.41–0.54 (m, 4H), 1.20 (s, 3H), 1.51 (s,
3H), 2.19 (s, 3H), 2.35–2.37 (m, 1H),
2.92 (s, 1H), 3.64 (d, J=9 Hz, 1H),
3.71 (d, J=10 Hz, 1H), 3.77 (s, 2H),
7.19 (bs, 1H), 7.30–7.32 (m, 2H),
7.55–7.59 (m, 3H), 8.97 (s, 1H),
10.01 (bs, 1H).
MS (FAB) m/z: 106(bp), 469[M+H]$^+$.

Example I-33

$^1$H NMR (CDCl$_3$) δ: 1.13–1.17 (m, 3H), 1.19 (s, 3H),
1.50 (s, 3H), 2.18 (s, 3H),
2.62–2.77 (m, 2H),
3.55 (d, J=10 Hz, 1H),
3.79 (d, J=10 Hz, 1H), 3.75 (s, 2H),
7.26–7.31 (m, 3H), 7.55–7.57 (m, 3H),
8.70 (s, 1H), 9.98 (bs, 1H).
MS (FAB) m/z: 457[M$^+$] (bp).

The following compounds were obtained using the compound II-17 instead of the compound II-2.

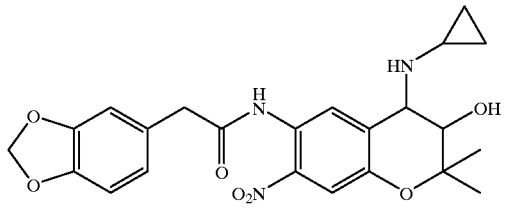

Example I-34

$^1$H NMR (CDCl$_3$) δ: 0.32–0.67 (m, 4H), 1.19 (s, 3H),
1.50 (s, 3H), 2.16–2.82 (m, 3H),
3.56–3.77 (m, 4H), 5.90 (s, 2H),
6.76 (s, 3H), 7.50 (s, 1H),
8.79 (s, 1H), 9.96 (bs, 1H).
MS (FAB) m/z: 135(bp), 456[M+H]$^+$, mp. 140–142° C.

The following compounds were obtained using the compound II-18 instead of the compound II-2.

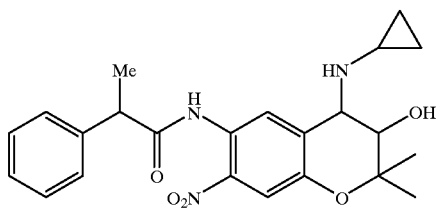

Example I-35
$^1$H NMR (CDCl$_3$) δ: 0.28–0.65 (m, 4H), 1.18 (s, 3H),
1.48 (s, 3H), 1.62 (d, J=7 Hz, 3H),
2.15–2.90 (m, 3H), 3.47–4.03 (m, 3H),
7.10–7.40 (m, 5H), 7.47 (s, 1H),
8.80 (s, 1H), 9.95 (bs, 1H).
MS (FAB) m/z: 105(bp), 426[M+H]$^+$.

The following compounds were obtained using the compound II-19 instead of the compound II-2.

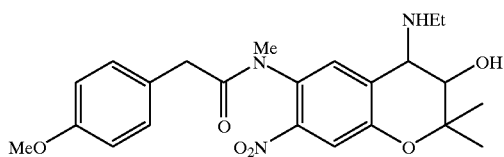

Example I-36
$^1$H NMR (CDCl$_3$) δ: 1.50 (t, J=7 Hz, 3H), 1.25 (s, 3H),
1.51 (s, 3H), 2.05–2.93 (m, 2H),
3.25–3.65 (m, 10H), 3.71 (s, 3H),
6.60–7.40 (m, 6H).
MS (FAB) m/z: 121(bp), 444[M$^+$].

The following compounds were obtained using the compounds II-20 to II-24 and II-30 to II-32 instead of the compound II-2.

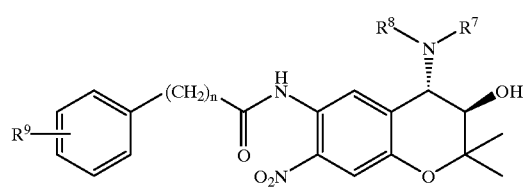

| Compound | R$^9$ | n | R$^7$ | R$^8$ |
|---|---|---|---|---|
| I-37 | p-OMe | 1 | i-Pr | H |
| I-38 | p-OMe | 1 | c-Pr | H |
| I-39 | p-OEt | 1 | c-Pr | H |
| I-40 | p-OTBDMS | 1 | c-Pr | H |
| I-41 | p-OH | 1 | c-Pr | H |
| I-42 | p-NMe$_2$ | 1 | c-Pr | H |
| I-43 | p-OMe | 2 | c-Pr | H |
| I-44 | m-OMe | 1 | c-Pr | H |
| I-45 | m,p-(OMe)$_2$ | 2 | c-Pr | H |
| I-46 | p-NO$_2$ | 1 | c-Pr | H |
| I-47 | o-Ph | 1 | c-Pr | H |
| I-48 | m-Ph | 1 | c-Pr | H |
| I-49 | p-NHMe | 1 | c-Pr | H |

TBDMS: tert-butyldimethylsilyl

Example I-37
$^1$H NMR (CDCl$_3$) δ: 1.08–1.32 (m, 9H), 1.47 (s, 3H),
2.28–2.69 (m, 2H), 3.03–3.57 (m, 3H),
3.67 (s, 2H), 3.77 (s, 3H),
6.75–7.35 (m, 4H), 7.45 (s, 1H),
8.77 (s, 1H),
9.90 (bs, 1H).
MS (FAB) m/z: 121(bp), 444[M+H]$^+$, mp. 117–118° C.
[α]$^{25}$+10.69° (CHCl$_3$)

Example I-38
$^1$H NMR (CDCl$_3$) δ: 0.32–0.65 (m, 4F), 1.19 (s, 3H),
1.49 (s, 3H), 2.10–2.82 (m, 3H),
3.64 (m, 2H), 3.68 (s, 2H),
3.77 (s, 3H), 6.75–7.37 (m, 4H),
7.52 (s, 1H), 8.80 (s, 1H),
9.91 (bs, 1H).
MS (FAB) m/z: 121(bp), 444[M+H]$^+$, mp. 103–104° C.
[α]$^{25}$−7.53° (CHCl$_3$).

Example I-39
$^1$H NMR (CDCl$_3$) δ: 0.35–0.60 (m, 4H), 1.19 (s, 3H),
1.40 (t, J=7 Hz, 3H),
1.50 (s, 3H), 2.18–2.80 (m, 3H),
3.68–3.85 (m, 4H),
4.08 (q, J=7 Hz, 2H),
6.78–7.39 (m, 4H), 7.52 (s, 1H),
8.81 (s, 1H), 9.92 (bs, 1H).
MS (FAB) m/z: 107(bp), 456[M+H]$^+$.

Example I-40
$^1$H NMR (CDCl$_3$) δ: 0.24 (s, 6H), 0.48–0.58 (m, 4H),
1.00 (s, 9H), 1.20 (s, 3H),
1.51 (s, 3H), 2.50–2.60 (m, 1H),
3.65–3.71 (m, 4H),
6.80 (d, J=9 Hz, 2H),
7.15 (d, J=9 Hz, 2H),
7.75 (s, 1H), 8.80 (s, 1H),
9.88 (bs, 1H).
MS (EI) m/z: 524(bp), 542[M$^+$].

Example I-41
$^1$H NMR (CDCl$_3$) δ: 0.38–0.51 (m, 4H), 1.19 (s, 3H),
1.50 (s, 3H), 2.33–2.35 (m, 1H),
3.64–3.70 (m, 2H),
3.74 (s, 2H), 6.87 (m, 2H),
7.19 (d, J=7 Hz, 2H), 7.59 (s, 1H),
8.85 (s, 1H), 10.02 (bs, 1H).
MS (EI) m/z: 108(bp), 427[M$^+$].

Example I-42
$^1$H NMR (CDCl$_3$) δ: 0.38–0.58 (m, 4H), 1.19 (s, 3H),
1.50 (s, 3H), 2.36–2.37 (m, 1H),
2.96 (s, 6H), 3.62–3.69 (m, 4H),
6.76 (d, J=6 Hz, 2H),
7.20 (d, J=6 Hz, 2H),
7.58 (s, 1H), 8.88 (s, 1H),
10.01 (bs, 1H).
MS (EI) m/z: 122(bp), 455[M$^+$].

Example I-43
$^1$H NMR (CDCl$_3$) δ: 0.36–0.53 (m, 4H), 1.18 (s, 3H),
1.48 (s, 3H), 2.32–2.37 (m, 1H),
2.70 (m, 2H), 2.98 (m, 2H), 3.62 (d, J=10 Hz, 1H),
3.70 (d, J=10 Hz, 1H),
6.80 (d, J=9 Hz, 2H),
7.12 (d, J=9 Hz, 2H), 7.58 (s, 1H),
8.81 (s, 1H), 9.96 (bs, 1H).
MS (EI) m/z: 440(bp), 456[M⁺].

Example I-44
[α]²⁰–9.0° (CHCl₃).

Example I-45
¹H NMR (CDCl₃) δ: 0.39–0.56 (m, 4H), 1.26 (s, 3H),
1.52 (s, 3H), 2.36–2.41 (m, 1H),
2.77 (t, J=8 Hz, 2H),
3.03 (t, J=8 Hz, 2H),
3.72 (d, J=10 Hz, 1H),
3.74 (d, J=10 Hz, 1H),
3.85 (s, 3H), 3.86 (s, 3H),
6.77–6.79 (m, 3H), 7.63 (s, 1H),
8.86 (s, 1H), 10.03 (bs, 1H).
MS (EI) m/z: 469(bp), 486[M⁺].

Example I-46
[α]²⁰–9.8° (CHCl₃).

Example I-47
¹H NMR (CDCl₃) δ: 0.37–0.53 (m, 4H), 1.19 (s, 3H),
1.50 (s, 3H), 2.29–2.34 (m, 1H),
3.64 (d, J=10 Hz, 1H),
3.69 (d, J=10 Hz, 1H),
3.79 (s, 2H), 7.25–7.43 (m, 9H),
7.58 (s, 1H), 8.79 (s, 1H),
9.81 (bs, 1H).
MS (EI) m/z: 470(bp), 488[M⁺].
[α]²⁵–2.3° (CHCl₃).

Example I-48
¹H NMR (CDCl₃) δ: 0.37–0.53 (m, 4H), 1.18 (s, 3H),
1.49 (s, 3H), 2.33–2.38 (m, 1H),
3.63 (d, J=10 Hz, 1H),
3.70 (d, J=10 Hz, 1H),
3.85 (s, 2H), 7.24–7.61 (m, 10H),
8.87 (s, 1H), 10.08 (bs, 1H).
MS (EI) m/z: 470(bp), 488[M⁺].
[α]²⁰–8.4° (CHCl₃).

Example I-49
¹H NMR (CDCl₃) δ: 0.35–0.53 (m, 4H), 1.19 (s, 3H),
1.51 (s, 3H), 2.34–2.39 (m, 1H),
2.84 (s, 3H), 3.62–3.72 (m, 4H),
6.59–6.66 (m, 2H),
7.14–7.16 (m, 2H),
7.58 (s, 1H), 8.88 (s, 1H),
10.01 (bs, 1H).
MS (EI) m/z: 440[M⁺] (bp).

The following compounds were obtained by using the compound II-25 instead of the compound II-2.

Example I-50

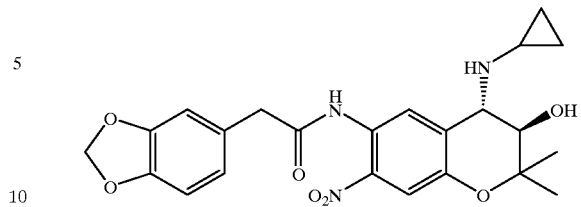

¹H NMR (CDCl₃) δ: 0.29–0.66 (m, 4H), 1.20 (s, 3H),
1.49 (s, 3H), 2.09–2.79 (m, 3H),
3.59–3.77 (m, 4H), 5.90 (s, 2H),
6.76 (s, 3H), 7.51 (s, 1H),
8.79 (s, 1H), 9.96 (bs, 1H).
MS (EI) m/z: 135(bp), 455[M⁺].

The following compounds were obtained by using the compounds II-26 instead of the compound II-2.

Example I-51

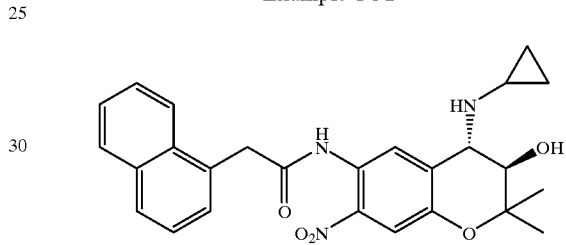

¹H NMR (CDCl₃) δ: 0.32–0.62 (m, 4H), 1.12 (s, 3H),
1.43 (s, 3H), 2.32 (m, 1H),
2.84 (m, 1H), 3.57 (m, 2H),
4.17 (s, 2H), 7.32–8.02 (m, 8H),
8.78 (s, 1H), 9.89 (bs, 1H).
MS (FAB) m/z: 141(bp), 462[M+H]⁺, mp. 185–188° C.

The following compounds were obtained by using the compound II-26 instead of the compound II-2.

Example I-52

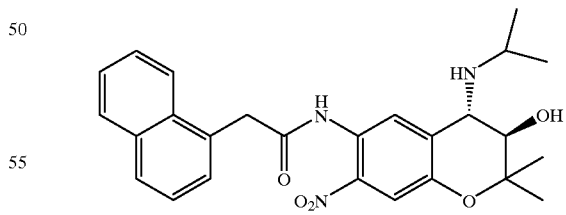

¹H NMR (CDCl₃) δ: 1.08–1.33 (m, 9H), 1.45 (s, 3H),
2.21–2.66 (m, 2H), 3.01–3.71 (m, 3H),
4.18 (s, 2H), 7.24–8.14 (m, 8H),
8.77 (s, 1H), 9.86 (bs, 1H).
MS (EI) m/z: 141(bp), 463[M⁺].

The following compounds were obtained by using the compound II-27 instead of the compound II-2.

Example I-53

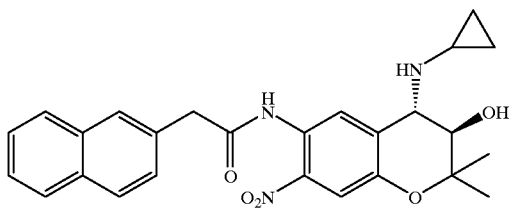

$^1$H NMR (CDCl$_3$) δ: 0.21–0.61 (m, 4H), 1.16 (s, 3H),
1.46 (s, 3H), 2.01–2.71 (m, 3H),
3.61 (m, 2H), 3.89 (s, 2H),
7.14–7.91 (m, 8H), 8.76 (s, 1H),
9.99 (bs, 1H).
MS (FAB) m/z: 141(bp), 462[M+H]$^+$.

The following compounds were obtained by using the compound II-28 instead of the compound II-2.

Example I-54

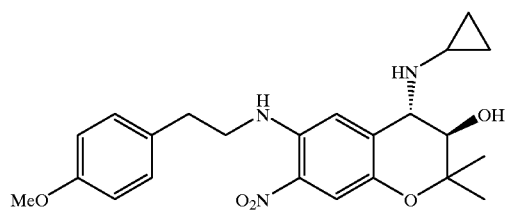

$^1$H NMR (CDCl$_3$) δ: 0.39–0.55 (m, 4H), 1.18 (s, 3H),
1.48 (s, 3H), 2.27–2.32 (m, 1H),
2.96 (t, J=7 Hz, 2H),
3.48–3.53 (m, 2H),
3.66 (d, J=10 Hz, 1H),
3.71 (d, J=10 Hz, 1H),
3.79 (s, 3H), 6.85–6.88 (m, 3H),
7.19 (d, J=9 Hz, 2H), 7.62 (s, 1H),
7.72–7.75 (m, 1H).
MS (EI) m/z: 428[M$^+$].

The following compounds were obtained by using the compound II-29 instead of the compound II-2.

Example I-55

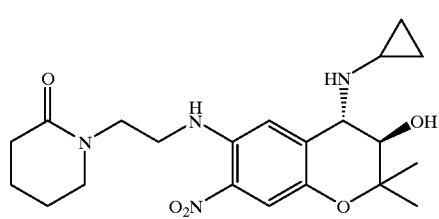

$^1$H NMR (CDCl$_3$) δ: 0.44–0.54 (m, 4H), 1.20 (s, 3H),
1.49 (s, 3H), 1.85–2.05 (m, 4H),
2.35–2.65 (m, 3H), 3.35–3.55 (m, 2H),
3.66 (s, 2H), 4.20 (s, 2H),
7.54 (s, 1H), 8.78 (s, 1H),
10.37 (bs, 1H).

MS (EI) m/z: 113(bp), 432[M$^+$].
[α]$^{25}$–12.7° (CHCl$_3$).

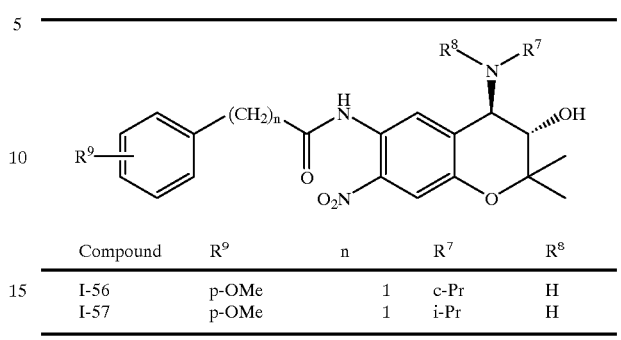

| Compound | R$^9$ | n | R$^7$ | R$^8$ |
|---|---|---|---|---|
| I-56 | p-OMe | 1 | c-Pr | H |
| I-57 | p-OMe | 1 | i-Pr | H |

Example I-56

[α]$^{25}$+7.2° (CHCl$_3$).

Example I-57

[α]$^{25}$–10.9° (CHCl$_3$).

Example I-58

Synthesis of a trans-6-(phenylacetylamino)-3,4-dihydro-2,2-dimethyl-7-nitro-4-(1-pyrrolyl)-2H-1-benzopyran-3-ol

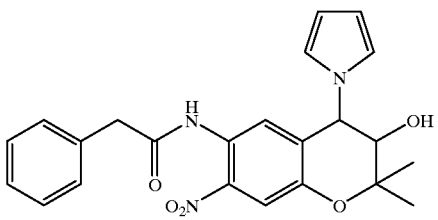

A 6-(phenylacetylamino)-3,4-epoxy-3,4-dihydro-2,2-dimethyl-7-nitro-2H-1-benzopyran (II-2) was added to an ethanol solution (10 mL) of 6.9% ammonia and stirred in a pressure glass tube at 80° C. for four hours. The solvent was distilled off and amino alcohol (117 mg) was obtained as a brown oil.

Then, after the amino alcohol (117 mg) was dissolved in an acetic acid (3 mL), a 2.5-dimethoxytetrahydrofuran (45 μL, 1.1 eq.) was added thereto and heated under reflux for two and half hours. After the temperature of the resulting product was cooled to room temperature, a saturated aqueous sodium hydrogencarbonate solution was added thereto and extracted with an ethyl acetate. The organic layer was combined, washed with water and dried over a sodium sulfate anhydride. After the solvent was distilled off, the obtainted residue was purified through silica gel column chromatography (hexane:ethyl acetate=2:1) to obtain the intended product (about 50 mg) as an orange crystals. The crystals were recrystallized from chloroform/ether to obtain an orange powder (39 mg, 29%, mp. 174–176° C.).

$^1$H NMR (CDCl$_3$) δ: 1.26 (s, 3H), 1.51 (s, 3H),
2.46 (bs, 2H), 3.60 (s, 2H),
3.86 (d, J=10 Hz, 1H),
4.86 (d, 10 Hz, 1H), 6.06–6.27 (m, 2H),
6.49–6.69 (m, 2H), 7.21 (s, 5H),
7.47 (s, 1H), 7.85 (s, 1H), 9.46 (bs, 1H).

MS (FAB) m/z: 422[M+H]⁺.

The following compounds were obtained in the similar method of the Example I-58 by using the compound II-5 instead of the compound II-2.

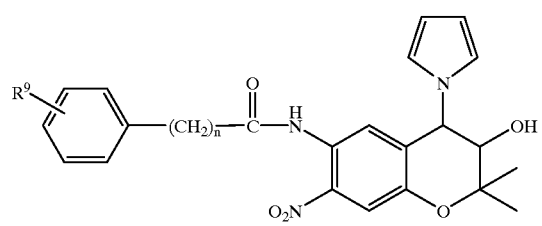

| Compound | R⁹ | n |
|---|---|---|
| I-59 | p-OMe | 1 |
| I-60 | p-OMe | 2 |
| I-61 | m,p-(OMe)₂ | 1 |

Example I-59

¹H NMR (CDCl₃) δ: 1.26 (s, 3H), 1.51 (s, 3H), 2.47 (bs, 1H), 3.56 (s, 2H), 3.74 (s, 3H), 3.87 (d, J=10 Hz, 1H), 4.87 (d, J=10 Hz, 1H), 6.02–6.27 (m, 2H), 6.48–7.28 (m, 6H), 7.53 (s, 1H), 7.92 (s, 1H), 9.55 (bs, 1H).

MS (FAB) m/z: 121(bp), 452[M+H]⁺.

The following compounds were obtained in the similar method of the Example I-58 by using the compound II-12 instead of the compound II-2.

Example I-60

¹H NMR (CDCl₃) δ: 1.29 (s, 3H), 1.54 (s, 3H), 2.32–3.17 (m, 5H), 3.91 (d, J=10 Hz, 1H), 4.91 (d, J=10 Hz, 1H), 6.14–6.34 (m, 2H), 6.58–6.75 (m, 2H), 7.03–7.35 (m, 5H), 7.59 (s, 1H), 7.90 (s, 1H), 9.54 (bs, 1H).

MS (FAB) m/z: 96(bp), 436[M+H]⁺.

The following compounds were obtained in the similar method of the Example I-58 by using the compound II-4 instead of the compound II-2.

Example I-61

¹H NMR (CDCl₃) δ: 1.29 (s, 3H), 1.54 (s, 3H), 2.75 (bs, 1H), 3.59 (s, 2H), 3.87–4.07 (m, 7H), 4.96 (d, J=9 Hz, 1H), 6.17–6.32 (m, 2H), 6.62–6.92 (m, 5H), 7.60 (s, 1H), 7.97 (s, 1H), 9.67 (bs, 1H).

MS (FAB) m/z: 151(bp), 482[M+H]⁺.

Formulation Example 1

| Formulation of Tablets: | |
|---|---|
| Compound | 100 g |
| Lactose | 240 g |
| Crystal cellulose powder | 580 g |
| Corn starch | 330 g |
| Hydroxypropyl cellulose | 80 g |
| CMC-Ca | 140 g |
| Magnesium stearate | 30 g |
| Total | 1500 g |

The above-mentioned components were mixed by a usual method and then tabulated to produce 10000 sugar-coated tablets, each containing 10 mg of the active ingredient.

Formulation Example 2

| Formulation of Capsules: | |
|---|---|
| Compound | 100 g |
| Lactose | 400 g |
| Crystal cellulose powder | 950 g |
| Magnesium stearate | 50 g |
| Total | 1500 g |

The above-mentioned components were mixed by a usual method and then packed in gelatin capsules to obtain 10000 capsules, each containing 10 mg of the active ingredient.

Formulation Example 3

| Formulation of Soft Capsules: | |
|---|---|
| Compound | 100 g |
| PEG 400 | 444 g |
| Saturated fatty acid triglyceride | 1445 g |
| Peppermint oil | 1 g |
| Polysorbate 80 | 10 g |
| Total | 2000 g |

The above-mentioned components were mixed and packed in No. 3 soft gelatin capsules by a usual method to obtain 10000 soft capsules, each containing 10 mg of the active ingredient.

Formulation Example 4

| Formulation of Ointoment: | |
|---|---|
| Compound | 1.0 g |
| Liquid paraffin | 10.0 g |
| Cetanol | 20.0 g |
| White vaseline | 68.4 g |
| Ethyl paraben | 0.1 g |
| λ-menthol | 0.5 g |
| Total | 100.0 g |

The above-mentioned components were mixed by a usual method to obtain 1 g ointment.

Formulation Example 5

| Formulation of Suppositories: | |
|---|---|
| Compound | 10 g |
| Witepsol H15* | 475 g |
| Witepsol W35* | 514 g |
| Polysorbate 80 | 1 g |
| Total | 1000 g |

(*Trade name for triglyceride compound)

The above-mentioned components were melt-mixed by a usual method and poured into suppository containers, followed by cooling for solidification to obtain 1000 suppositories of 1 g, each containing 10 mg of the active ingredient.

Formulation Example 6

| Formulation of Injection: | |
|---|---|
| Compound | 1 mg |
| Distilled water for injection | 5 ml |

The formulation is prepared by dissolving the compound in distilled water whenever it is required.

PHARMACEUTICAL TEST EAMPLES

Effect on the Heart Rate

Methods

Male Hartley guinea-pigs were sacrificed. Their hearts were removed quickly and right atria were isolated from cardiac ventricles. The atria were suspended in an organ bath containing Krebs-Henseleit solution aerated with 95% $O_2$/5% $CO_2$ at 31° C. The diastolic tension applied was 1 g, and the tension developed was measured isometrically using a force displacement transducer. The preparations were equilibrated in the bathing solution with replacement of the solution.

After an equilibration period, isoproterenol was cumulatively added to the preparation to determine the maximum response. The atrium was then washed and equilibrated for 60 minutes with replacement of the solution. Thereafter, each compound (10, 30, 100 and 300 $\mu$M) was cumulatively added to preparation.

Data were expressed as percentages of the maximum response induced by the preceding exposure of isoproterenol.

Result

These compounds caused, in a concentration-dependent manner, a negative chronotropic action as shown in the following table.

TABLE

| Compound | % Change of Heart Rate | | | |
|---|---|---|---|---|
| | 10 $\mu$M | 30 $\mu$M | 100 $\mu$M | 300 $\mu$M |
| I-2 | −9.8 | −28.1 | −37.9 | −41.2 |
| I-3 | −13.2 | −21.5 | −31.4 | −41.3 |
| I-5 | −8.8 | −16.9 | −30.1 | −44.1 |
| I-6 | −11.4 | −17.5 | −32.5 | −74.1 |
| I-7 | −9.8 | −22.9 | −49.7 | −73.9 |
| I-8 | −10.1 | −25.6 | −65.9 | −87.6 |
| I-9 | −8.5 | −14.6 | −25.4 | −65.4 |
| I-10 | −17.9 | −29.2 | −50.0 | −59.4 |
| I-11 | −3.9 | −7.9 | −19.1 | −38.2 |
| I-17 | −8.5 | −11.9 | −14.4 | −19.5 |
| I-18 | −8.2 | −15.8 | −27.8 | −34.8 |

EFFECTS OF THE INVENTION

These compounds are useful drugs for the treatment of heart failure because of their negative chronotropic action.

We claim:

1. A compound of the formula (I):

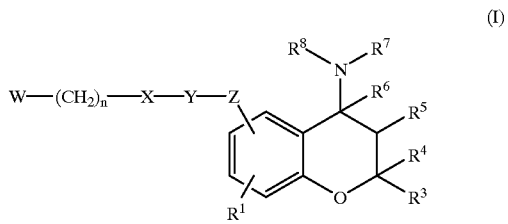

in which, $R^1$ represents a hydrogen atom, a halogen atom, a $C_{1-6}$ alkyl group {said alkyl group is unsubstituted or substituted by a halogen atom, a carboxyl group, a $C_{1-6}$ alkoxy group, a $C_{2-6}$ alkoxycarbonyl group, a hydroxyl group, a formyl group, a cyano group or a nitro group}, a $C_{1-6}$ alkoxy group {said alkoxy group is unsubstituted or substituted by a halogen atom, a carboxyl group, a $C_{2-6}$ alkoxycarbonyl group, a hydroxyl group, a phenyl group (said phenyl group is unsubstituted or substituted by $R^2$ (said $R^2$ represents a halogen atom, a hydroxyl group, a $C_{1-4}$ alkyl group or a $C_{1-4}$ alkoxy group)), a formyl group, a cyano group or a nitro group}, a $C_{3-6}$ cycloalkyl group (said cycloalkyl group is unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$), a formyl group, a cyano group or a nitro group), a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group {said alkylamino group and said di $C_{1-6}$ alkylamino group are unsubstituted or substituted by a halogen atom, a carboxyl group, a $C_{2-6}$ alkoxycarbonyl group, a hydroxyl group, a formyl group, a cyano group or a nitro group}, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, a $C_{1-6}$ alkylcarbonyloxy group, a $C_{1-6}$ alkylurea group, a $C_{1-6}$ alkylthiourea group, an aryl $C_{1-6}$ alkylamino group, a di(aryl $C_{1-6}$ alkyl)amino group, an arylcarbonylamino group, an aryl $C_{1-6}$ alkylcarbonylamino group, an arylsulfonylamino group, an aryl $C_{1-6}$ alkylsulfonylamino group, an aryl $C_{1-6}$ alkylaminocarbonyl group, a di(aryl $C_{1-6}$ alkyl) aminocarbonyl group, an arylcarbonyl group, an aryl $C_{1-6}$ alkylcarbonyl group, an aryloxycarbonyl group, an aryl $C_{1-6}$ alkyloxycarbonyl group, an arylcarbonyloxy group, an aryl $C_{1-6}$ alkylcarbonyloxy group, an arylurea group, an aryl $C_{1-6}$ alkylurea group, an arylthiourea group or an aryl $C_{1-6}$ alkylthiourea group {said aryl $C_{1-6}$ alkylamino group, a di(aryl $C_{1-6}$ alkyl)amino group, an arylcarbonylamino group, an aryl $C_{1-6}$ alkylcarbonylamino group, an arylsulfonylamino group, an aryl $C_{1-6}$ alkylsulfonylamino group, an aryl $C_{1-6}$ alkylaminocarbonyl group, a di(aryl $C_{1-6}$ alkyl)aminocarbonyl group, an arylcarbonyl group, an aryl $C_{1-6}$ alkylcarbonyl group, an aryloxycarbonyl group, an aryl $C_{1-6}$ alkyloxycarbonyl group, an arylcarbonyloxy group, an aryl $C_{1-6}$ alkylcarbonyloxy group, an arylurea group, an aryl $C_{1-6}$ alkylurea group, an arylthiourea group and an aryl $C_{1-6}$ alkylthiourean group each are unsubstituted or substituted by $R^{19}$ (said $R^{19}$ represents a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$), a formyl group, a cyano group or a nitro group)},

- $R^3$ and $R^4$ each independently represent a hydrogen atom or a $C_{1-6}$ alkyl group {said alkyl group is unsubstituted or substituted by a halogen atom, a $C_{1-6}$ alkoxy group or a hydroxyl group} or $R^3$ and $R^4$, together with the carbon atom to which they are bonded, form a $C_{3-6}$ cycloalkyl group.
- $R^5$ represents a hydroxyl group or a $C_{1-6}$ alkylcarbonyloxy group or forms a bond together with $R^6$,
- $R^6$ represents a hydrogen atom or forms a bond together with $R^5$,
- $R^7$ and $R^8$ each independently represent a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each is unsubstituted or substituted by $R^{19}$}, a phenyl group (said phenyl group is unsubstituted or substituted by $R^2$), $C(=Y^1)Z^1R^{10}$ or $C(=Y^1)R^{10}$ {$Y^1$ represents an oxygen atom, a sulfur atom or $NR^{11}$ ($R^{11}$ represents a hydrogen atom, a cyano group, a nitro group, a $C_{1-6}$ alkyl group or a $C_{1-6}$ alkoxy group), $Z^1$ represents an oxygen atom, a sulfur atom or $NR^{13}$ ($R^{13}$ has the same meaning as defined in $R^{10}$), $R^{10}$ represents a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each are unsubstituted or substituted by $R^{19}$) or a phenyl group (said phenyl group is unsubstituted or substituted by $R^2$)}, or
- $R^7$ and $R^8$ together form a 1,4-butylene or a 1,5-pentylene {said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-6}$ alkylcarbonyloxy group}, or
- $R^7$ and $R^8$ together form $(CH_2)_l X^1(CH_2)_p$ (in which l and p each represent 1, 2 or 3 while the sum of them is 3, 4 or 5, and $X^1$ represents an oxygen atom, a sulfur atom, $NR^{14}$ ($R^{14}$ represents a hydrogen atom, a $C_{1-4}$ alkyl group or a phenyl group (said phenyl group is unsubstituted or substituted by $R^2$))), or
- $R^7$ and $R^8$ together form $(CH_2)_q Z^1 C(=Y^1)$ or $(CH_2)_q C(=Y^1)$ (q represents 2, 3 or 4 and $Z^1$ and $Y^1$ have the same meanings as defined above), or
- $R^7$ and $R^8$, together with the nitrogen atom to which they are bonded, form a pyrrolyl group, a pyrazolyl group, an imidazolyl group, a 1,2,3-triazolyl group, a 1,2,4-triazolyl group or a 1,2,3,4-tetrazolyl group all of which are unsubstituted or substituted by $R^{15}$ ($R^{15}$ has the same meaning as defined in $R^{10}$)

n is 0 or an integer of 1 to 4,

X represents C=O, $CH_2$, $SO_2$ or $NR^{16}$ ($R^{16}$ has the same meanings as definend in $R^{14}$), Y represents $NR^{17}$ ($R^{17}$ has the same meanings as defined in $R^{14}$) when X is C=O, $CH_2$ or $SO_2$ and represents C=O when X is $NR^{16}$, Z is absent or represents $CH_2$ or $NR^{18}$ ($R^{18}$ has the same meanings as definend in $R^{14}$), W represents

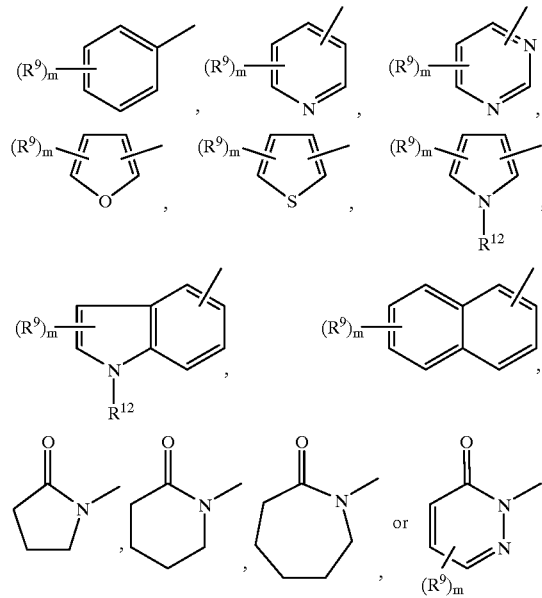

(in which $R^9$ represents a hydrogen atom, a halogen atom, a $C_{1-6}$ alkyl group (said alkyl group is unsubstituted or substituted by a halogen atom or a $C_{1-6}$ alkoxy group), a $C_{1-6}$ alkoxy group (said alkoxy group is unsubstituted or substituted by a halogen atom), a phenyl group (said phenyl group is unsubstituted or substituted by $R^2$), a hydroxyl group, a nitro group, a cyano group, a formyl group, a formamide group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group, a carboxyl group or an arylcarbonyl group, m is an integer of 1 to 3, and $R^{12}$ represents a $C_{1-4}$ alkyl group) or their salts.

2. A compound or their salts as claimed in claim 1, wherein a substituting position of $R^1$ on the chroman ring is at 7- or 8-position, a subisituting position of Z on the chroman ring is at 6-position and a combination of —X—Y—Z— is —C(O)—NH—, —C(O)—NMe—, —C(O)—NH—$CH_2$—, —$CH_2$—NH—, —$CH_2$—NH—$CH_2$—, —$SO_2$—NH— or —NH—C(O)—NH—.

3. A compound or their salts as claimed in claim 2, wherein both of $R^3$ and $R^4$ represent a $C_{1-6}$ alkyl group {said alkyl group is unsubstituted or substituted by a halogen atom, a $C_{1-6}$ alkoxy group or a hydroxyl group}.

4. A compound or their salts as claimed in claim 3, wherein $R^5$ presents a hydroxyl group or forms a bond together with $R^6$.

5. A compound or their salts as claimed in claim 2, wherein $R^7$ and $R^8$ each independently represent a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each is unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$ ($R^2$ represents a halogen atom, a hydroxyl group, a $C_{1-4}$ alkyl group or a $C_{1-4}$ alkoxy group)), a formyl group, a cyano group or a nitro group}, a phenyl group (said phenyl group is unsubtituted or substituted by $R^2$), $R^7$ and $R^8$ together form a 1,4-butylene or a 1,5-pentylene {said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-4}$ alkylcarbonyloxy group}, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ is unsubstituted or substituted by a hydrogen atom, a $C_{1-4}$ alkyl group or a phenyl group (said phenyl group is unsubstituted or substituted by $R^2$))), or $R^7$ and $R^8$, together with the nitrogen atom to which they are bonded, form a pyrrolyl group, a pyrazolyl group, an imidazolyl group, a 1,2,3-triazolyl group, a 1,2,4-triazolyl group or a 1,2,3,4-tetrazolyl group all of which are unsubstituted or substituted by $R^{15}$ ($R^{15}$ has the same meaning as defined in $R^{10}$).

6. A compound or their salts as claimed in claim 4, wherein $R^7$ and $R^8$ each independently represent a hydrogen atom, a $C_{1-6}$ alkyl group, a $C_{2-6}$ alkenyl group, a $C_{2-6}$ alkynyl group, a $C_{3-6}$ cycloalkyl group {said alkyl group, alkenyl group, alkynyl group and cycloalkyl group each are unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$ ($R^2$ represents a halogen atom, a hydroxyl group, a $C_{1-4}$ alkyl group or a $C_{1-4}$ alkoxy group)), a formyl group, a cyano group or a nitro group}, a phenyl group (said phenyl group is unsubtituted or substituted by $R^2$), $R^7$ and $R^8$ together form a 1,4-butylene or a 1,5-pentylene (said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-4}$ alkylcarbonyloxy group}, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ represents a hydrogen atom, a $C_{1-4}$ alkyl group or a phenyl group (said phenyl group is unsubstituted or substituted by $R^2$))), or $R^7$ and $R^8$, together with the nitrogen atom to which they are bonded, form a pyrrolyl group, a pyrazolyl group, an imidazolyl group, a 1,2,3-triazolyl group, a 1,2,4-triazolyl group or a 1,2,3,4-tetrazolyl group all of which is unsubstituted or substituted by $R^{15}$ ($R^{15}$ has the same meaning as defined above).

7. A compound or their salts as claimed in claim 2, wherein $R^1$ represents a hydrogen atom, a halogen atom, a $C_{1-6}$ alkyl group (said alkyl group is unsubstituted or substituted by a halogen atom, a $C_{1-6}$ alkoxy group or a hydroxyl group), a $C_{1-6}$ alkoxy group (said alkoxy group is unsubstituted or substituted by a halogen atom), a $C_{3-6}$ cycloalkyl group, a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, an aryl $C_{1-6}$ alkylaminocarbonyl group, a di (aryl $C_{1-6}$ alkyl)aminocarbonyl group, a $C_{1-6}$ alkylcarbonyl group, an arylcarbonyl group, an aryl $C_{1-6}$ alkylcarbonyl group, a $C_{1-6}$ alkoxycarbonyl group, an aryloxycarbonyl group, an aryl $C_{1-6}$ alkyloxycarbonyl group, a $C_{1-6}$ alkylcarbonylamino group, an arylcarbonylamino group or an aryl $C_{1-6}$ alkylcarbonylamino group.

8. A compound or their salts as claimed in claim 5, wherein $R^1$ represents a hydrogen atom, a halogen atom, a $C_{1-6}$ alkyl group (said alkyl group is unsubstituted or substituted by a halogen atom, a $C_{1-6}$ alkoxy group or a hydroxyl group), a $C_{1-6}$ alkoxy group (said alkoxy group is unsubstituted or substituted by a halogen atom), a $C_{3-6}$ cycloalkyl group, a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, an aryl $C_{1-6}$ alkylaminocarbonyl group, a di (aryl $C_{1-6}$ alkyl)aminocarbonyl group, a $C_{1-6}$ alkylcarbonyl group, an arylcarbonyl group, an aryl $C_{1-6}$ alkylcarbonyl group, a $C_{1-6}$ alkoxycarbonyl group, an aryloxycarbonyl group, an aryl $C_{1-6}$ alkyloxycarbonyl group, a $C_{1-6}$ alkylcarbonylamino group, an arylcarbonylamino group or an aryl $C_{1-6}$ alkylcarbonylamino group.

9. A compound or their salts as claimed in claim 6, wherein $R^1$ represents a hydrogen atom, a halogen atom, a $C_{1-6}$ alkyl group (said alkyl group is unsubstituted or substituted by a halogen atom, a $C_{1-6}$ alkoxy group or a hydroxyl group), a $C_{1-6}$ alkoxy group (said alkoxy group is unsubstituted or substituted by a halogen atom), a $C_{3-6}$ cycloalkyl group, a nitro group, a cyano group, a formyl group, a carboxyl group, a hydroxyl group, a formamido group, a cyanamide group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, an aryl $C_{1-6}$ alkylaminocarbonyl group, a di (aryl $C_{1-6}$ alkyl)aminocarbonyl group, a $C_{1-6}$ alkylcarbonyl group, an arylcarbonyl group, an aryl $C_{1-6}$ alkylcarbonyl group, a $C_{1-6}$ alkoxycarbonyl group, an aryloxycarbonyl group, an aryl $C_{1-6}$ alkyloxycarbonyl group, a $C_{1-6}$ alkylcarbonylamino group, an arylcarbonylamino group or an aryl $C_{1-6}$ alkylcarbonylamino group.

10. A compound or their salts as claimed in claim 7, wherein $R^9$ represents a hydrogen atom, a halogen atom, a $C_{1-6}$ alkyl group, a $C_{1-6}$ alkoxy group (said alkoxy group is unsubstituted or substituted by a halogen atom), a hydroxyl group, a nitro group, a cyano group, a formyl group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

11. A compound or their salts as claimed in claim 8, wherein $R^9$ represents a hydrogen atom, a halogen atom, a $C_{1-6}$ alkyl group, a $C_{1-6}$ alkoxy group (said alkoxy group is unsubstituted or substituted by a halogen atom), a hydroxyl group, a nitro group, a cyano group, a formyl group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

12. A compound or their salts as claimed in claim 9, wherein $R^9$ represents a hydrogen atom, a halogen atom, a $C_{1-6}$ alkyl group, a $C_{1-6}$ alkoxy group (said alkoxy group is unsubstituted or substituted by a halogen atom), a hydroxyl group, a nitro group, a cyano group, a formyl group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

13. A compound or their salts as claimed in claim 10, wherein $R^3$ and $R^4$ both represent a methyl group.

14. A compound or their salts as claimed in claim 11, wherein $R^3$ and $R^4$ both represent a methyl group.

15. A compound or their salts as claimed in claim 12, wherein $R^3$ and $R^4$ both represent a methyl group.

16. A compound or their salts as claimed in claim 15, wherein $R^7$ and $R^8$ each independently represent a hydrogen atom, a $C_{1-6}$ alkyl group, a $C_{3-6}$ cycloalkyl group {said alkyl group and cycloalkyl group each are unsubstituted or substituted by a halogen atom, a carboxyl group, a $C_{2-6}$ alkoxycarbonyl group, a hydroxyl group, a $C_{1-6}$ alkoxy group, a phenyl group (said phenyl group is unsubstituted or substituted by $R^2$ ($R^2$ represents a halogen atom, a hydroxyl group, a $C_{1-4}$ alkyl group or a $C_{1-4}$ alkoxy group)), a formyl group, a cyano group or a nitro group}, a phenyl group (said phenyl group is unsubstituted or substituted by $R^2$), or $R^7$ and $R^8$ together form a 1,4-butylene or a 1,5-pentylene {said butylene group and pentylene group each are unsubstituted or substituted by a $C_{1-4}$ alkyl group, a phenyl group (said phenyl group is unsubstituted or substituted by $R^2$), a halogen atom, a hydroxyl group, a $C_{1-4}$ alkoxy group or a $C_{1-4}$ alkylcarbonyloxy group}, or $R^7$ and $R^8$ together form $(CH_2)_l X^1 (CH_2)_p$ (in which l and p each represent 1, 2 or 3 while the sum of them is 3, 4 or 5, and $X^1$ represents an oxygen atom, a sulfur atom, $NR^{14}$ ($R^{14}$ represent a hydrogen atom, a $C_{1-4}$ alkyl group or a phenyl group (said phenyl group is unsubstituted or substituted by $R^2$))), or $R^7$ and $R^8$, together with the nitrogen atom to which they are bonded, form a pyrrolyl group, a pyrazolyl group or an imidazolyl which is unsubstituted orsubstituted by $R^{15}$ ($R^{15}$ has the same meaning as defined in $R^{10}$).

W represents

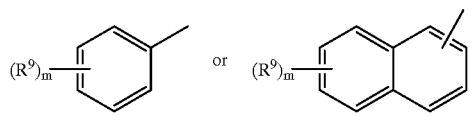

in which $R^9$ represents a hydrogen atom, a halogen atom, a $C_{1-6}$ alkyl group, a $C_{1-6}$ alkoxy group (said alkoxy group is unsubstituted or substituted by a halogen atom), a phenyl group (said phenyl group is unsubstituted or substituted by $R^2$), a hydroxyl group, a nitro group, a cyano group, a formyl group, a formamido group, an amino group, a $C_{1-6}$ alkylamino group, a di $C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di $C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group or a carboxyl group.

17. A compound or their salts as claimed in claim 16, wherein $R^1$ represents a hydrogen atom, a halogen atom, a $C_{1-6}$ alkyl group (said alkyl group is unsubstituted or substituted by a halogen atom), a $C_{3-6}$ cycloalkyl group, a nitro group, a cyano group, a formyl group, a carboxyl group, a hydroxyl group, a formamido group, an amino group, a $C_{1-6}$ alkylamino group, a di $C_{1-6}$ alkylamino group, a $C_{1-6}$ alkylcarbonylamino group, an arylcarbonylamino group, an aryl $C_{1-6}$ alkylcarbonylamino group, an aminocarbonyl group, a $C_{1-6}$ alkylaminocarbonyl group, a di $C_{1-6}$ alkylaminocarbonyl group, or a $C_{1-6}$ alkoxycarbonyl group.

18. A compound or their pharmacologically acceptable salts as claimed in claim 17, wherein $R^7$ and $R^8$ each independently represent a hydrogen atom, a $C_{1-6}$ alkyl group, a $C_{3-6}$ cycloalkyl group, or $R^7$ and $R^8$ together form a 1,4-butylene or a 1,5-pentylene, or $R^7$ and $R^8$ together form $(CH_2)_l X^1 (CH_2)_p$ (in which l and peach represent 1, 2 or 3 while the sum of them is 3, 4 or 5, and $X^1$ represents an oxygen atom, a sulfur atom, $NR^{14}$ ($R^{14}$ represents a hydrogen atom or a $C_{1-4}$ alkyl group)), or $R^7$ and $R^8$, together with the nitrogen atom to which they are bonded, form a pyrrolyl group or an imidazolyl group.

19. A compound or their pharmacologically acceptable salts as claimed in claim 18, wherein the combination of X—Y—Z is —C(O)—NH—, —C(O)—NMe— or —NH—C(O)—NH—.

20. A compound and salts thereof as claimed in claim 19, wherein $R^1$ represents a hydrogen atom, a nitro group, a cyano group, a carboxyl group, an amino group, a $C_{1-6}$ alkylamino group, a di $C_{1-6}$ alkylamino group, a $C_{1-6}$ alkylcarbonylamino group, an aryl $C_{1-6}$ alkylcarbonylamino group or a $C_{1-6}$ alkoxycarbonyl group.

21. A compound or their salts as claimed in claim 20, wherein $R^1$ represents a nitro group or a cyano group.

22. A compound or their salts as claimed in claim 21, wherein $R^7$ represents a $C_{1-6}$ alkyl group or a $C_{3-6}$ cycloalkyl group, $R^8$ represents a hydrogen atom, and $R^7$ and $R^8$ together represent a 1,4-butylene, or $R^7$ and $R^8$, together with the nitrogen atom to which they are bonded, form a pyrrolyl group.

23. A compound or their salts as claimed in claim 22, wherein $R^1$ represents a nitro group, and $R^7$ and $R^8$, together with the nitrogen atom to which they are bonded, form a pyrrolyl group, and the combination of X—Y—Z is —C(O)—NH—, and $R^9$ represents a hydrogen atom or a $C_{1-6}$ alkoxy.

24. A compound or their salts as claimed in claim 22, wherein $R^1$ represents a nitro group, and $R^7$ and $R^8$ together represent a 1,4-butylene, $R^9$ represents a hydrogen atom, a fluorine atom, a chlorine atom, a methyl group, a methoxy group, an ethoxy group or a nitro group.

25. A compound or their salts as claimed in claim 22, wherein $R^1$ represents a nitro group, $R^7$ represents a cyclopropyl group, $R^8$ represents a hydrogen atom, $R^9$ represents a hydrogen atom, a methoxy group, an ethoxy group, a phenyl group, a nitro group, a hydroxyl group, a methylamino group, a dimethylamino group or an acetamido group, and the combination of X—Y—Z is —C(O)—NH—.

26. A compound or their salts as claimed in claim 22, wherein $R^1$ represents a nitro group, $R^7$ represents a methyl group or an isopropyl group, $R^8$ represents a hydrogen atom and $R^9$ represents a hydrogen atom, a methoxy group, a phenyl group, a nitro group or an acetamido group.

27. A pharmaceutical composition containing as an active ingredient the compound or their salts as claimed in claim 1.

28. A pharmaceutical composition for curing cardiac insuffiency containing as an active ingredient the compound or their salts as claimed in claim 1.

* * * * *

UNITED STATES PATENT AND TRADEMARK OFFICE
CERTIFICATE OF CORRECTION

PATENT NO. : 6,066,631
DATED : May 23, 2000
INVENTOR(S) : Keizo Tanikawa; Kazuhiko Ohrai; Masayuki Sato; Toru Yamashita and Kazufumi Yanagihara It is certified that error appears in the above-identified patent and that said Letters Patent is hereby corrected as shown below:

Title page,

Column 1,
Section [30], change "July 19, 1996" to -- July 26, 1996 --.

Signed and Sealed this

Twenty-eighth Day of August, 2001

Attest:

*Attesting Officer*

NICHOLAS P. GODICI
*Acting Director of the United States Patent and Trademark Office*